(12) United States Patent
Bezwada et al.

(10) Patent No.: US 9,328,192 B2
(45) Date of Patent: May 3, 2016

(54) BIO-BASED MONOMERS AND POLYMERS

(71) Applicant: Bezwada Biomedical, LLC, Hillsborough, NJ (US)

(72) Inventors: Rao S Bezwada, Hillsborough, NJ (US); Neeti Srivastava, Hillsborough, NJ (US)

(73) Assignee: Bezwada Biomedical, LLC, HIllsborough, NJ (US)

( * ) Notice: Subject to any disclaimer, the term of this patent is extended or adjusted under 35 U.S.C. 154(b) by 0 days.

(21) Appl. No.: 14/645,522

(22) Filed: Mar. 12, 2015

(65) Prior Publication Data

US 2015/0259464 A1 Sep. 17, 2015

Related U.S. Application Data

(60) Provisional application No. 61/951,617, filed on Mar. 12, 2014.

(51) Int. Cl.

| | | |
|---|---|---|
| *C08G 18/76* | (2006.01) | |
| *C08G 71/02* | (2006.01) | |
| *C08G 69/00* | (2006.01) | |
| *C08G 73/02* | (2006.01) | |
| *C08G 18/60* | (2006.01) | |
| *C08G 18/77* | (2006.01) | |
| *C08G 18/81* | (2006.01) | |
| *C07C 265/14* | (2006.01) | |

(52) U.S. Cl.
CPC .......... *C08G 18/7657* (2013.01); *C07C 265/14* (2013.01); *C08G 18/603* (2013.01); *C08G 18/771* (2013.01); *C08G 18/8125* (2013.01); *C08G 69/00* (2013.01); *C08G 71/02* (2013.01); *C08G 73/02* (2013.01); *C08G 2230/00* (2013.01); *Y10T 428/1352* (2015.01); *Y10T 428/1355* (2015.01); *Y10T 428/1393* (2015.01); *Y10T 428/24999* (2015.04); *Y10T 428/249991* (2015.04); *Y10T 428/2804* (2015.01); *Y10T 428/2896* (2015.01); *Y10T 428/31551* (2015.04); *Y10T 428/31605* (2015.04); *Y10T 442/20* (2015.04)

(58) Field of Classification Search
CPC .... C08G 18/7657; C08G 71/02; C08G 73/02; C08G 69/00; C08G 18/8125; C08G 18/771; C08G 18/603; C07C 265/14
See application file for complete search history.

(56) References Cited

U.S. PATENT DOCUMENTS

| | | | |
|---|---|---|---|
| 3,427,346 A * | 2/1969 | Brotherton | ............ C07C 263/16 521/162 |
| 4,740,534 A | 4/1988 | Matsuda et al. | |
| 4,826,945 A | 5/1989 | Cohn et al. | |
| 4,829,099 A | 5/1989 | Fuller et al. | |
| 4,994,542 A | 2/1991 | Matsuda et al. | |
| 5,173,301 A | 12/1992 | Itoh et al. | |
| 6,221,997 B1 | 4/2001 | Woodhouse et al. | |
| 6,894,140 B2 | 5/2005 | Roby | |
| 8,309,132 B2 | 11/2012 | Bezwada | |
| 8,551,519 B2 | 10/2013 | Bezwada | |
| 8,664,429 B2 | 3/2014 | Bezwada | |
| 8,901,341 B2 | 12/2014 | Bezwada | |
| 8,901,347 B1 | 12/2014 | Bezwada | |
| 2004/0170597 A1 | 9/2004 | Beckman et al. | |
| 2005/0013793 A1 | 1/2005 | Beckman et al. | |
| 2007/0014755 A1 | 1/2007 | Beckman et al. | |

FOREIGN PATENT DOCUMENTS

| | | |
|---|---|---|
| EP | 0295055 A2 | 12/1988 |
| WO | 95/26762 A1 | 10/1995 |

OTHER PUBLICATIONS

Krishnamurti, "Vinyl monomers from 12-hydroxystearic acid," Pigments and Resin Technology (1980), 9, (4), 15-17.*

* cited by examiner

*Primary Examiner* — Paul A Zucker
*Assistant Examiner* — Mark Luderer
(74) *Attorney, Agent, or Firm* — Vance Intellectual Property, PC

(57) ABSTRACT

Described are novel ricinoleic acid/12-hydroxy stearic acid-based diisocyanates, which are useful as monomers to form polymers, which have applications inter alia as medical devices.

30 Claims, No Drawings

BIO-BASED MONOMERS AND POLYMERS

FIELD OF THE INVENTION

The present invention relates to the discovery of a new class of bio-based monomers and polymers. Using these bio-based monomers and their functionalized derivatives, novel bio-based absorbable/biodegradable and non-absorbable polymers (or partially absorbable/biodegradable polymers) can be prepared.

BACKGROUND OF THE INVENTION

Bio-based and/or biodegradable polymers are increasingly being used in applications that currently rely on petroleum based feedstocks. These biobased and/or biodegradable monomers and polymers have become increasingly important for a variety of consumer products, durable goods and biomedical applications including tissue engineering scaffolds, surgical adhesives, foams, medical device coatings and drug delivery matrices, etc. They are also increasingly being used for disposable medical device applications. For example, isocyanate-based adhesive/sealant compositions are described in U.S. Pat. Nos. 6,894,140; 5,173,301; 4,994,542; and, 4,740,534, the disclosures of which are incorporated herein by reference in their entirety.

Polymers that are derived from monomers from renewable biobased sources are referred to as bio-based polymers. Polymers that breakdown into carbon dioxide, water and biomass from the action of naturally occurring microorganism such as bacteria, fungi etc over a period of time are referred to as biodegradable polymers. A majority of the biobased polymers are also biodegradable. Polymers that are designed to degrade under physiological conditions are referred to as absorbable polymers. These polymers are sometimes also referred to as, bioerodible, bioabsorbable, or hydrolyzable polymers. Synthetic absorbable polymers are generally classified into polyesters, polyorthoesters, polyanhydrides, polyesteramides, and polyoxaesters.

Absorbable polymers are increasingly used in a wide range of biomedical applications including tissue engineering scaffolds, stents, stent coatings, foams, highly porous foams, reticulated foams, and adhesion prevention barriers. This increased utilization is, in part, a function of the transient nature of these polymers when used as biomedical implants or drug carriers. Medical devices made from absorbable polymers can mitigate the inevitable and usually negative physiologic responses (e.g., fibrous encapsulation), which limit long-term device success. Hence, an array of absorbable polymers have been developed and studied in various biomedical applications. While significant research and development activity has been carried out on bioabsorbable polymers, such polymers may suffer from performance deficiencies which are typically not fully recognized until new applications are identified and in-use testing has been carried out.

Of the synthetic absorbable polymers, polyesters find numerous applications in medical, surgical and controlled delivery applications and are the key components of a majority of bioabsorbable medical devices, ranging from sutures, staples, orthopedic screws and implantable surgical devices to tissue engineering scaffolds.

In addition to polyesters, segmented polyurethane elastomers have also enjoyed wide use as biomaterials generally due to their excellent mechanical properties and desirable chemical versatility. While polyurethane polymers have certain useful properties, shaped articles based on these polymers are not typically absorbable or biodegradable and may therefore be unacceptable in circumstances that require absorption or biodegradation. For example, certain biomedical applications, such as surgical devices including but not limited to monofilament and multifilament sutures, films, sheets, plates, clips, staples, pins, screws, stents, stent coatings, and the like, generally require the use of a material that is absorbable. Hence, the vast majority of research devoted to the development of biomedical polyurethanes has focused on long-term applications such as vascular grafts and pacemaker lead insulators.

Despite progress in the general development of polyurethanes and similar polymers for use in biomedical applications, relatively little research have been directed to developing absorbable polyurethanes for temporary, rather than longer-term implantation. See Fuller et al., U.S. Pat. No. 4,829,099; Beckmann et al., U.S. Patent Publication Nos. 2005/0013793, 2004/0170597, and 2007/0014755; Bruin et al., PCT Publication No. WO 95/26762; Woodhouse et al., U.S. Pat. No. 6,221,997; Cohn et al., U.S. Pat. No. 4,826,945, which generally discuss recent advances made in the field of absorbable polyurethanes.

Subsequent work by Bruin et al., PCT No. WO 95/26762, describes the synthesis of crosslinked polyurethane networks incorporating lactide or glycolide and $\epsilon$-caprolactone joined by a lysine-based diisocyanate. Bruin discloses that these polymers display good elastomeric properties and degrade within about 26 weeks in vitro and about 12 weeks in vivo (subcutaneous implantation in guinea pigs). Despite their disclosed desirable flexibility and degradation characteristics, these highly crosslinked polymers are not extensively used in some biomedical applications because in some cases they cannot be readily processed into surgical articles, for example, using standard techniques such as solution casting or melt processing, as is the case for the more typical linear, segmented polyurethanes.

Cohn et al., EP 295055 describes a series of elastomeric polyester-polyether-polyurethane block copolymers intended for use as surgical articles. However, these polymers may be relatively stiff and may have low tensile strength, which may preclude their use as elastomeric biomaterials. Beckmann et al., U.S. Patent Publication No. 2005/0013793 describes polyurethane-based biodegradable adhesives from multi-isocyanate functional molecules and multifunctional precursor molecules with terminal groups selected from hydroxyl and amino groups. Woodhouse et al. describes absorbable polyurethanes derived from amino acids. However, all these absorbable polyurethanes may suffer from one or more of the following drawbacks: (a) the very slow rate of formation of polyurethane that may be attributed to the low reactivity of the polyisocyanates and (b) the lack of tunable physical and/or mechanical properties and/or controllable hydrolytic degradation profiles for biodegradable polyisocyanates or absorbable polyurethanes derived therefrom.

Despite advancements in the art of producing polymeric materials and methods for making polymers suitable for use in drug delivery, tissue adhesives, adhesion prevention barrier, foams, highly porous foams, reticulated foams, bone wax formulations, stents, stent coatings, scaffolds, films, molded devices, and similar surgical articles, presently available polymers generally lack adequate performance properties desirable in surgical articles, for example, those related to bioabsorption, flex fatigue life, strength in use, flexibility, and/or durability. Thus, there continues to be a need for new devices and polymers having tunable physical and/or biological properties, so that medical devices and surgical articles having a variety of end uses can be prepared.

With more uses being envisioned for polymers and an increased demand for absorbable polymers with new and improved properties targeted to address performance deficiencies, there still is a need for bio-based monomers and polymers with beneficial properties.

SUMMARY OF THE INVENTION

In an embodiment, the present invention provides a novel class of bio-based monomers and materials (e.g., pre-polymers, polymers, polyols, and/or oligomers) derived therefrom. The bio-based materials may be biodegradable, absorbable, and/or non-absorbable.

In another embodiment, the present invention provides novel bio-based materials useful for a variety of medical (e.g., stent coatings), pharmaceutical (e.g., drug formulations), and cosmetic (e.g., cosmetic packaging) uses.

In another embodiment, the present invention provides novel bio-based vegetable oil (e.g., castor or soybean) derived hydroxyl acids diacids, diamines, and diisocyanates and the resulting polymers including bio-based polyamides, polyesters, polyureas, polyepoxides, polyesteramides, and polyurethanes.

In another embodiment, the present invention provides novel bio-based materials and methods of making such materials that would ultimately be useful for drug delivery matrices (e.g., controlled drug delivery or site-specific or systemic drug delivery systems or matrices), pharmaceutical drug formulations, tissue engineering (e.g., tissue scaffold), tissue adhesives, adhesion prevention barriers, and other implantable medical devices including foams (including reticulated foams, lyophilized foams, highly porous foams, regular foams, foams with vertical channels, architecturally gradient foams, trans-compositional foams, and trans-structural foams) for wound healing and/or drug delivery, bone hemostats, bone fillers, bone void fillers, bone wax formulations, tissue adhesives and sealants, adhesion prevention barriers, meshes, filters, surgical devices (e.g., stents, staples, sutures (e.g., monofilament and multifilament sutures), screws (e.g., orthopedic screws), sheets, plates, clips, films, staples, pins, hooks, buttons, snaps, tubes, vascular grafts, bone plates, implantable sensors, and molded devices), medical device coatings (e.g., for endoscopic instruments, sutures, stents, and needles), cosmetic and pharmaceutical packaging (e.g., blister packaging films, cast films, extruded films and containers), apparels, infusion devices, blood collection tubes and devices, tubes, skin care products, transdermal drug delivery, consumer product packaging, and disposable medical devices, durable consumer goods, knitted products, foodstuffs, nutritional supplements, nutraceuticals, biodegradable chewing gums, and reinforced composites.

These and other embodiments, which will become apparent during the following detailed description, have been achieved by the inventors' discovery of the presently claimed bio-based monomers and polymers thereof.

DETAILED DESCRIPTION OF PREFERRED EMBODIMENTS

The entire disclosures of all cited patents and patent publications are incorporated in their entirety herein by reference.

In an embodiment, the present invention provides a novel class of bio-based monomers and materials derived therefrom (e.g., polymers, pre-polymers, polyols, and/or oligomers). The bio-based materials may be biodegradable, absorbable, and/or non-absorbable. The bio-based monomers are derived from starting compounds that include butane diol, succinic acid, L-lactic acid, amino acids such as L-lysine, castor oil-based monomers (e.g., ricinoleic acid, 12-hydroxy stearic acid, and sebacic acid), and soybean oil-based monomers.

In an embodiment, the present invention provides a novel class of polymers formed by polymerizing a bio-based monomer with an appropriate additional monomer (e.g., a diol/polyol, or diamine), the polymers being selected from: polyamides, polyesters, polyureas, polyepoxides, polyesteramides, and polyurethanes. The polymers are biodegradable, absorbable, and/or non-absorbable. For the preparation of bio-based polyamides, bio-based diamines such as 1,5-pentane diamine and L-lysine can be reacted with bio-based dicarboxylic acids, such as sebacic acid or succinic acid. Absorbable bio-based polyamides can be prepared by functionalizing sebacic acid with a group such as lactic acid and reacting with diamines. The absorbable polymers are characterized by having a controllable degradation profile.

In another embodiment, the present invention provides novel bio-based materials useful for drug delivery matrices (e.g., controlled drug delivery or site-specific or systemic drug delivery systems or matrices), pharmaceutical drug formulations, tissue engineering (e.g., tissue scaffold), tissue adhesives, adhesion prevention barriers, and other implantable medical devices including foams (including reticulated foams, lyophilized foams, highly porous foams, regular foams, foams with vertical channels, architecturally gradient foams, trans-compositional foams, and trans-structural foams) for wound healing and/or drug delivery, bone hemostats, bone fillers, bone void fillers, bone wax formulations, tissue adhesives and sealants, adhesion prevention barriers, meshes, filters, surgical devices (e.g., stents, staples, sutures (e.g., monofilament and multifilament sutures), screws (e.g., orthopedic screws), sheets, plates, clips, films, staples, pins, hooks, buttons, snaps, tubes, vascular grafts, bone plates, implantable sensors, and molded devices), medical device coatings (e.g., for endoscopic instruments, sutures, stents, and needles), cosmetic and pharmaceutical packaging (e.g., blister packaging films, cast films, extruded films and containers), apparels, infusion devices, blood collection tubes and devices, tubes, skin care products, transdermal drug delivery, consumer product packaging, and disposable medical devices, durable goods, knitted products, foodstuffs, nutritional supplements, nutraceuticals, biodegradable chewing gums, and reinforced composites.

Examples of knitted products, woven or non-woven, and molded products include: burn dressings; hernia patches; medicated dressings; fascial substitutes; gauze, fabric, sheet, felt, or sponge for liver hemostasis; gauze bandages; arterial graft or substitutes; bandages for skin surfaces; suture knot clip; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; and, artificial skin.

As described herein, the functionalized monomers and polymers of the present invention are useful in medical applications/medical devices. Medical application/medical devices, as used herein, encompass medical and biomedical applications and include all types of applications involved in the practice of medicine that would benefit from a material that decomposes harmlessly within a known period of time.

In another embodiment, the present invention provides a novel diisocyanate selected from formula (I), (II), or (III):

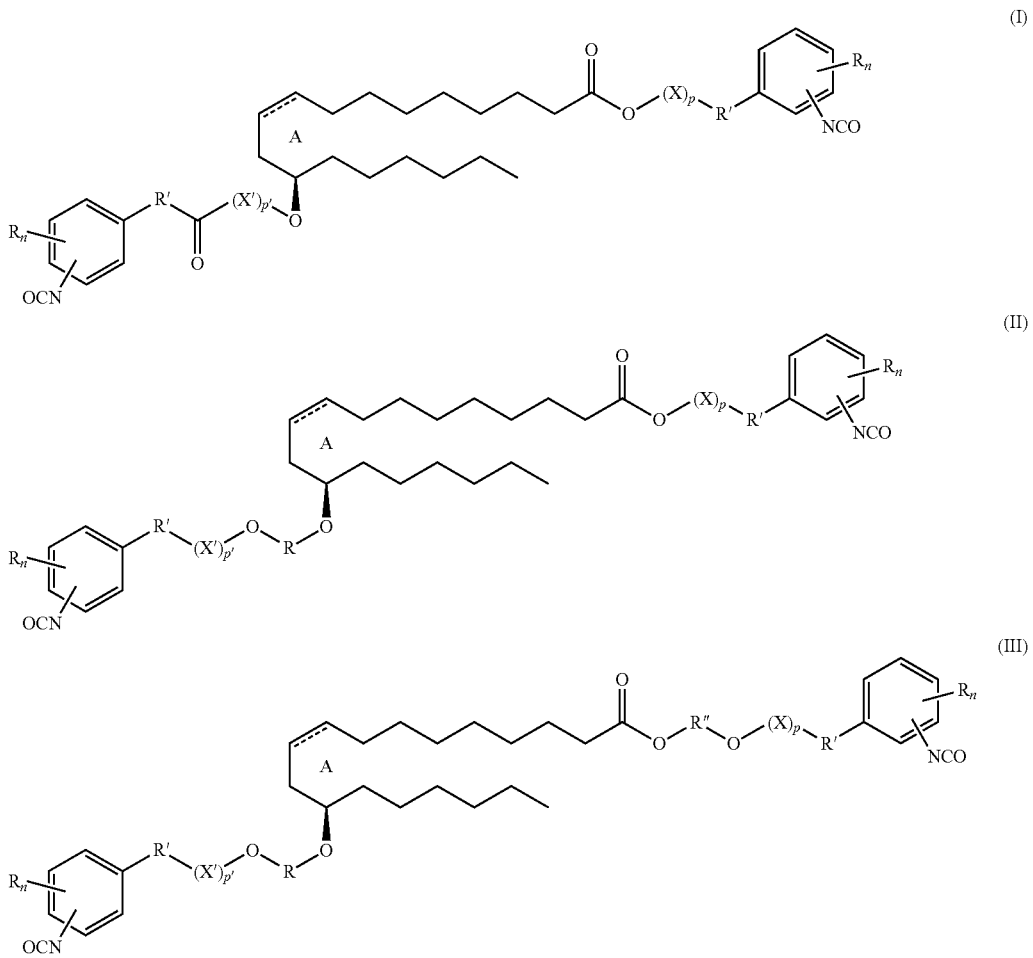

wherein:
variable A, the dashed bond, is absent or is a double bond;
R is the diacyl residue of a diacid;
R' is absent or each R' is independently a $C_{1-6}$ alkylene group;
R" is the residue of a diol or polyol;
from 1-4 $R_n$ are present;
each $R_n$ is independently selected from: H, $C_{1-6}$ alkyl, $C_{1-6}$ alkoxy, benzyloxy, halogen, —CHO, —CO$_2$H, and —NO$_2$, and each $R_n$ is independently attached directly to aromatic ring or attached through a —(CH$_2$)$_{1-4}$— linker;
each X independently is selected from:
—CH$_2$COO— (glycolic acid moiety);
—CH(CH$_3$)COO— (lactic acid moiety);
—CH$_2$CH$_2$OCH$_2$COO— (dioxanone moiety);
—CH$_2$CH$_2$CH$_2$CH$_2$CH$_2$COO— (caprolactone moiety);
—(CH$_2$)$_y$COO— where y is selected from 2, 3, 4, and 6-24; and
—(CH$_2$CH$_2$O)$_z$CH$_2$COO— where z is selected from 2-24;
each X' independently is selected from:
—OCH$_2$CO— (glycolic acid moiety);
—OCH(CH$_3$)CO— (lactic acid moiety);
—OCH$_2$CH$_2$OCH$_2$CO— (dioxanone moiety);
—OCH$_2$CH$_2$CH$_2$CH$_2$CH$_2$CO— (caprolactone moiety);
—O(CH$_2$)$_y$CO— where y is selected from 2, 3, 4, and 6-24; and,
—O(CH$_2$CH$_2$O)$_z$CH$_2$CO— where z is selected from 2-24;
each p is independently selected from 0, 1, 2, 3, 4, 5, and 6; and,
each p' is independently selected from 0, 1, 2, 3, 4, 5, and 6;
provided that p+p' total from 0 to 12.

As noted, R is the diacyl (i.e., C(O)—R$^A$—C(O)) residue of a diacid.

R$^A$ is independently selected from: alkylene, cycloalkylene-alkylene, arylene-alkylene, arylene-alkylene-arylene, cycloalkylene-alkylene-cycloalkylene, and arylene-alkylene-cycloalkylene, wherein:

(1) one or more of the methylene (—CH$_2$—) moieties in the alkylene chain portions of the R$^A$ group are optionally replaced by —O— or —S—; or (2) one or more of the ethylene (—CH$_2$CH$_2$—) moieties in the alkylene chain portions of the R$^A$ group are optionally replaced by a carboxyl group (—C(=O)O— or —OC(=O)—).

Examples of diacids from which R can be derived include oxalic acid, malonic acid, succinic acid, glutaric acid, adipic acid, pimelic acid, suberic acid, azelaic acid, sebacic acid, phthalic acid, isophthalic acid, terephthalic acid, maleic acid, fumaric acid, glutaconic acid, traumatic acid, muconic acid, diglycolic acid, 3,6-dioxaoctanedioic acid, 3,6,9-trioxaundecanoic acid, functionalized oxaacids, polyethyleneglycol diacids of average molecular weight from 300 to 2000 and blends thereof, symmetrical/unsymmentrical ether acids, as well as bio-based diacids and their precursors, including, succinic acid, sebacic acid, hydroxyl acids, and diacids derived from vegetable oils including castor oil (e.g., ricinoleic acid, 12-hydroxy stearic acid, and sebacic acid) and soybean oil.

As noted, R" is the residue of a diol or polyol. When R" is the residue of a diol, then it is the $R^A$ portion of HO—$R^A$—OH. Alternatively, when R" is the residue of a polyol, it is, excluding the terminal hydroxy groups, selected from polyalkylene oxides having weight average molecular weights from about 500-10,000.

Examples of suitable diols from which R" can be derived include diols with up to 8 carbon atoms or diols having repeating units each with up to 8 carbon atoms. Diol examples include 1,2-ethanediol (ethylene glycol); 1,2-propanediol (propylene glycol); 1,3-propanediol; 1,4-butanediol; 1,5-pentanediol; 1,3-cyclopentanediol; 1,6-hexanediol; 1,4-cyclohexanediol; 1,8-octanediol; and, combinations thereof.

Examples of suitable polyols from which R" can be derived include polyethylene glycol and polypropylene glycol with weight average molecular weights of 500-10,000.

In another embodiment, the present invention provides a novel diisocyanate selected from formulae (Ia)-(IIIa):

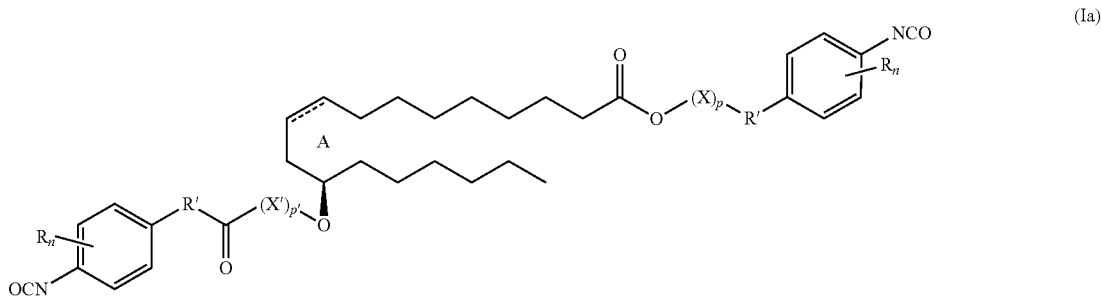

(Ia)

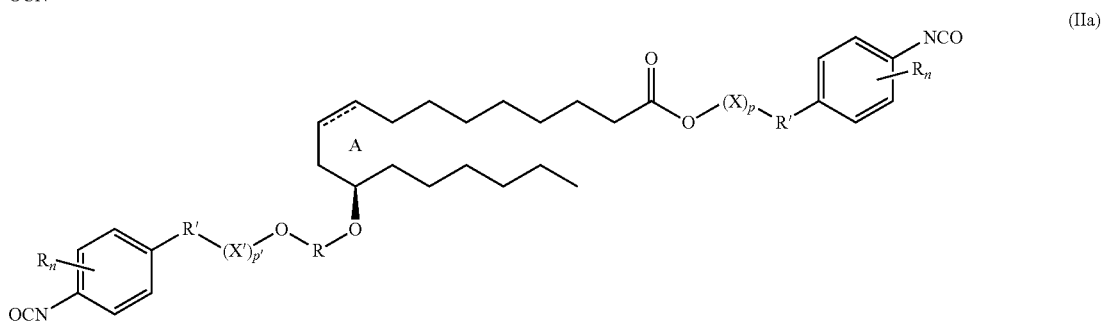

(IIa)

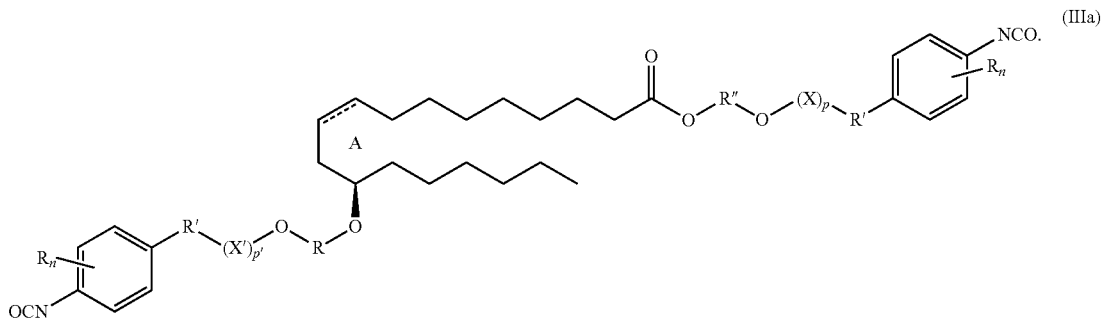

(IIIa)

In another embodiment, the present invention provides a novel diisocyanate selected from formulae ($Ia_1$)-($IIIa_2$):

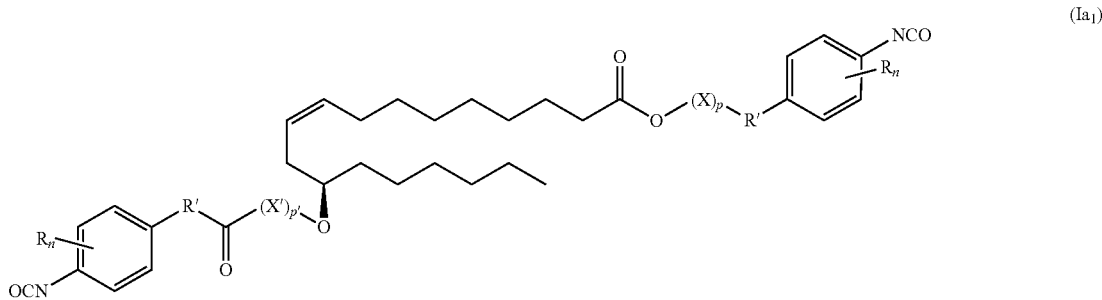

($Ia_1$)

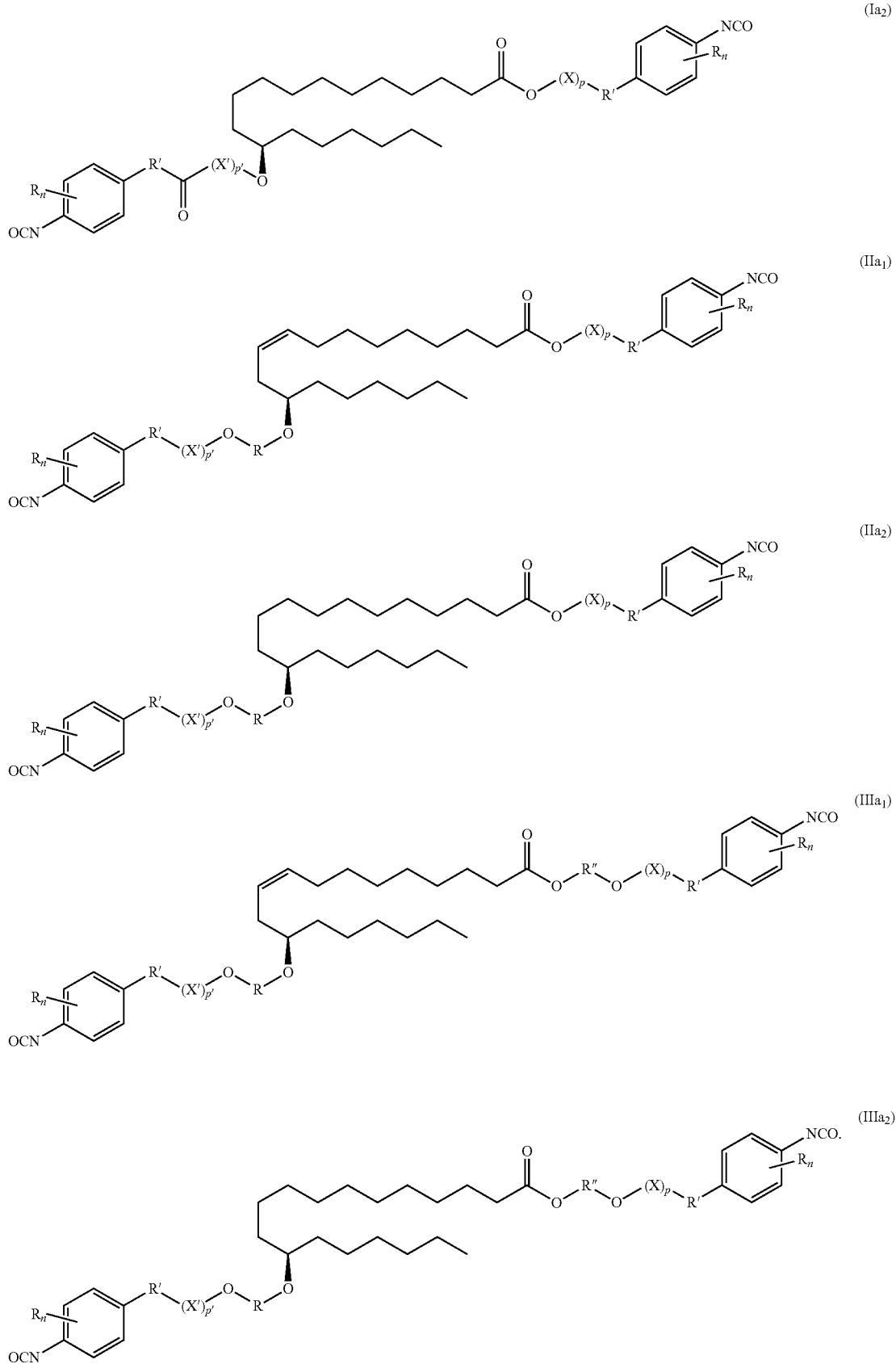

In another embodiment, the present invention provides a novel diisocyanate selected from formulae ($Ia_{1A}$)-($IIIa_{2A}$):
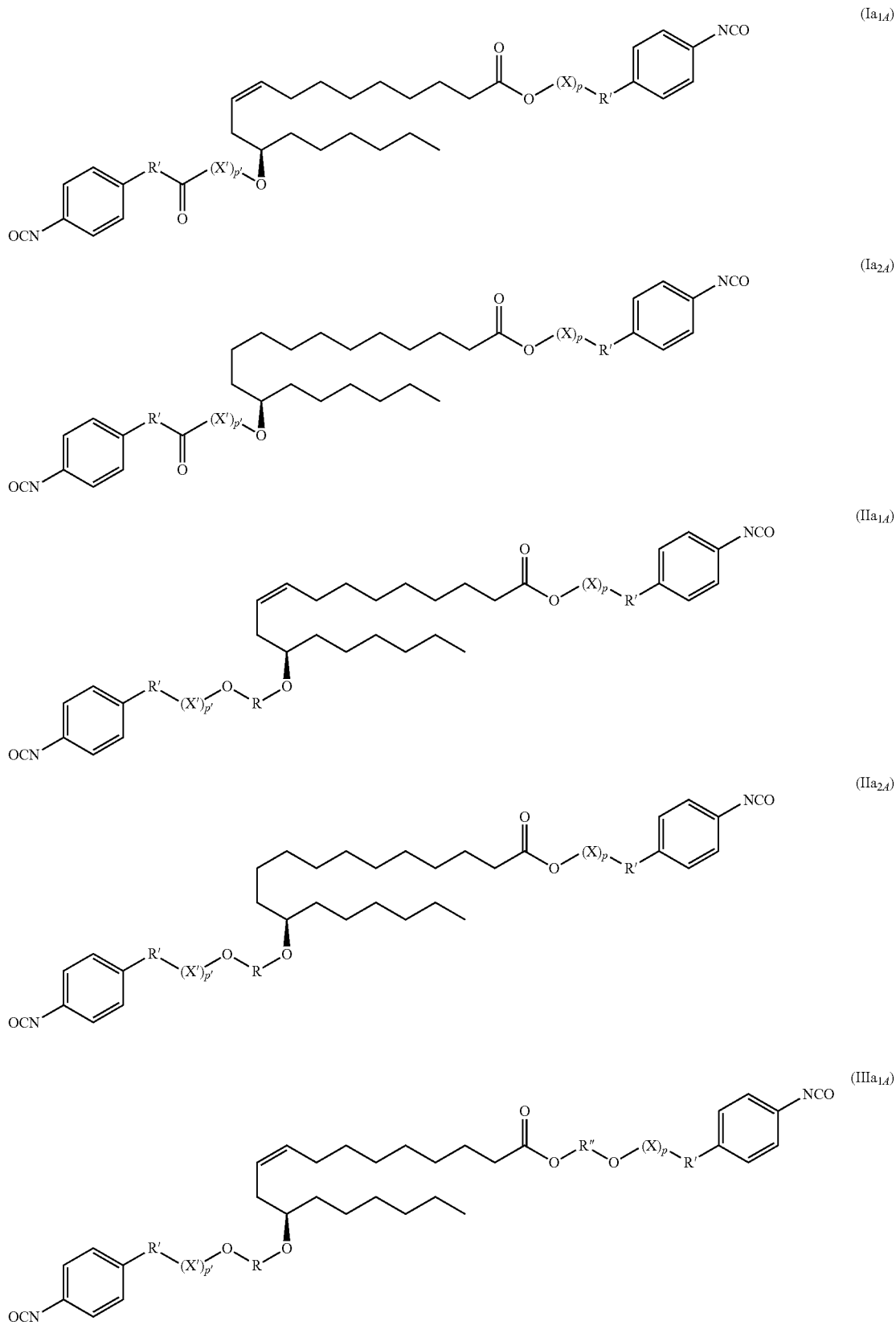

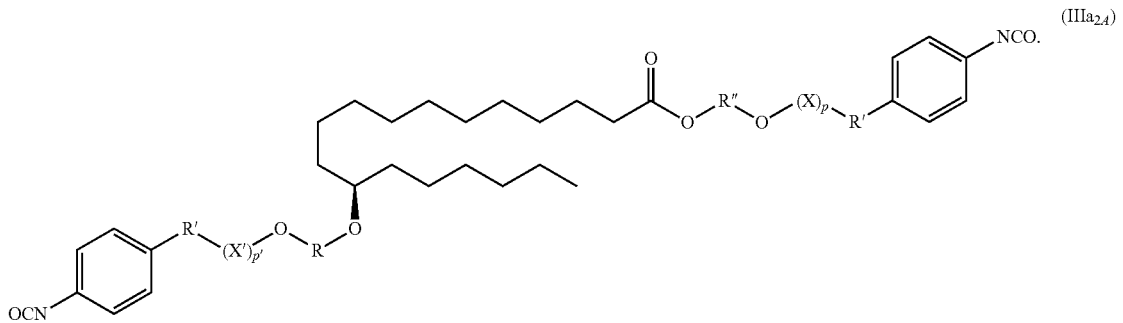
In another embodiment, the present invention provides a novel diisocyanate selected from formulae (1)-(20):
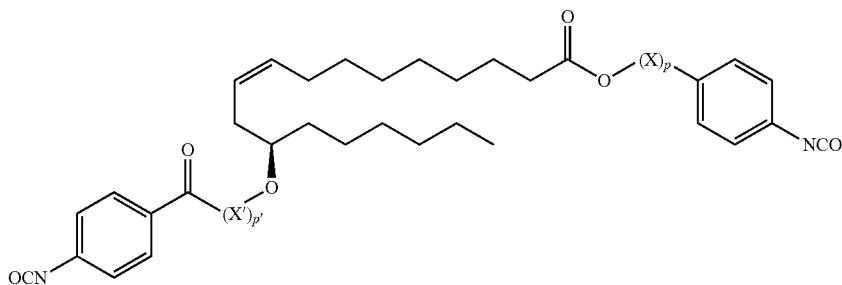
(1)
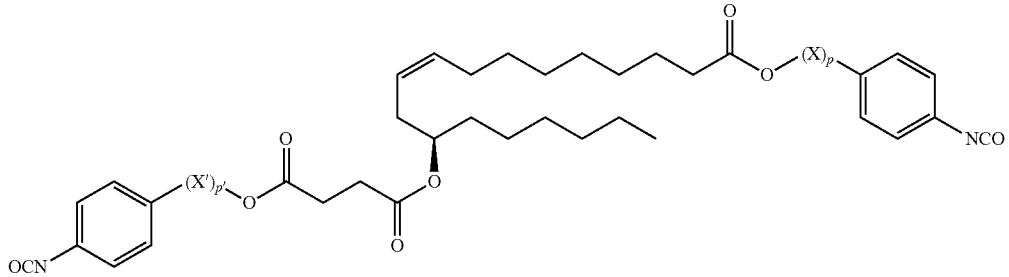
(2)
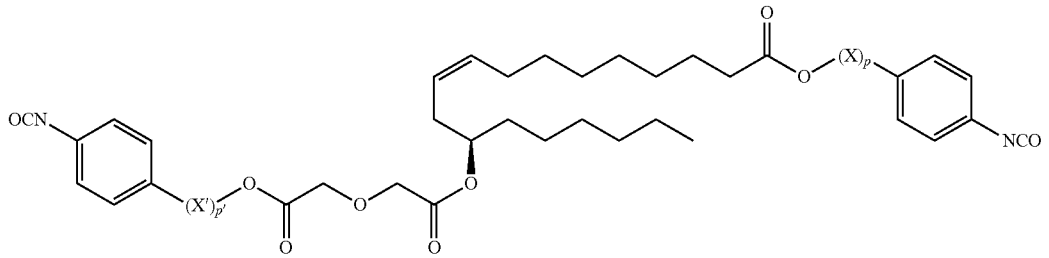
(3)
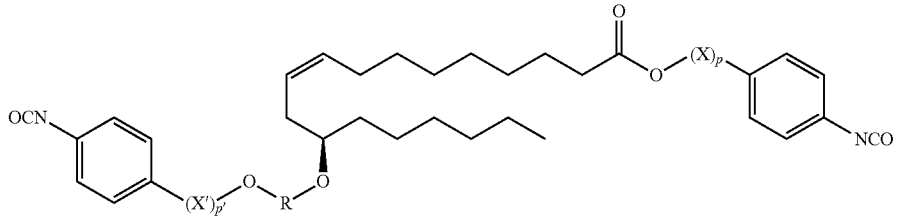
(4)

-continued
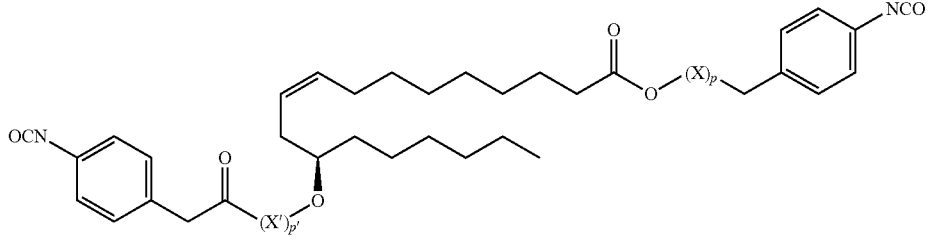
(5)
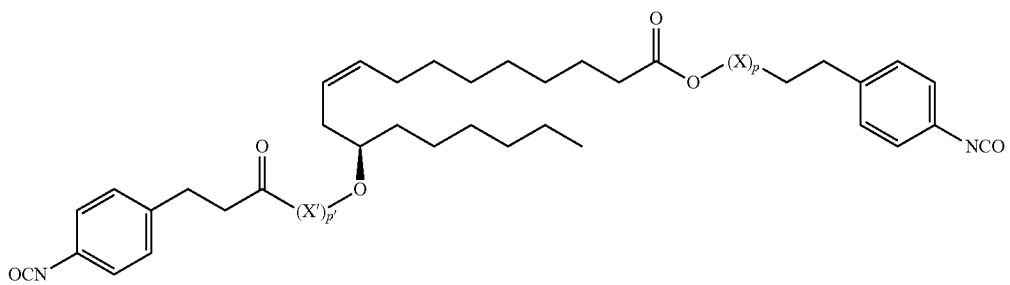
(6)
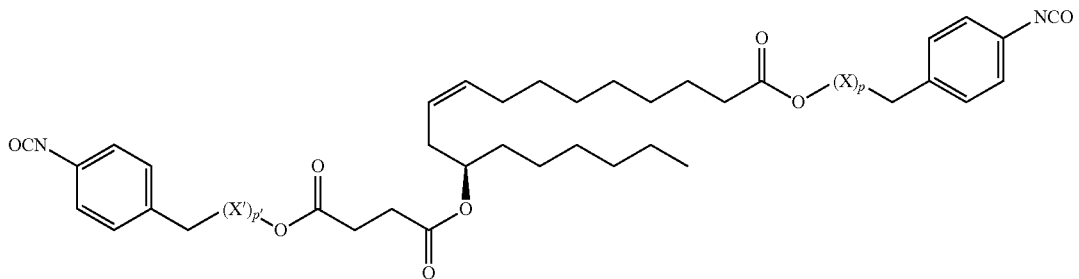
(7)
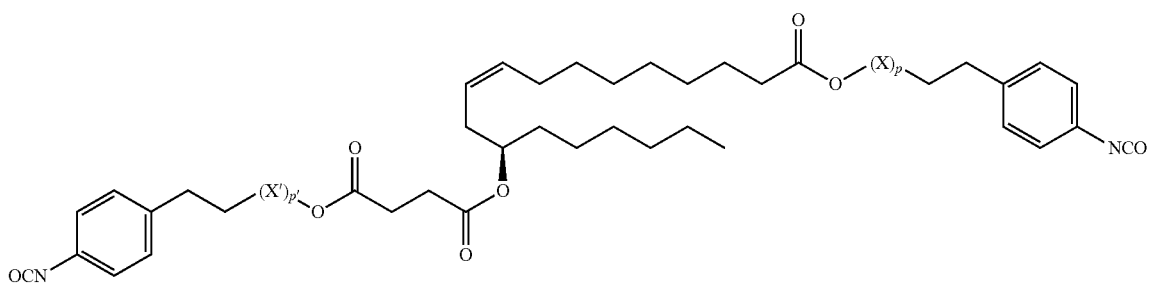
(8)
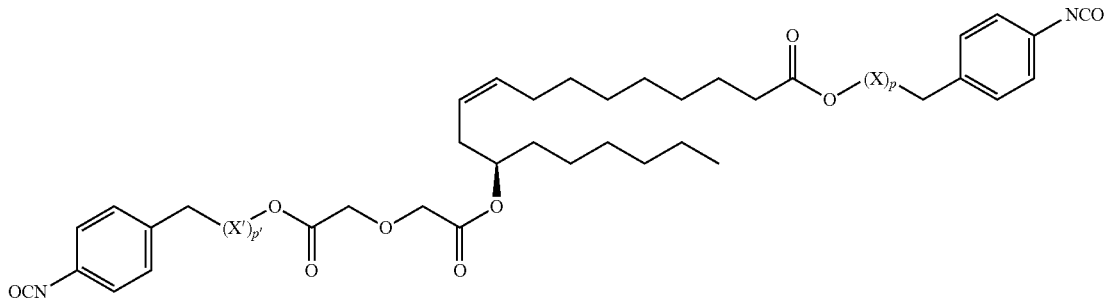
(9)

-continued
(10)
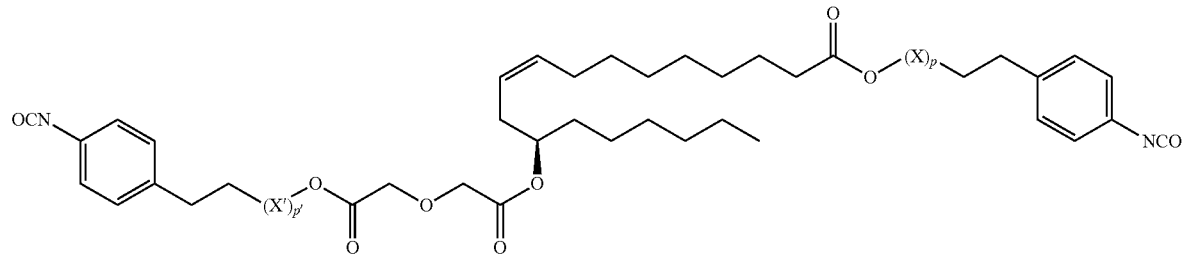
(11)
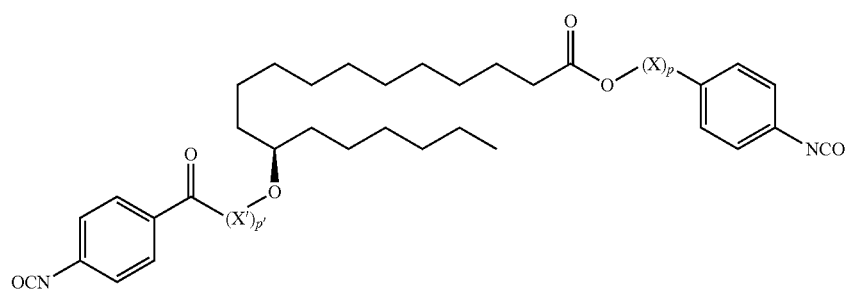
(12)
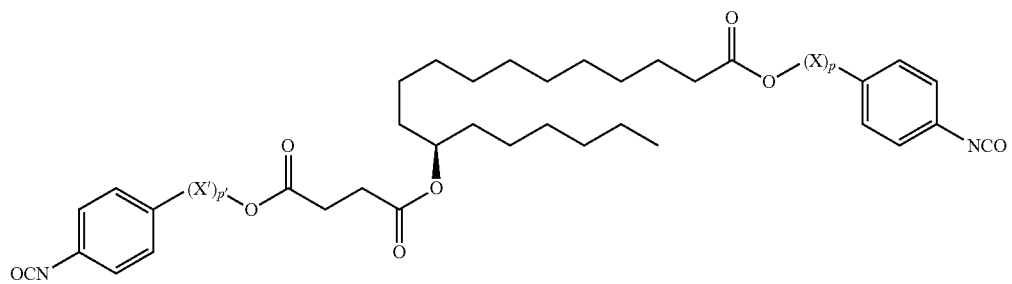
(13)
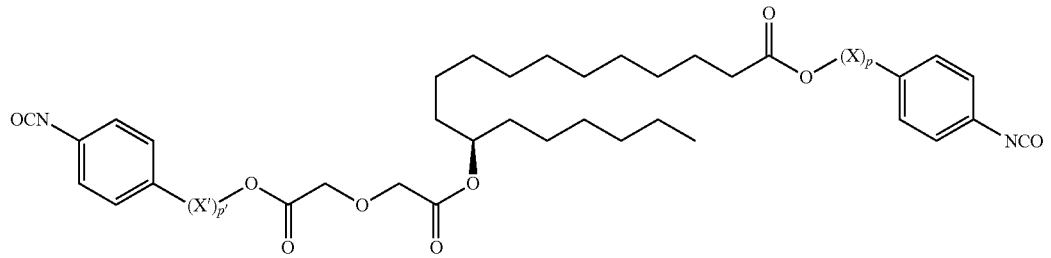
(14)
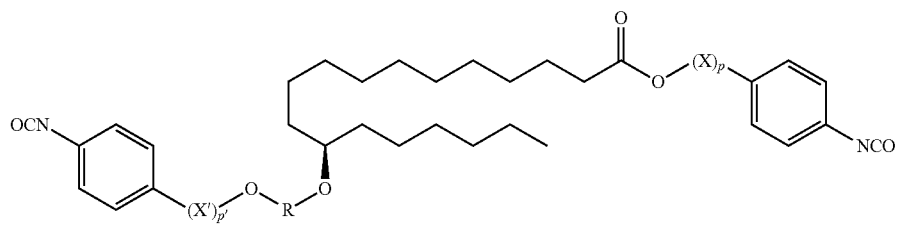
(15)
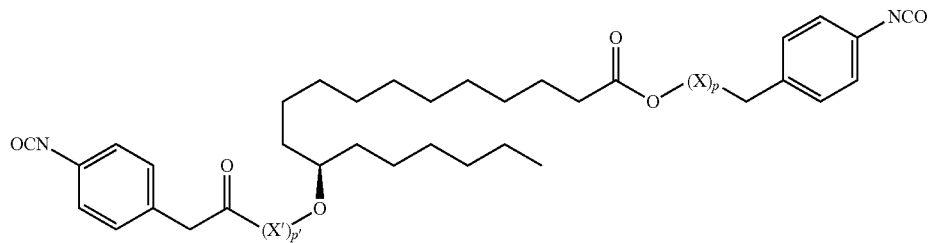

-continued

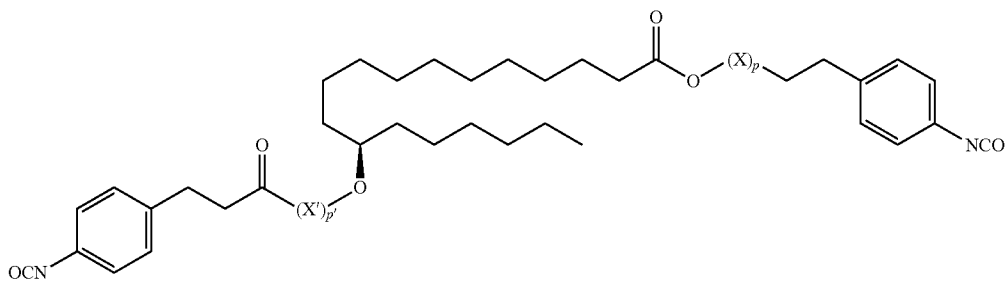

(16)

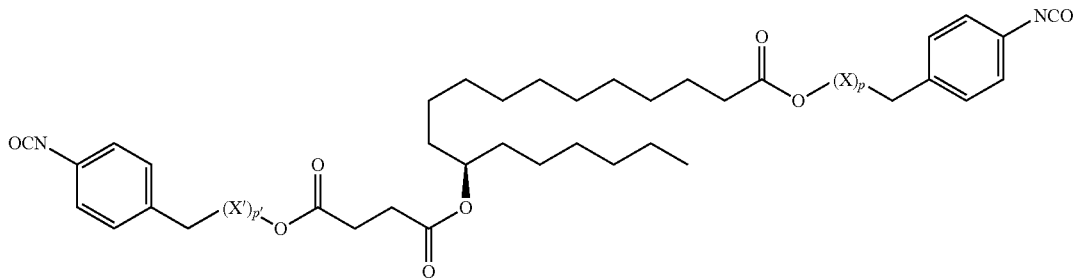

(17)

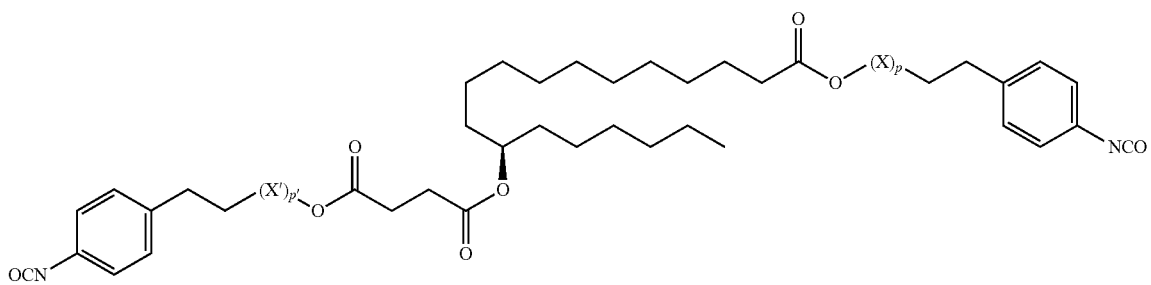

(18)

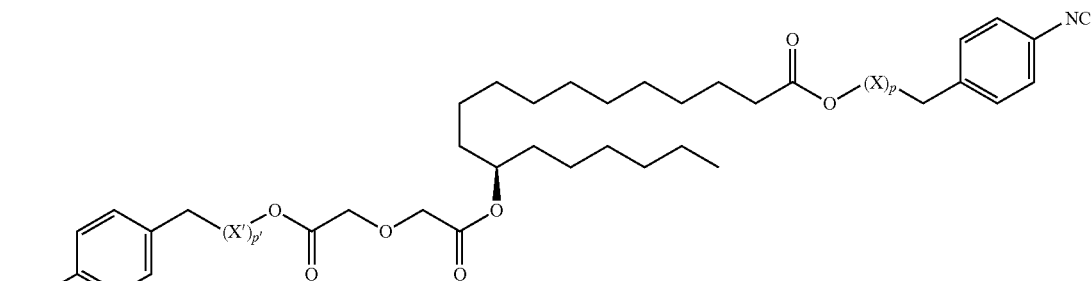

(19)

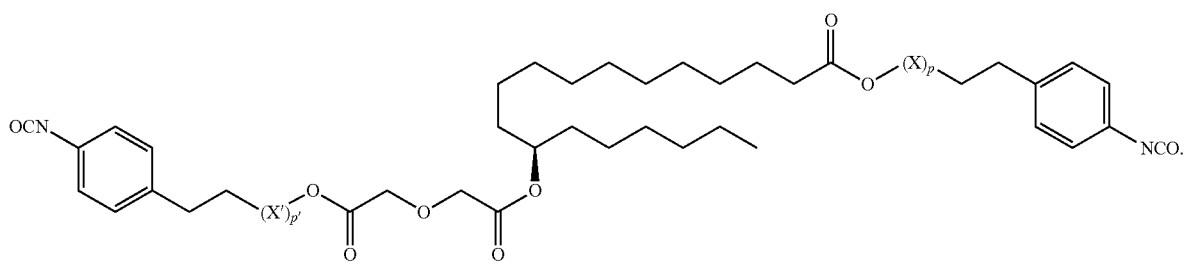

(20)

In another embodiment, the present invention provides a novel diisocyanate selected from formulae (1)A-(20)A, which correspond to diisocyanates (1)-(20) except that each phenyl ring of (1)A-(22)A is independently substituted with 1-4 $R_n$ and provided that at least one $R_n$ is other than H.

In another embodiment, the present invention provides a novel diisocyanate as described above, wherein:

each X independently is selected from the group consisting of:

—$CH_2COO$— (glycolic acid moiety);
—$CH(CH_3)COO$— (lactic acid moiety);

—CH₂CH₂OCH₂COO— (dioxanone moiety); and,
—CH₂CH₂CH₂CH₂CH₂COO— (caprolactone moiety);
each X' independently is selected from the group consisting of:
—OCH₂CO— (glycolic acid moiety);
—OCH(CH₃)CO— (lactic acid moiety);
—OCH₂CH₂OCH₂CO— (dioxanone moiety); and,
—OCH₂CH₂CH₂CH₂CH₂CO— (caprolactone moiety);
and,
provided that p+p' total from 2-6.

In another embodiment, the present invention provides a novel diisocyanate as described above, wherein:
each p is independently selected from 0, 1, 2, 3, and 4; and,
each p' is independently selected from 0, 1, 2, 3, and 4;
provided that p+p' total from 2-4.

In another embodiment, the present invention provides a novel polymer, comprising: a polyurethane, polyester-urethane, polyurea-urethane, or polyurea, formed by polymerizing at least one diisocyanate as described above with a compound selected from a diol, an ester-diol, diamide-diol and a diamine.

In another embodiment, the present invention provides a novel polymer as described above, wherein:

—CH₂CH₂OCH₂COO— (dioxanone moiety); and,
—CH₂CH₂CH₂CH₂CH₂COO— (caprolactone moiety);
each X' independently is selected from the group consisting of:
—OCH₂CO— (glycolic acid moiety);
—OCH(CH₃)CO— (lactic acid moiety);
—OCH₂CH₂OCH₂CO— (dioxanone moiety); and,
—OCH₂CH₂CH₂CH₂CH₂CO— (caprolactone moiety); and,
provided that p+p' total from 2-6.

In another embodiment, the present invention provides a novel polymer as described above, wherein:
each p is independently selected from 0, 1, 2, 3, and 4; and,
each p' is independently selected from 0, 1, 2, 3, and 4;
provided that p+p' total from 2-4.

In another embodiment, the present invention provides a novel polymer as described above, wherein: the polymer is a bioabsorbable polymer.

In another embodiment, the present invention provides a novel diamine selected from formula (IV), (V), or (VI):

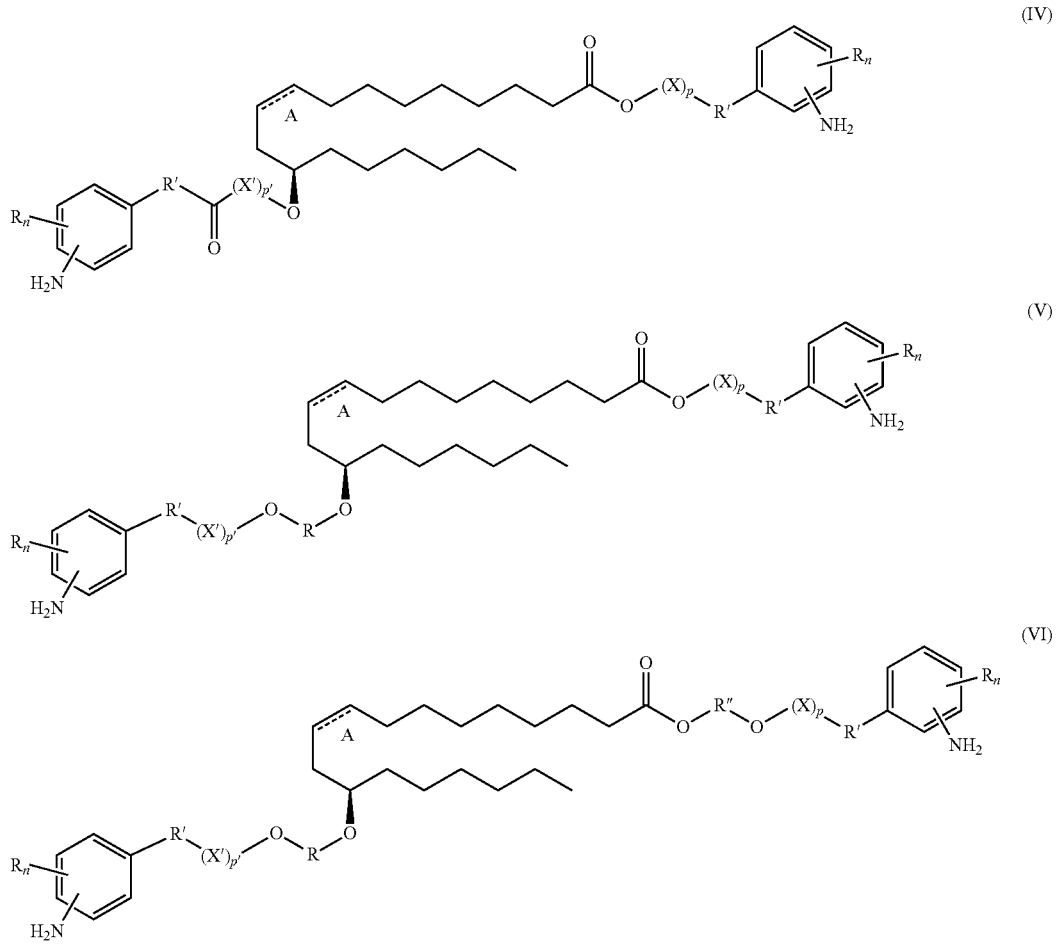

wherein:
variable A, the dashed bond, is absent or is a double bond;
R is independently the diacyl residue of a diacid;
R' is absent or each R' is independently a C₁₋₆ alkylene group;

each X independently is selected from the group consisting of:
—CH₂COO— (glycolic acid moiety);
—CH(CH₃)COO— (lactic acid moiety);

R″ is the residue of a diol or polyol;
from 1-4 $R_n$ are present;
each $R_n$ is independently selected from: H, $C_{1-6}$ alkyl, $C_{1-6}$ alkoxy, benzyloxy, halogen, —CHO, —$CO_2H$, and —$NO_2$, and each $R_n$ is independently attached directly to aromatic ring or attached through a —$(CH_2)_{1-4}$— linker;
each X independently is selected from:
—$CH_2COO$— (glycolic acid moiety);
—$CH(CH_3)COO$— (lactic acid moiety);
—$CH_2CH_2OCH_2COO$— (dioxanone moiety);
—$CH_2CH_2CH_2CH_2CH_2COO$— (caprolactone moiety);
—$(CH_2)_yCOO$— where y is selected from 2, 3, 4, and 6-24; and
—$(CH_2CH_2O)_zCH_2COO$— where z is selected from 2-24;

each X′ independently is selected from:
—$OCH_2CO$— (glycolic acid moiety);
—$OCH(CH_3)CO$— (lactic acid moiety);
—$OCH_2CH_2OCH_2CO$— (dioxanone moiety);
—$OCH_2CH_2CH_2CH_2CH_2CO$— (caprolactone moiety);
—$O(CH_2)_yCO$— where y is selected from 2, 3, 4, and 6-24; and,
—$O(CH_2CH_2O)_zCH_2CO$— where z is selected from 2-24;
each p is independently selected from 0, 1, 2, 3, 4, 5, and 6; and,
each p′ is independently selected from 0, 1, 2, 3, 4, 5, and 6;
provided that p+p′ total from 0 to 12.

In another embodiment, the present invention provides a novel diamine selected from formulae (IVa)-(VIa):

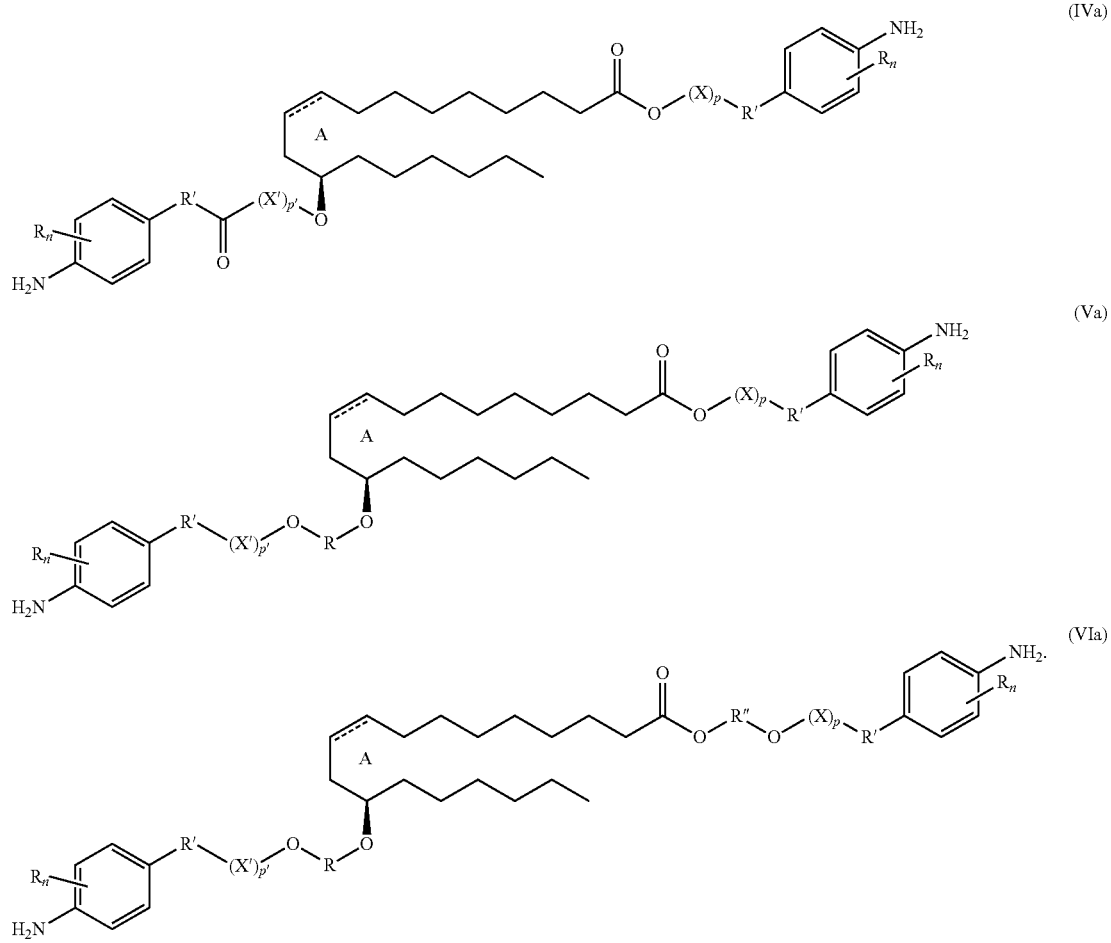

In another embodiment, the present invention provides a novel diamine selected from formulae ($IVa_1$)-($VIa_2$):

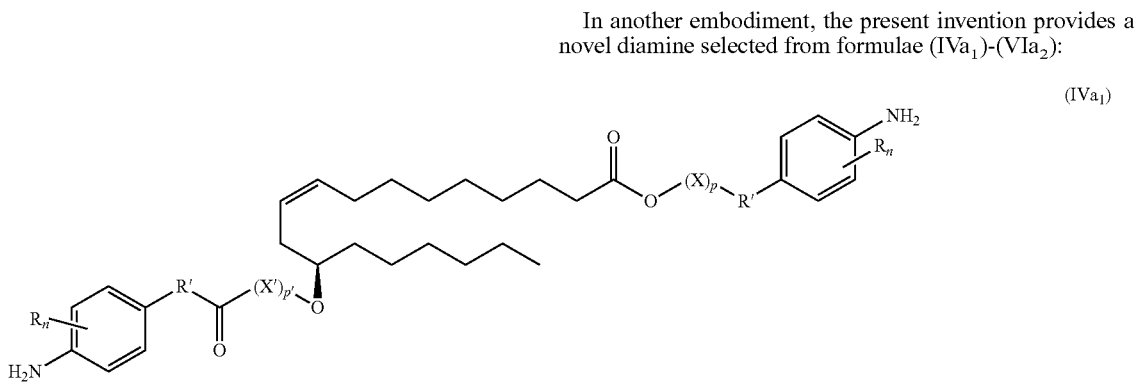

-continued
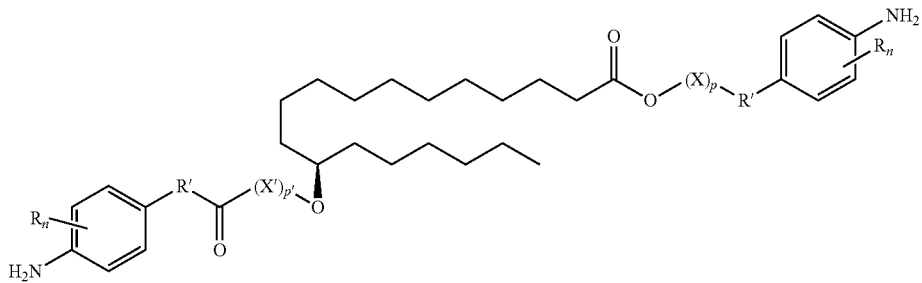
(IVa₂)
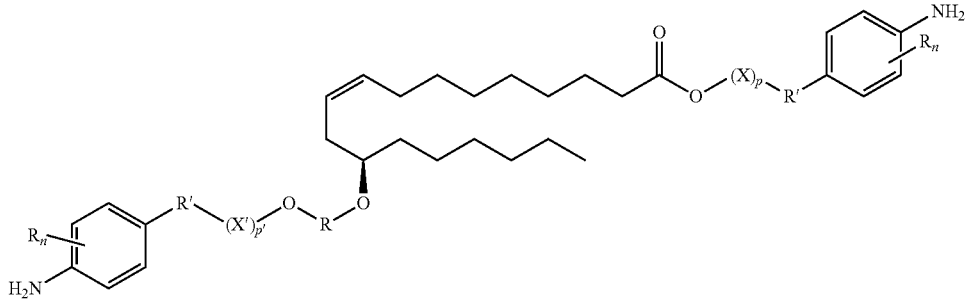
(Va₁)
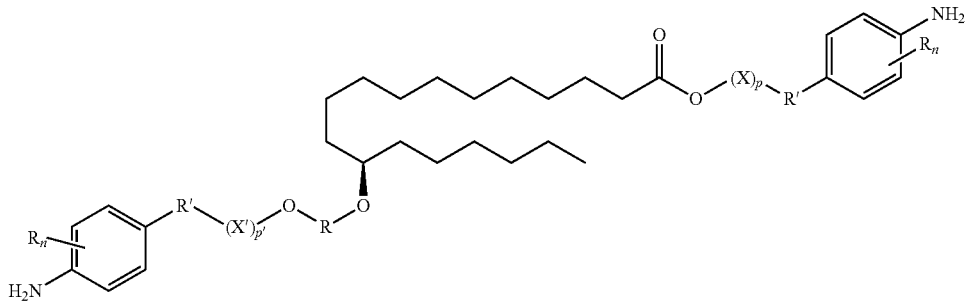
(Va₂)
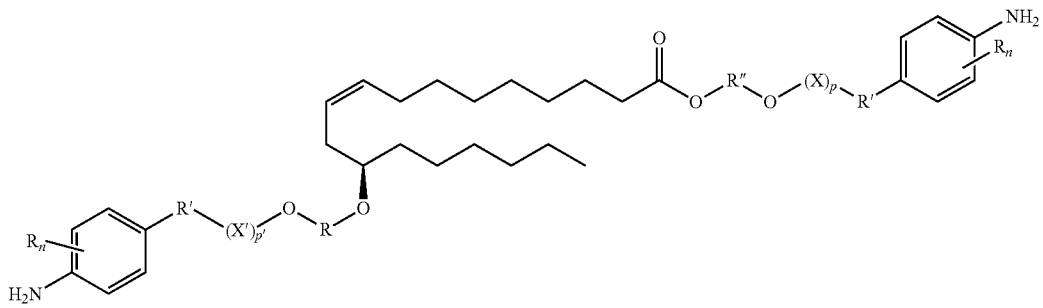
(VIa₁)
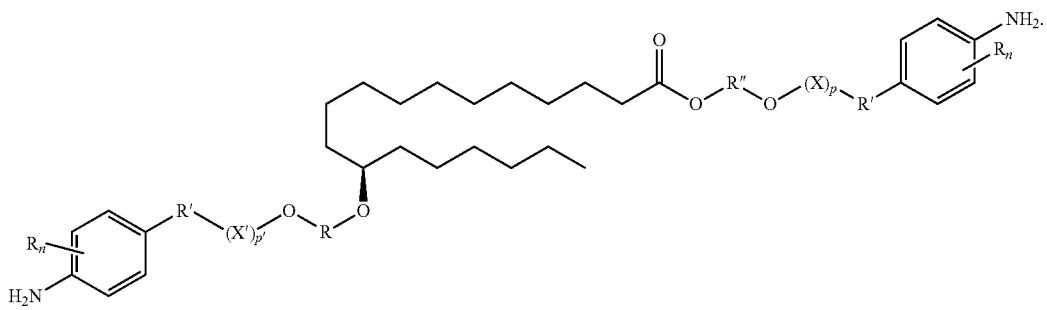
(VIa₂)

In another embodiment, the present invention provides a novel diamine selected from formulae (IVa$_{1A}$)-(VIa$_{2A}$):
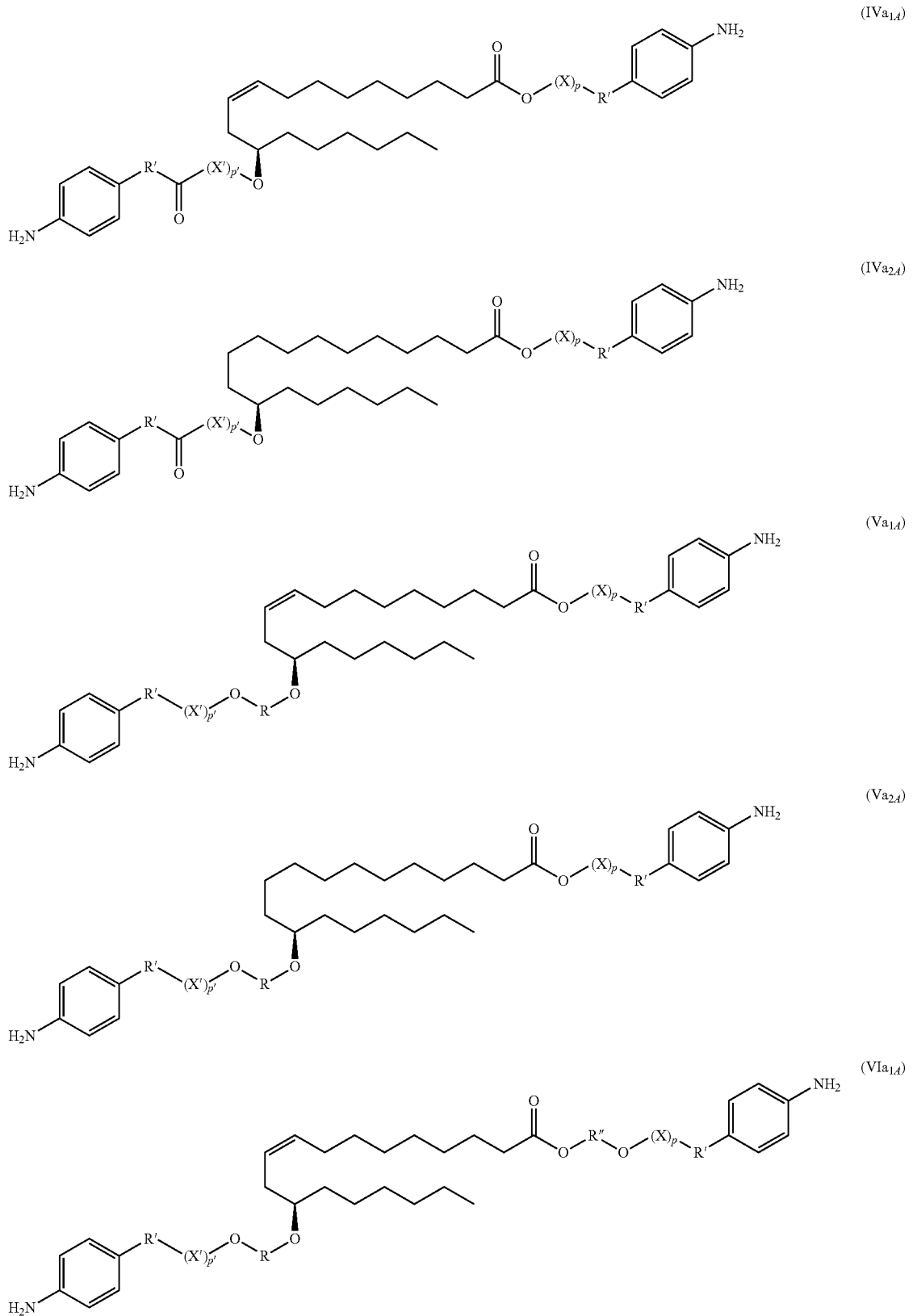

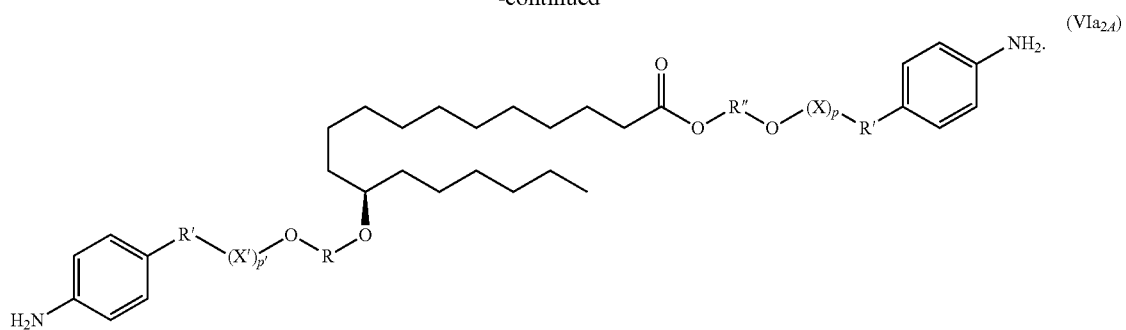
(VIa2A)
In another embodiment, the present invention provides a novel diamine selected from formulae (21)-(40):
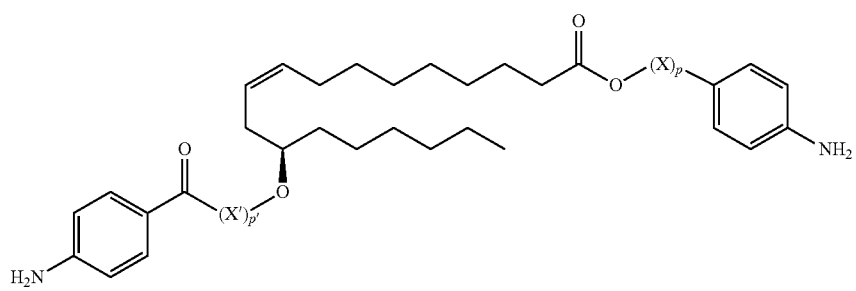
21
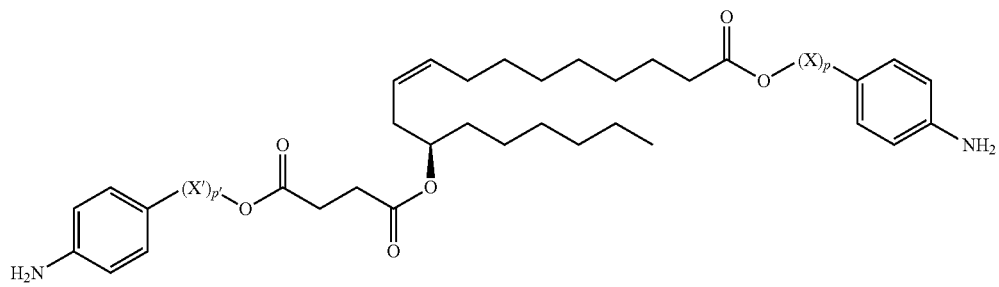
22
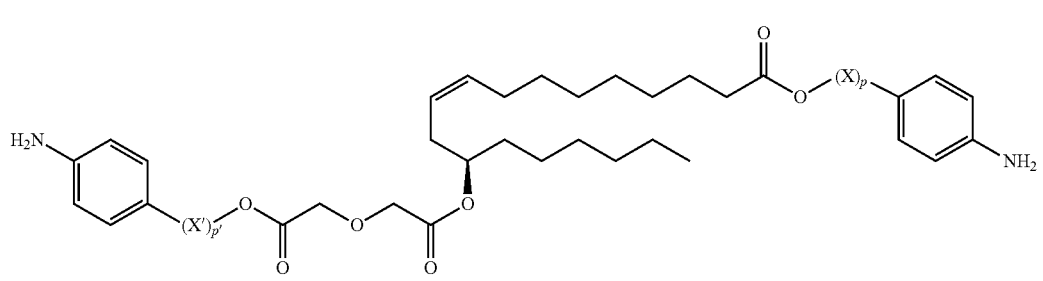
23
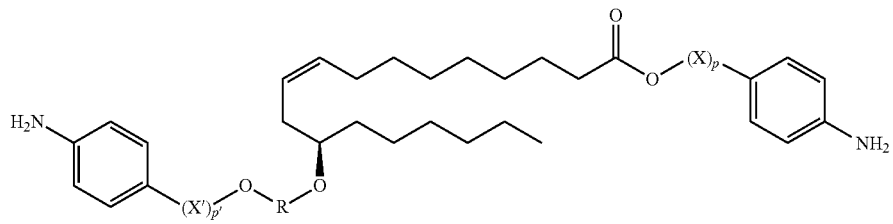
24

-continued
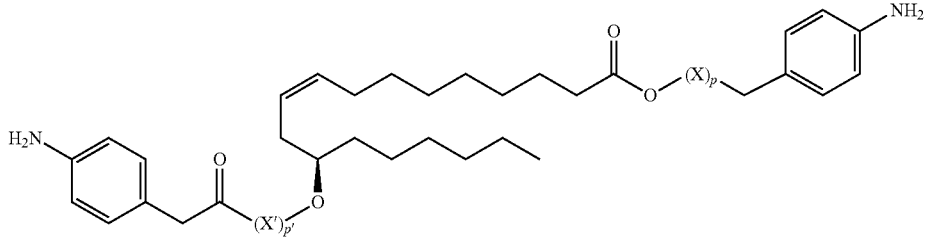
25
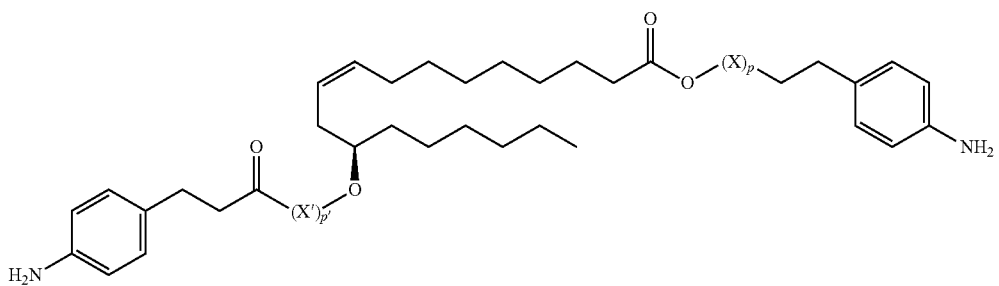
26
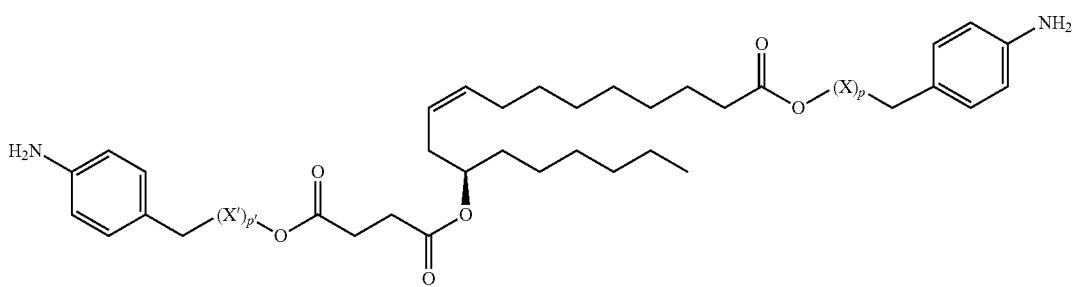
27
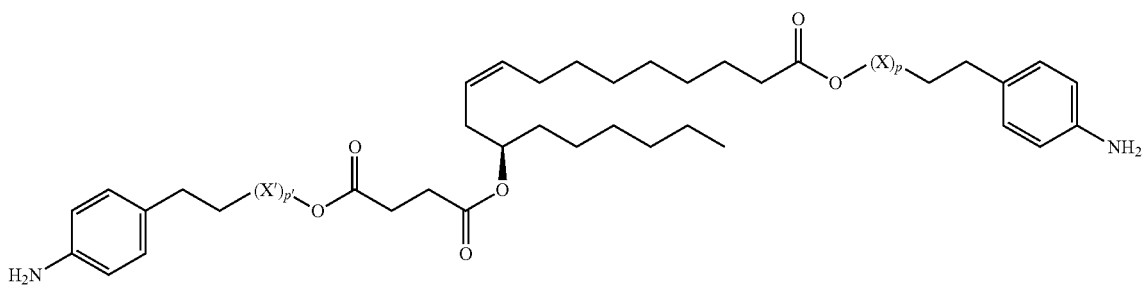
28
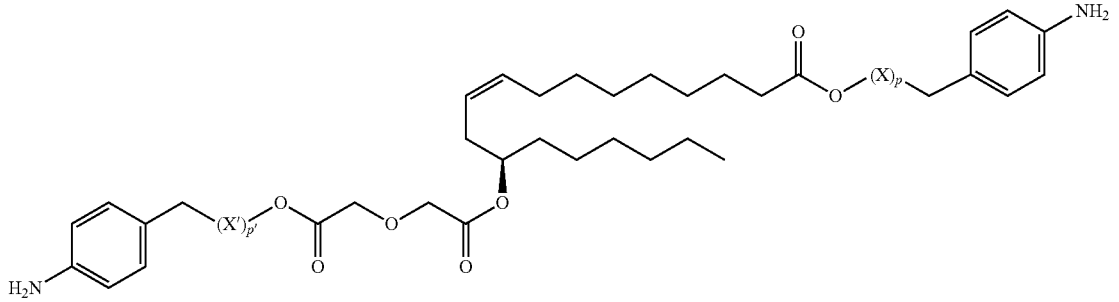
29

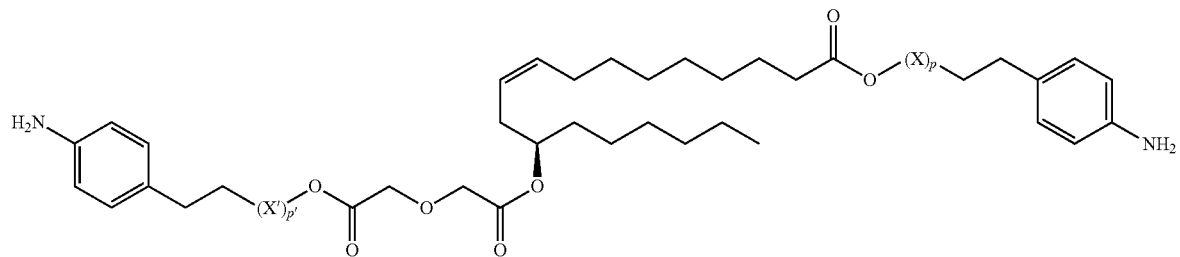
30
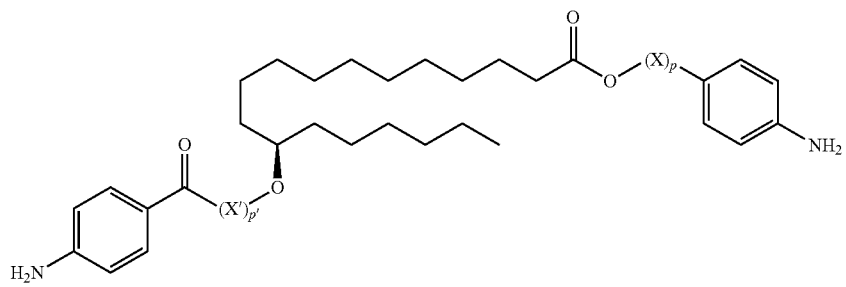
31
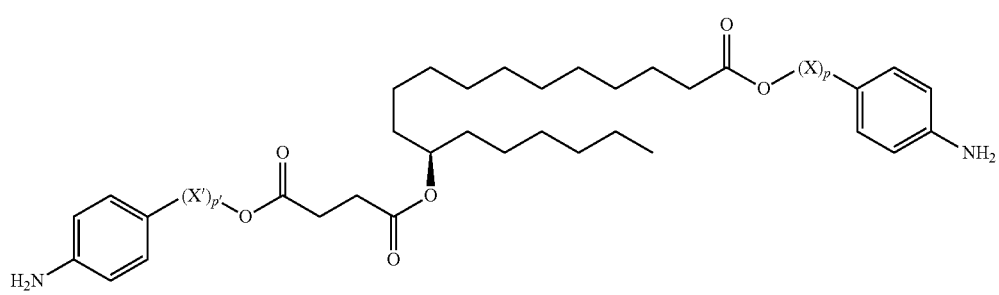
32
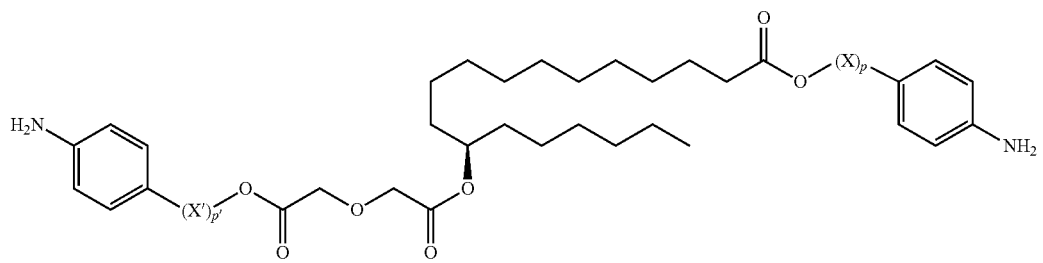
33
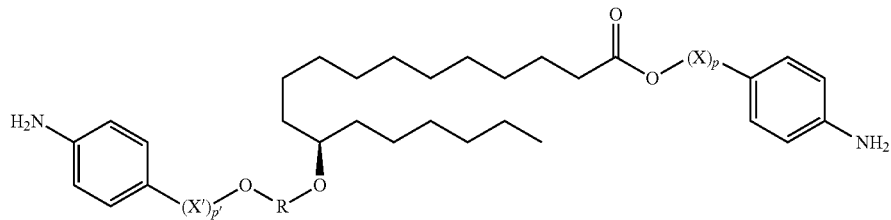
34
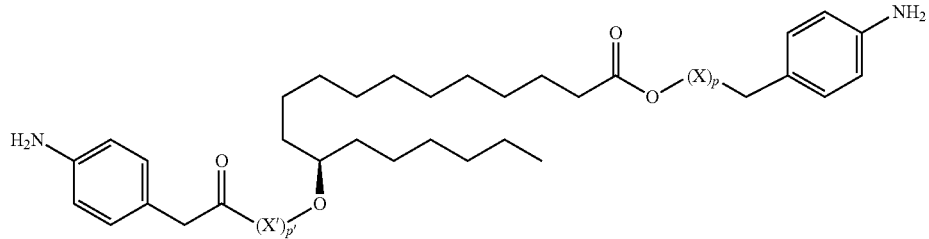
35

-continued
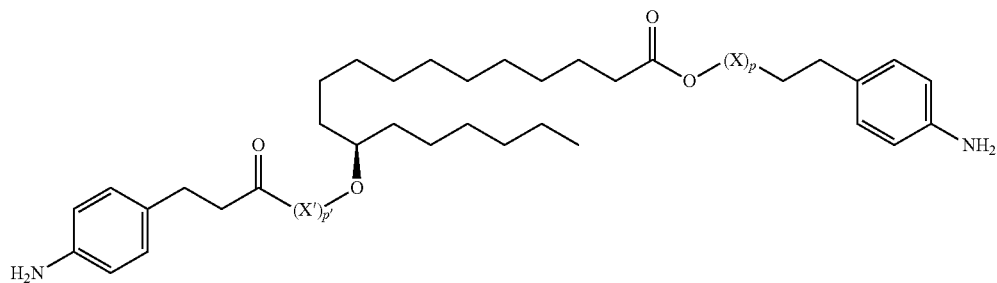
36
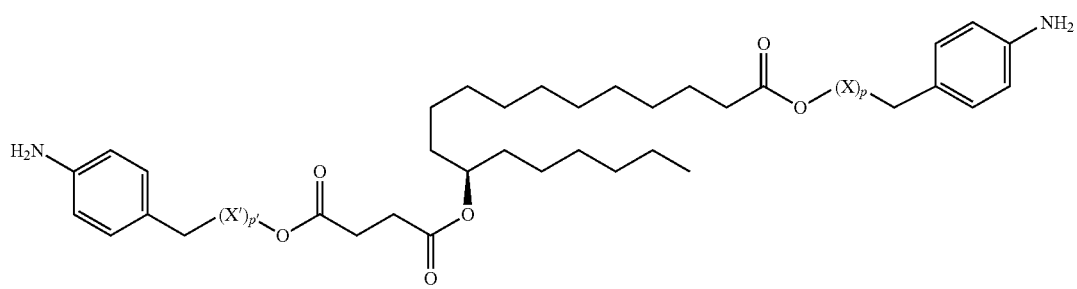
37
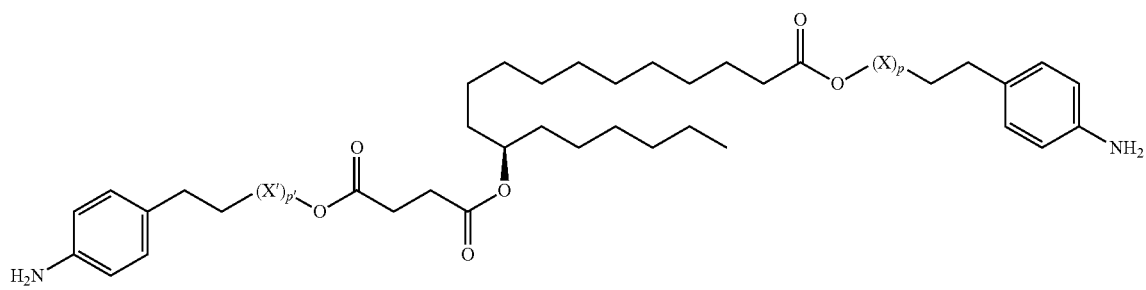
38
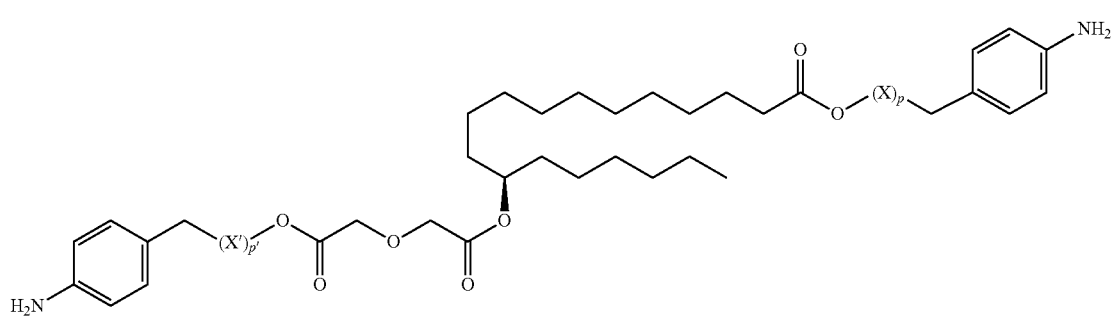
39
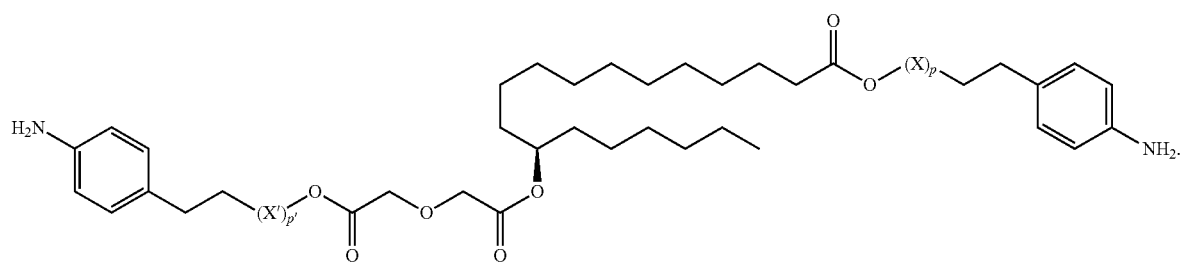
40

In another embodiment, the present invention provides a novel diamine selected from formulae (21)A-(40)A, which correspond to diamines (21)-(40) except that each phenyl ring of (21)A-(40)A is independently substituted with 1-4 $R_n$ and provided that at least one $R_n$ is other than H.

In another embodiment, the present invention provides a novel diamine as described above, wherein:
each X independently is selected from the group consisting of:
—CH$_2$COO— (glycolic acid moiety);
—CH(CH$_3$)COO— (lactic acid moiety);
—CH$_2$CH$_2$OCH$_2$COO— (dioxanone moiety); and,
—CH$_2$CH$_2$CH$_2$CH$_2$CH$_2$COO— (caprolactone moiety);
each X' independently is selected from the group consisting of:
—OCH$_2$CO— (glycolic acid moiety);
—OCH(CH$_3$)CO— (lactic acid moiety);
—OCH$_2$CH$_2$OCH$_2$CO— (dioxanone moiety); and,
—OCH$_2$CH$_2$CH$_2$CH$_2$CH$_2$CO— (caprolactone moiety); and,
provided that p+p' total from 2-6.

In another embodiment, the present invention provides a novel diamine as described above, wherein:
each p is independently selected from 0, 1, 2, 3, and 4; and,
each p' is independently selected from 0, 1, 2, 3, and 4;
provided that p+p' total from 2-4.

In another embodiment, the present invention provides a novel polymer, comprising: polyamide, polyester amide, polyepoxide, or polyurea formed by polymerizing at least one diamine as described above with a compound selected from a dicarboxylic acid, diepoxide, and diisocyanate.

In another embodiment, the present invention provides a novel polymer as described above, wherein:
each X independently is selected from the group consisting of:
—CH$_2$COO— (glycolic acid moiety);
—CH(CH$_3$)COO— (lactic acid moiety);
—CH$_2$CH$_2$OCH$_2$COO— (dioxanone moiety); and,
—CH$_2$CH$_2$CH$_2$CH$_2$CH$_2$COO— (caprolactone moiety);
each X' independently is selected from the group consisting of:
—OCH$_2$CO— (glycolic acid moiety);
—OCH(CH$_3$)CO— (lactic acid moiety);
—OCH$_2$CH$_2$OCH$_2$CO— (dioxanone moiety); and,
—OCH$_2$CH$_2$CH$_2$CH$_2$CH$_2$CO— (caprolactone moiety); and,
provided that p+p' total from 2-6.

In another embodiment, the present invention provides a novel polymer as described above, wherein:
each p is independently selected from 0, 1, 2, 3, and 4; and,
each p' is independently selected from 0, 1, 2, 3, and 4;
provided that p+p' total from 2-4.

In another embodiment, the present invention provides a novel polymer as described above, wherein: the polymer is a bioabsorbable polymer.

In another embodiment, the present invention provides a novel controlled drug delivery system comprising:
(a) one or more of the polymers described above, and
(b) one or more biologically or pharmacologically active agents.

In another embodiment, the present invention provides a novel controlled drug delivery system described above, wherein the one or more biologically or pharmacologically active agents are physically embedded or dispersed in a polymeric matrix, comprising: the one or more polymers.

In another embodiment, the present invention provides a novel tissue scaffold, comprising: one or more polymers described above, wherein the tissue scaffold has a porous structure for the attachment and proliferation of cells either in vitro or in vivo.

In another embodiment, the polymer is further polymerized on at least one end with at least one lactone monomer selected from the group consisting of glycolide, lactide, caprolactone, p-dioxanone, TMC, δ-valerolactone, β-butyrolactone, morpholinedione, pivalolactone, ε-decalactone, 2,5-diketomorpholine and combinations thereof in order to control physical and biological properties.

In another embodiment, the present invention provides a novel article, comprising: a metal or polymeric substrate and further comprising: at least one polymer described above, wherein said article is selected from:
a medical device, an implantable medical device, a pharmaceutical delivery system, a consumer product including durable articles, a cosmetic, a tissue engineering application, a foam, a reticulated foam, a suture, a bone hemostat, a bone filler, a bone void filler, a bone cement, a tissue adhesive, a tissue sealant, an adhesion prevention barrier, a mesh, a filter, a stent, a medical device coating, a pharmaceutical drug formulation, a cosmetic packaging, a pharmaceutical packaging, an apparel, an infusion device, a blood collection device, a skin care product, and a transdermal drug delivery material, drug delivery matrices, pharmaceutical drug formulations, tissue engineering, tissue adhesives, adhesion prevention barriers, and other implantable medical devices including foams for wound healing and/or drug delivery, bone hemostats, bone fillers, bone void fillers, bone wax formulations, tissue adhesives and sealants, adhesion prevention barriers, meshes, filters, surgical devices, medical device coatings, cosmetic and pharmaceutical packaging, apparel, infusion devices, blood collection tubes and devices, tubes, skin care products, transdermal drug delivery, consumer product packaging, and disposable medical devices, knitted products, foodstuffs, nutritional supplements, nutraceuticals, biodegradable chewing gums, and reinforced composites.

In another embodiment, the metal or polymeric substrate has a coating, comprising: the at least one polymer, wherein said article is suitable for contacting mammalian tissue.

In another embodiment, the article is an implantable medical device.

In another embodiment, the article is reticulated foam for wound healing and/or controlled drug delivery.

In another embodiment, the present invention provides a novel surgical article or component thereof or polymeric carrier, comprising: a polymer described above, wherein the article is selected from:
a stent, stent coating, wound covering, burn covering, foam, highly porous foams, reticulated foams, tissue engineering scaffold, film, adhesion prevention barrier, implantable medical device, controlled drug delivery system, suture, ligature, needle and suture combination, surgical clip, surgical staple, surgical prosthesis, textile structure, coupling, tube, support, screw, pin, bone wax formulation or an adhesion prevention barrier.

In another embodiment, the present invention provides a novel surgical article or component thereof as described above, wherein a biologically active agent is physically embedded or dispersed into the polymer matrix of the controlled delivery system.

In another embodiment, the present invention provides methods of making novel bio-based materials.

In another embodiment, the present invention provides novel bio-based castor oil or soybean oil derived hydroxyl acids diacids, diamines, and diisocyanates and polymers formed therefrom that include bio-based polyamides, polyureas, polyepoxides, polyester amides, and polyurethanes. These polymers can be biodegradable or biostable.

In another embodiment, the present invention provides novel bioabsorbable and biodegradable polyamides containing repeating units based on the novel aromatic di-amine monomeric units of the present invention. Methods for preparing the novel biodegradable and biocompatible polyamides are also provided.

In another embodiment, the present invention provides novel biodegradable and biocompatible polymers having a controllable degradation profile. These polymers are useful for medicinal and therapeutic uses, such as tissue engineering.

In another embodiment, the present invention provides novel aromatic diisocyanates.

In another embodiment, the present invention provides novel absorbable and/or biodegradable polyurethanes and polyurethane esters containing repeating units based on the novel aromatic diisocyanates of the present invention. Methods for preparing the novel biodegradable and biocompatible polyurethanes and polyurethane esters are also provided.

In another embodiment, the present invention provides novel bio-based novel biodegradable and biostable aliphatic polyester polyols.

In another embodiment, the present invention provides novel biobased and/or biodegradable, biocompatible and absorbable a polyurethane and polyurethane esters containing repeating units based on the novel diisocyanate-containing monomeric units of the present invention. The diisocyanates used to prepare polyurethanes and polyurethane esters can also be aliphatic or cycloaliphatic. Methods for preparing such biobased and/or biodegradable and absorbable aliphatic and aromatic polyurethanes and polyurethane esters are also provided.

In another embodiment, the novel diisocyanates, diamines, biodegradable and biocompatible polyurethanes, and biodegradable and biocompatible polyamides of the present invention can be used in combination with those described in patents/patent publications U.S. Pat. No. 7,772,352, U.S. Pat. No. 8,048,980, U.S. Pat. No. 8,143,325, U.S. Pat. No. 8,367,747, US 2010/0260702 A1, US 2009/0292029 A1, US 2009/0082540, US 2006/0288547 A1, EP 1937182 B1, EP 2298235 A1, EP 1937182 A4, EP 1937182 A2, and WO 27030464 A2, all of which have been assigned to Bezwada Biomedical (Bezwada Biomedical Patents), and U.S. Pat. No. 4,829,099 assigned to Fuller, et al., for use drug delivery matrices (e.g., controlled drug delivery), pharmaceutical drug formulations, tissue engineering, tissue adhesives, adhesion prevention barriers, and other implantable medical devices including but not limited to tissue engineering scaffolds, foams (including reticulated foams, lyophilized foams, highly porous foams, regular foams, foams with vertical channels, architecturally gradient foams, trans-compositional foams, and trans-structural foams) for wound healing and/or drug delivery, bone hemostats, bone fillers, bone void fillers, bone wax formulations, tissue adhesives and sealants, adhesion prevention barriers, meshes, filters, surgical devices (e.g., stents, staples, sutures (e.g., monofilament and multifilament sutures), screws (e.g., orthopedic screws), sheets, plates, clips, films, staples, pins, tubes, and molded devices), medical device coatings (e.g., stent coatings), cosmetic and pharmaceutical packaging (e.g., blister packaging films, cast films, extruded films and containers), apparels, infusion devices, blood collection tubes and devices, tubes, skin care products, transdermal drug delivery, consumer product packaging, and disposable medical devices.

In another embodiment, in the synthesis of a diisocyanate described in the above Bezwada Biomedical Patents, the 4-nitrophenol (ortho, meta, para) can be replaced by 4-$NO_2$-phenyl-$CH_2OH$ and/or 4-$NO_2$-phenyl-$CH_2CH_2OH$. Similarly, the 4-nitrobenzoic acid (ortho, meta, para) can be replaced by 4-$NO_2$-phenyl-$CH_2CO_2H$ and/or 4-$NO_2$-phenyl-$CH_2CH_2CO_2H$. Alternatively, the 4-nitrophenol can be replaced or substituted with 4-$NO_2$-(aromatic ring)-P—OH and 4-$NO_2$-(aromatic ring)-P—OH. Similarly, the 4-nitrobenzoic acid can be replaced or substituted with 4-$NO_2$-(aromatic ring)-P—$CO_2H$ and 4-$NO_2$-(aromatic ring)-P—$CO_2H$ wherein the aromatic rings can be monocyclic, bicyclic or polycyclic. The aromatic rings can also be fused. The aromatic rings can also be heterocyclic containing non-carbon ring atoms such as oxygen, nitrogen and sulfur. P is selected from an alkylene, alkylene-arylene, and an alicyclic chain. Further, the present invention also provides hydrolysable diisocyanates derived from these molecules further functionalized with one or more groups selected from glycolic acid, lactic acid, caprolactone, and a p-dioxanone moiety. The positions of nitro to hydroxyl or carboxyl can be ortho meta or para on the aromatic ring. The present invention also provides absorbable polyurethanes derived from the above diisocyanates.

In another embodiment, the present invention provides absorbable polyurethane foams with open and closed cell structures, including reticulated foams, foams with vertical channels, architecturally gradient foams, trans-compositional foams, and trans-structural foams and the process of preparing these absorbable foams using the novel hydrolysable diisocyanates, diamines, biodegradable and biocompatible polyurethanes described herein. Optionally the novel hydrolysable diisocyanates, diamines, biodegradable and biocompatible polyurethanes described herein are used in combination with those described in patents/patent publications U.S. Pat. No. 7,772,352, U.S. Pat. No. 8,048,980, U.S. Pat. No. 8,143,325, U.S. Pat. No. 8,367,747, US 2010/0260702 A1, US 2009/0292029 A1, US 2009/0082540, US 2006/0288547 A1, EP 1937182 B1, EP 2298235 A1, EP 1937182 A4, EP 1937182 A2, and WO 27030464 A2, all of which have been assigned to Bezwada Biomedical, and U.S. Pat. No. 4,829,099, assigned to Fuller, et al., via lyophilization wherein the bioabsorbable polyurethane polymers and/or blends thereof are dissolved in a suitable solvent including dioxane, N-methylpyrrolidone, dichloromethane and/or mixtures thereof, to form a homogeneous solution which is subjected to a lyophilization process, comprising: a solution of a bioabsorbable elastomer in a solvent which is substantially, but not necessarily completely, solidified, then the solvent is removed from that which is lyophilized under reduced pressure to form a foam.

In another embodiment, the novel diisocyanates of the present invention provide a true reticulated, flexible, and resilient, bioabsorbable elastomeric matrix, suitable for implantation and having sufficient porosity to encourage cellular ingrowth and proliferation in vivo.

In another embodiment, the present invention provides a polymerization process for preparing a bioabsorbable reticulated elastomeric matrix, comprising the steps of:

(1) admixing
  a) a polyol component,
  b) a diisocyanate component,
  c) a blowing agent,
  d) optionally, a crosslinking agent,
  e) optionally, a chain extender,
  f) optionally, one or more catalysts,
  g) optionally, one or more cell openers, h) optionally, a surfactant, and
i) optionally, a viscosity modifier;
to provide a crosslinked elastomeric matrix, and
(2) reticulating the elastomeric matrix by a reticulation process to provide the reticulated elastomeric matrix. The ingredients are present in quantities and the elastomeric matrix is prepared under conditions so as to: (i) provide a crosslinked resiliently-compressible absorbable elastomeric matrix, (ii) control formation of biologically undesirable residues, and (iii) reticulate the foam by a reticulation process, to provide the reticulated elastomeric matrix.

In another embodiment, the invention provides a lyophilization process for preparing a reticulated elastomeric matrix, comprising: lyophilizing a flowable polymeric material.

In another embodiment, the polymeric material, comprises: a solution of a solvent-soluble absorbable elastomer in a solvent.

In another embodiment, the flowable polymeric material is subjected to a lyophilization process, comprising: solidifying the flowable polymeric material to form a solid, e.g., by cooling a solution, then removing the non-polymeric material, e.g., by evaporating the solvent from the solid under reduced pressure, to provide an at least partially reticulated elastomeric matrix.

In another embodiment, a solution of a absorbable elastomer in a solvent is substantially, but not necessarily completely, solidified, then the solvent is evaporated from that material to provide an at least partially reticulated elastomeric matrix.

In another embodiment, the temperature to which the solution is cooled is below the freezing temperature of the solution.

In another embodiment, the temperature to which the solution is cooled is above the apparent glass transition temperature of the solid and below the freezing temperature of the solution.

In another embodiment, the present invention provides a lyophilization process for producing an elastomeric matrix having a reticulated structure, the process comprising the steps of:
  a) forming a solution comprising a solvent-soluble absorbable elastomer in a solvent;
  b) at least partially solidifying the solution to form a solid, optionally by cooling the solution; and
  c) removing the non-polymeric material, optionally by evaporating the solvent from the solid under reduced pressure, to provide an at least partially reticulated elastomeric matrix comprising the elastomer.

In another embodiment, the invention provides a process for preparing a reticulated composite elastomeric implantable device for implantation into a patient, the process comprising: surface coating or endoporously coating a absorbable reticulated elastomeric matrix with a coating material selected to encourage cellular ingrowth and proliferation. The coating material can, for example, comprise: a foamed coating of absorbable polyurethane and optionally, collagen, fibronectin, elastin, hyaluronic acid or a mixture thereof. Alternatively, the coating comprises: absorbable polyurethane and an inorganic component (e.g., calcium carbonate, tricalcium phosphate, magnesium carbonate, as well as other inorganic salts).

In another embodiment, the invention provides novel, safe, bio-based, biocompatible and absorbable aromatic diisocyanate-based adhesives. For example, such adhesives are metabolically-acceptable surgical adhesives and have controllable degradation profiles. In another embodiment, the invention provides methods for closing wounds in living tissue by use of novel, metabolically-acceptable surgical adhesives having low toxicity.

In another embodiment, the invention provides diamines that can provide hydrophilic bioabsorbable polyester amides that are biocompatible and useful for bioabsorbable sutures, staples clips, and adhesion prevention barriers.

In another embodiment, the invention provides novel polyurethanes, polyesters, and polyester amides that are biodegradable and biocompatible and useful for tissue engineering, drug delivery, tissue adhesives, adhesion prevention, and other implantable medical devices.

In another embodiment, the invention provides novel hydrolysable diisocyanates for use in the formation of polyurethanes and other polymers.

In another embodiment, the invention provides novel hydrolysable branched diisocyanates with pendant long chain alkyl groups that are hydrophobic or pendant long chain PEG that are hydrophilic.

In another embodiment, the invention provides novel bioabsorbable polyesters, polyurethanes, polyureas, and polyester amides that can be further polymerized with lactone monomers. Examples of lactone monomers include glycolide, lactide, caprolactone, p-dioxanone, TMC (trimethylene carbonate), δ-valerolactone, β-butyrolactone, morpholinedione, pivalolactone, ε-decalactone, 2,5-diketomorpholine, and combinations thereof. These lactone monomers allow one to control physical and biological properties.

As noted above, the bio-based monomers of the present invention, which have at least two reactive sites, can be polymerized with difunctional molecules (e.g., dialcohols (diols), ester-diols, diamide-diols, diamines, dicarboxylic acids (diacids), diexopides, and diisocyanates) to form polymers of the present invention, including polyurethanes, polyester-urethanes, polyurea-urethanes, polyureas, polyamides, polyester amides, and polyepoxides by simple polycondensation reactions.

Examples of diols that can be used to form polymers with the bio-based monomers of the present invention have the following structure:

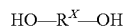

wherein $R^X$ is independently selected from: alkylene, cycloalkylene-alkylene, arylene-alkylene, arylene-alkylene-arylene, cycloalkylene-alkylene-cycloalkylene, and arylene-alkylene-cycloalkylene, wherein:
  (1) one or more of the methylene (—$CH_2$—) moieties in the alkylene chain portions of the $R^X$ group are optionally replaced by —O— or —S—; or
  (2) one or more of the ethylene (—$CH_2CH_2$—) moieties in the alkylene chain portions of the $R^X$ group are optionally replaced by a carboxyl group (—C(=O)O— or —OC(=O)—).

Alternatively, polyalkylene oxides having weight average molecular weights from about 500-10,000 can be used as a diol (i.e., a polydiol). Examples of suitable diols or polydiols for use in the present invention are diols with up to 8 carbon atoms or diols having repeating units each with up to 8 carbon atoms. Examples of suitable diols include 1,2-ethanediol (ethylene glycol); 1,2-propanediol (propylene glycol); 1,3-propanediol; 1,4-butanediol; 1,5-pentanediol; 1,3-cyclopentanediol; 1,6-hexanediol; 1,4-cyclohexanediol; 1,8-octanediol; and, combinations thereof. Examples of polydiols include polyethylene glycol and polypropylene glycol with weight average molecular weights of 500-10,000.

Examples of ester-diols that can be used to form polymers with the bio-based monomers of the present invention have the following structure:

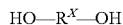

wherein $R^X$ is defined previously, provided that $R^X$ contains at least one internal carboxyl group (C(O)O).

Examples of diamide-diols that can be used to form polymers with the bio-based monomers of the present invention are have the following structure:

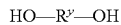

wherein $R^y=R^X$ as defined previously, provided that two or more of the ethylene (—CH$_2$CH$_2$—) moieties in the alkylene chain portions of the $R^X$ group are replaced by amide groups (C(O)NH or NHC(O)).

Examples of diamines that can be used to form polymers with the bio-based monomers of the present invention include have the following structure:

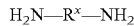

wherein $R^X$ is as defined previously. Alternatively, polyalkylene oxides that are diamines with weight average molecular weights from about 500-5,000 can be used.

Examples of dicarboxylic acids that can be used to form polymers with the bio-based monomers of the present invention have the following structure:

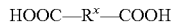

wherein $R^X$ is as defined previously.

Examples of diepoxides that can be used to form polymers with the bio-based monomers of the present invention have the following structure:

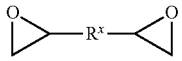

wherein $R^X$ is as defined previously.

Examples of diisocyanates that can be used to form polymers with the bio-based monomers of the present invention have the following structure:

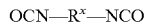

wherein $R^X$ is as defined previously. Other examples include hexamethylene diisocyante, lysine diisocyanate, methylene diphenyl diisocyanate (e.g., MDI), methylene dicyclohexyl diisocyanate, and isophorone diisocyanate.

In another embodiment, the present invention provides polymers from which a medical device or a component of the device is formed, and the polymers exhibit a percent elongation greater than about 200 or even greater than about 500. The polymers can also exhibit a modulus (Young's Modulus) of less than about 40,000 psi, or even less than about 20,000 psi. These properties, which measure the degree of elasticity of the bioabsorbable elastomer, are achieved while maintaining a tensile strength greater than about 500 psi, or even greater than about 1,000 psi, and a tear strength of greater than about 50 lbs/inch, or even greater than about 80 lbs/inch Generally the functionality of the aromatic monomers is selected from amine- and/or carboxylic acid-containing phenols, such as amino phenols and amino salicylic acids, and from amino benzoic acids, (4-aminophenyl)methanol, 2-(4-aminophenyl)ethanol, 2(4-aminophenyl)acetic acid, and 3-(4-aminophenyl)propionic acid as summarized below. Glycolic acid is used as a functionalization moiety for purposes of illustration.

The biological properties of the bioabsorbable polymers of the present invention used to form devices or parts thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

The materials (e.g., polymers) of the present invention comprise: cleavable sites (e.g., see the X group of the structures provided herein). Depending on the formation route selected, these cleavable sites may be regular along the length of a chain extender, thereby giving the segmented polyurethane or polyester or the like a biodegradability that is, by some measure, predictable.

Biodegradability is influenced by a number of factors, including crystallinity. The hydrophilicity of the polymer may also influence the degradability, that is, the extent to which water is accessible to the polymer matrix. The number of cleavage sites may also influence biodegradability. Generally speaking, the higher the number of cleavage sites, the greater the rate of degradation. Typically, the cleavable site is an ester site. For example, the cleavable ester site can be derived from a hydroxy acid precursor. This provides segmented polyurethanes and polyesters or the like with cleavable sites that may be arranged to be recognizable by enzymes.

The polyester amides of the present invention may be prepared by reacting an amide acid of the present invention with diols in the presence of an organometallic catalyst at elevated temperatures. The organometallic catalyst is typically a tin-based catalyst, e.g. stannous octoate, and is present in the monomer mixture at a mole ratio of monomer-to-catalyst ranging from 15,000 to 80,000/1. The polymerization is typically carried out at a temperature ranging from 120-200° C. or 160-190° C., until the desired molecular weight and viscosity are achieved.

The polyurethanes and other polymers of the present invention may be prepared by reacting the diisocyanates of the present invention with a branched chain extender or a chain extender and polyols of the present invention and/or generic polyols including polyethylene glycols, polyesterdiols, and polyetherdiols.

The polyamides of the present invention may be prepared by reacting diamines of the present invention with diacids of the present invention and/or generic diacids including polyethylene diacids, polyesterdiacids, and polyetherdiacids.

The polyepoxides of the present invention may be prepared by reacting diamines of the present invention with epoxides.

In another embodiment, the present invention provides monomers wherein the diisocyanate groups are replaced with isothiocyanates; and polymers produced therefrom. Specifically, this embodiment of the invention is directed to isothiocyanate analogs of the above.

In another embodiment, the present invention provides novel biodegradable and biocompatible aliphatic and cyclic aliphatic diisocyanate-based monomers. Examples of cyclic aliphatic diisocyanate-based monomers are the cyclohexane-containing compounds which are related to their aromatic counterparts formally by reduction of the benzene rings to cyclohexane rings. The polymers prepared from such saturated monomers have beneficially reduced color, improved transparency and are non-yellowing.

Examples of cyclic aliphatic diamine-based monomers are the cyclohexane-containing compounds, which are related to their aromatic counterparts 21-40 formed by reduction of the benzene rings to cyclohexane rings. As for the corresponding cycloaliphatic diisocyanate monomers, the polymers prepared from such saturated diamine monomers have beneficially reduced color, improved transparency and are non-yellowing.

A beneficial property of the polymers of the present invention that contain ester linkages is that the ester linkages are hydrolytically unstable, and therefore the polymer is absorbable because it readily breaks down into small segments when exposed to moist bodily tissue.

When any variable occurs more than one time in any constituent or in any formula, its definition in each occurrence is independent of its definition at every other occurrence. Combinations of substituents and/or variables are permissible only if such combinations result in stable compounds. Within the context of the present invention, compounds are stable if they do not degrade significantly prior to their intended use under normal conditions. In some instances, compounds of the invention may be designed or required to be bioabsorbed or biodegraded as part of their intended function. Absorbability and/or biodegradability, which may be an advantageous property of the present polymers, is not intended to mean that the polymeric compound are unstable.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form, except where such limit is clearly defined.

Precursors of the Compounds and Monomeric Units

Glycolic acid and lactic acid are known as alpha-hydroxy acids (AHAs) and are present in fruits and other foods. The chemical formula of glycolic acid is $HOCH_2COOH$. This compound is biodegradable. When glycolic acid is heated it readily loses water by self-esterification to form polyglycolic acid. Glycolic acid can function as both an acid and an alcohol. This dual functionality leads to a variety of chemical reactions and valuable physical properties. Many surgical devices are made from polyglycolic acid. The process of attaching a glycolic acid moiety to a phenolic compound is defined as glycolation.

Lactic acid is a fermentation product of lactose. It is present in sour milk, koumiss, leban, yogurt, and cottage cheese. Lactic acid is also produced in the muscles during intense activity. Many surgical and orthopedic devices are made from polylactic acid. The esters of lactic acid are useful as emulsifying agents in baking foods; examples include stearoyl-2-lactylate, glyceryl lactostearate, and glyceryl lactopalmitate. The process of attaching a lactic acid moiety to a phenolic compound is defined as lactolation.

Epsilon-caprolactone is a reactive cyclic monomer, and the polymers derived therefrom are useful for tailoring specialty polyols and hydroxy-functional polymer resins with enhanced flexibility. The monomer polymerizes under mild conditions to give low viscosity products superior to conventional aliphatic polyesters. Copolymers of caprolactone with glycolide and lactide exhibit unique physical and biological properties as well as different hydrolysis profiles based on the composition of the monomers. The process of attaching an open chain ε-caprolactone moiety to a phenolic compound is defined as caprolation.

p-Dioxanone (1,4-dioxan-2-one) is a cyclic monomer, and polymers are made therefrom via ring opening polymerization. Polyesters derived from this monomer are used in making bioabsorbable surgical devices with a longer absorption profile (slower hydrolysis) compared to polyglycolic acid. The bioabsorbable surgical devices made from 1,4-dioxan-2-one have proved to be biologically safe, and biocompatible. The process of attaching an open chain p-dioxanone moiety to a phenolic compound is defined as dioxonation.

Embodiments of the new functionalized bio-based diamines and diisocyanates have controllable hydrolysis profiles, improved bioavailability, improved efficacy, and enhanced functionality. The difunctional compounds of the present invention can readily polymerize into biodegradable polyamides, polyesters, polyureas, polyepoxides, polyesteramides and polyurethanes, which are useful for many applications that are described herein.

"Absorbable" refers to a monomer or product derived therefrom that readily reacts or enzymatically degrades upon exposure to bodily tissue for a relatively short period of time, thus providing a significant weight loss of the original material in that short time period. Examples of time periods include, up to 12 months, up to 9 months, 3-9 months, up to 6 months, and 2-8 weeks. Therefore, the polymers of the present invention can be fabricated into medical and surgical devices, foams, bioadhesives, coatings, etc., (described previously) that are useful for a vast array of applications requiring complete absorption within the relatively short time periods as defined above.

"Monomers" includes macromers, unless the context clearly indicates otherwise.

"Elastomer" is a material that at room temperature can be stretched repeatedly to at least twice its original length and, upon immediate release of the stress, will return with force to its approximate original length.

"Prepolymer" is a low molecular weight polymer usually an intermediate between that of the monomer and the final polymer that is capable of further polymerization.

"Monomeric unit" is defined as a small molecule that can chemically react with other monomers to form a polymer.

"Polymer" is a molecule that is formed by joining repeating monomeric units. The polymers of the present invention can be, without limitation, linear, branced, star or comb polymers.

A "biologically active" is a substance that can act on a cell, virus, organ, or organism, including but not limited to drugs (i.e., pharmaceuticals) to create a change in the functioning of the cell, virus, organ, or organism. In certain embodiments of the invention, the biologically active substances are organic molecules having molecular weight of about 600 or less, or are polymeric species such as proteins, nucleic acids, and the like. A biologically active substance can be a substance used for therapy of an animal, preferably a human. In the present invention, a biologically active substance bears, or has a functional homolog that bears, one or more hydroxyl, amino, and/or carboxylic acid substituents, including functional derivatives such as esters, amides, methyl ethers, glycosides, and other derivatives that are apparent to those skilled in the art. Examples of biologically active compounds that can be used in the present invention include Capsaicin, Vitamin E, Resveratrol, and isoflavonoids.

"Alkyl" refers to an optionally substituted, saturated straight, or branched hydrocarbon moiety having from 1-20 carbon atoms (and all combinations and subcombinations of ranges of carbon atoms and specific numbers of carbon atoms therein). Examples of ranges of carbon atoms include 1-8, 1-6, and 1-4. Examples include methyl, ethyl, n-propyl, iso-propyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

"Alkylene" refers to a bivalent alkyl moiety having the general formula —$(CH_2)_n$—, where n is from 1 to 150. Examples of carbon ranges include 1-20, 1-16, and 1-10. By bivalent, it is meant that the group has two open sites each of which bonds to another group. Examples include methylene, ethylene, trimethylene, pentamethylene, and hexamethylene. Alkylene groups can be optionally substituted with alkyl, wherein alkyl is as previously defined. "Lower alkylene" herein refers to those alkylene groups having from 1-6 carbon atoms.

"Aryl" refers to an optionally substituted, mono-, di-, tri-, or other multicyclic aromatic ring system moiety having from 6-50 carbon atoms (and all combinations and subcombinations of ranges of carbon atoms and specific numbers of carbon atoms therein). Examples of ranges of carbon atoms include 6-10. Examples include phenyl, naphthyl, anthracenyl, and phenanthrenyl.

"Arylene" refers to a bivalent aryl moiety, wherein aryl is as previously defined. The ring system may be monocyclic or fused polycyclic (e.g., bicyclic, tricyclic, etc.). An example is phneylene. In various embodiments, the arylene, e.g., phenylene, may be a 1,2-, 1,3-, or 1,4-substituted moiety.

"Cycloalkyl" refers to an optionally substituted, mono-, di-, tri-, or other multicyclic alicyclic ring system moiety having from 3-20 carbon atoms (and all combinations and subcombinations of ranges of carbon atoms and specific numbers of carbon atoms therein). Examples of carbon ranges include 3-8, and 3-6. Multi-ring structures may be bridged or fused ring structures, wherein the additional groups fused or bridged to the cycloalkyl ring may include optionally substituted cycloalkyl, aryl, heterocycloalkyl, or heteroaryl rings. Examples of cycloalkyl groups include cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

"Cycloalkylene" refers to a bivalent cycloalkyl moiety, wherein cycloalkyl is as previously defined. Cycloalkylene is a type of alkylene group which is a cycloalkyl group with two open bonding sites.

"Cycloalkylenealkylene" refers to a bivalent moiety, wherein a cycloalkylene group is bonded to a non-cyclic alkylene group, wherein each of the cycloalkylene and non-cyclic alkylene groups has one open bonding site, and wherein cycloalkylene and alkylene are each as previously defined. "Cycloalkylenealkylene" includes moieties having -cycloalkylene-alkylene- and -alkylene-cycloalkylene-bonding orders or configurations.

"Arylenealkylene" refers to a bivalent moiety, wherein an arylene group is bonded to a non-cyclic alkylene group, and each of the arylene and non-cyclic alkylene group has one open bonding site, wherein arylene and alkylene are each as previously defined. "Arylenealkylene" includes moieties having -arylene-alkylene- and -alkylene-arylene-bonding orders or configurations.

"Arylenealkylenearylene" refers to bivalent moieties, wherein two arylene groups are bonded to a non-cyclic alkylene group, and each of the arylene groups has one open bonding site, wherein arylene and alkylene are each as previously defined.

"Cycloalkylenealkylenecycloalkylene" refers to a bivalent moiety, wherein two cycloalkylene groups are bonded to a non-cyclic alkylene group, and each of the cycloalkylene groups has one open bonding site, wherein cycloalkylene and alkylene are each as previously defined.

"Arylenealkylenecycloalkylene" refers to a bivalent moiety, wherein an arylene and a cycloalkylene group are each bonded to a non-cyclic alkylene group, and each of the arylene and cycloalkylene groups has one open bonding site, wherein arylene, cycloalkylene, and alkylene are as previously defined. "Arylenealkylenecycloalkylene" includes moieties having -arylene-alkylene-cycloalkylene- and cycloalkylene-alkylene-arylene-bonding orders or configurations.

"Chain Extenders." The nature of the chain extender group in the polymers of the present invention can vary provided that the polymer of the invention possesses acceptable mechanical properties and release kinetics for the selected therapeutic application. The chain extender group R* is typically a divalent organic radical having a molecular weight of about 60 to about 5000. Additional examples include R* having a molecular weight of about 100 to about 1000, and may contain oxygen atoms, sulfur atoms and/or ester groups.

The chain extender group may be biologically inactive, or may itself possess biological activity. The chain extender group can also be a polyalkylene oxide, such as polyethylene oxide. The chain extender group can also be polyester derived from at least one lactone monomer, such as glycolide, lactide, p-dioxanone, trimethylenecarbonate, or caprolactone. The chain extender group can also comprise other functional groups (including hydroxy groups, amine groups, carboxylic acids, and the like) that can be used to modify the properties of the polymer (e.g. for branching, for cross linking).

When any variable occurs more than one time in any constituent or in any formula, its definition in each occurrence is independent of its definition at every other occurrence. Combinations of substituents and/or variables are permissible only if such combinations result in stable compounds. Within the context of the present invention, compounds are stable if they do not degrade significantly prior to their intended use under normal conditions. In some instances, compounds of the invention are may be designed or required to be bioabsorbed or biodegraded as part of their intended function. Absorbability and/or biodegradability, which may be an advantageous property of the present polymers, is not intended to mean that the polymeric compound are unstable.

Bio-Based Polyester and Polyesteramide Polyols and Methods of Preparation Thereof

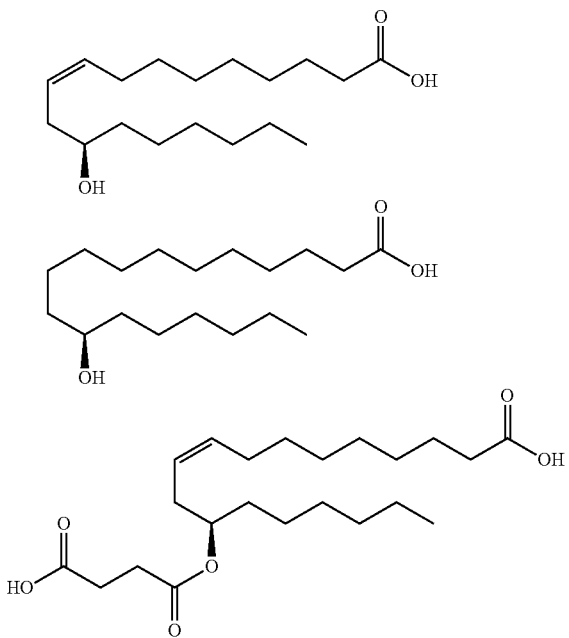

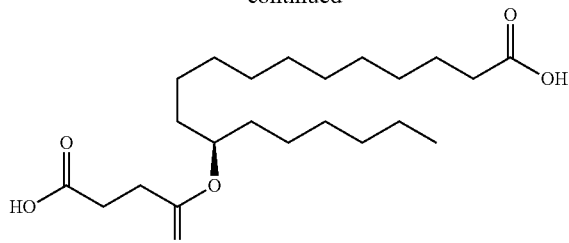
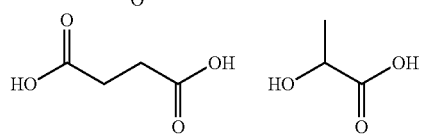
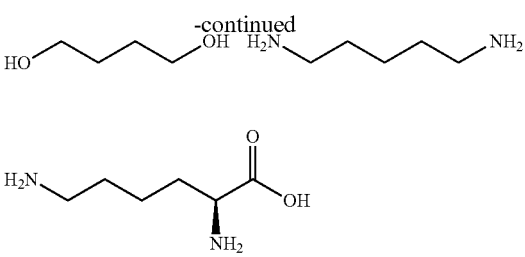
Using the above bio-based monomers, one can make bio-based polyester and polyamide ester polyols for the preparation of bio-based polyurethanes. Examples of bio-based polyols that can be prepared are shown below (BDO=1,4-butane diol):
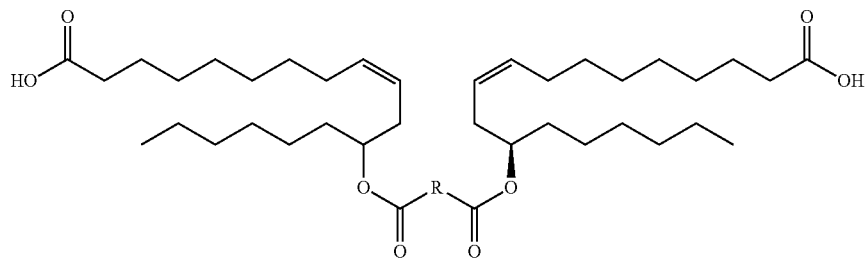
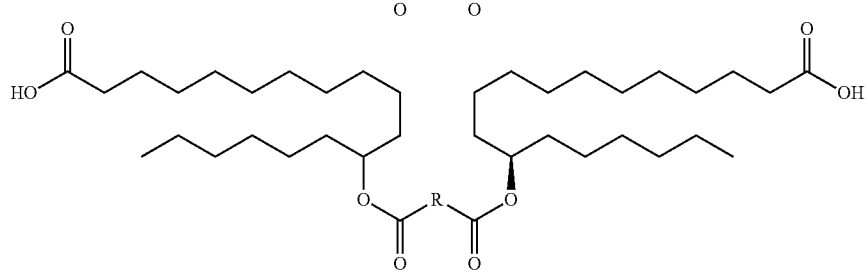
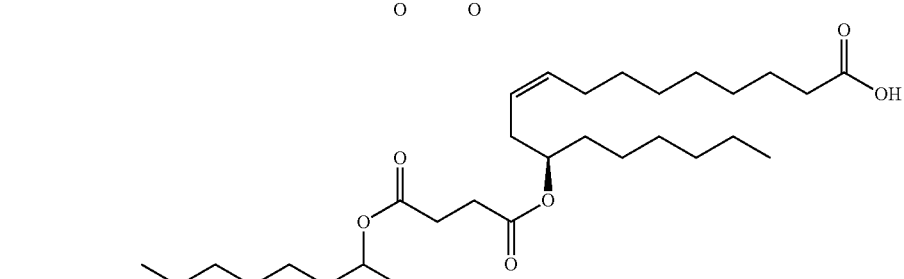
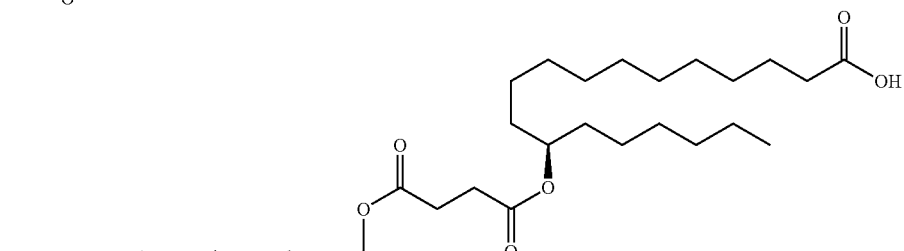

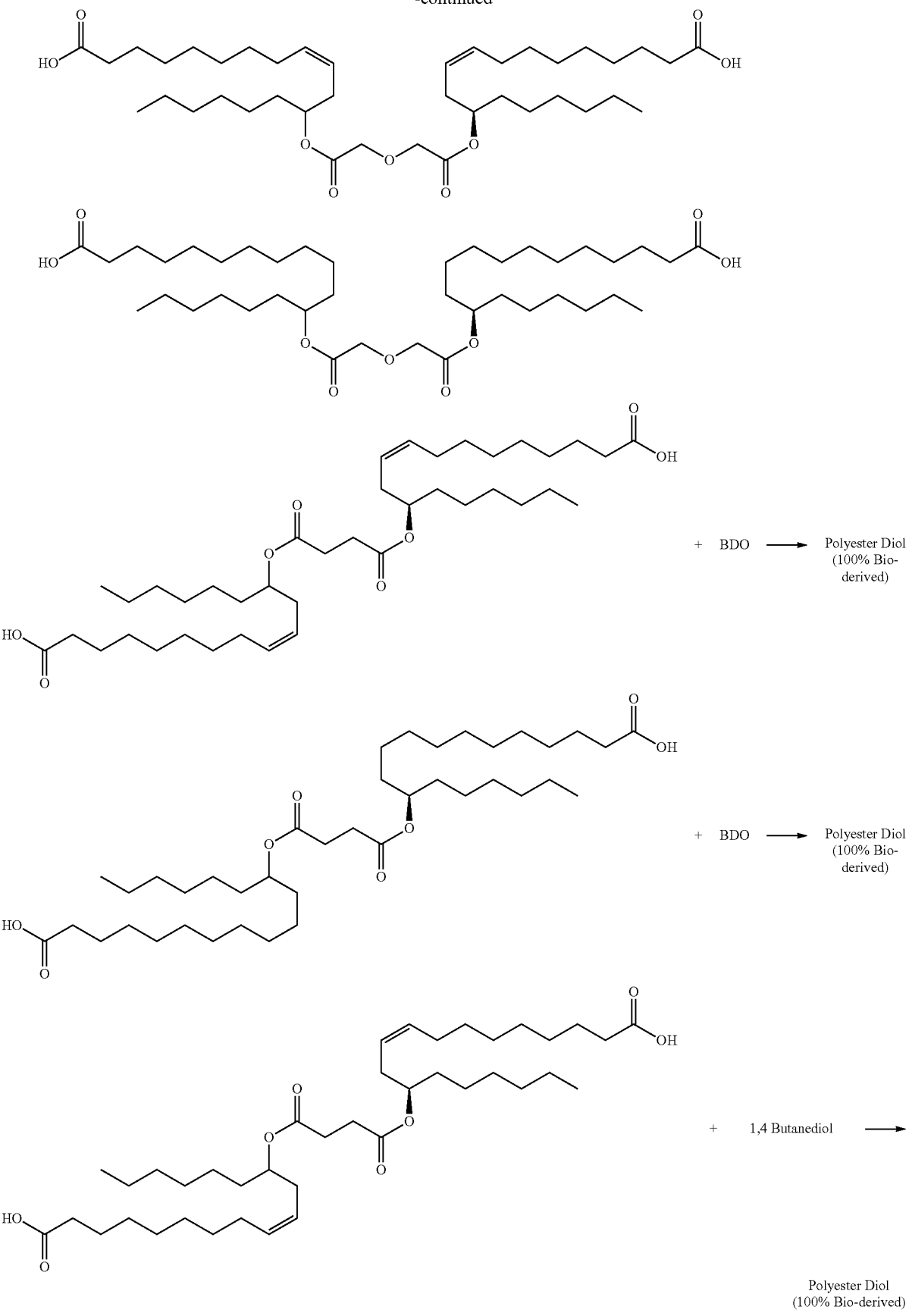

-continued

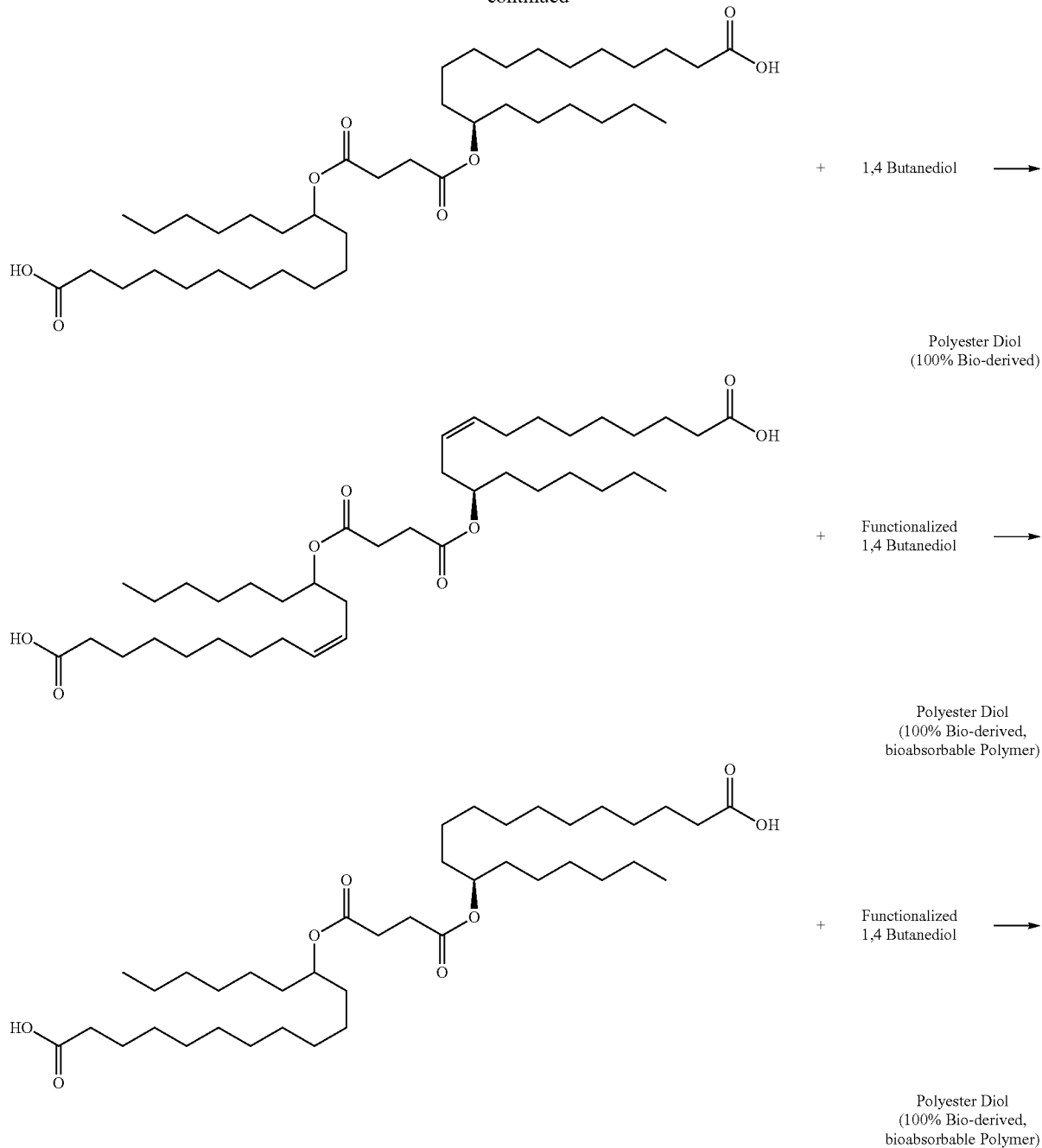

wherein functionalized 1,4-butanediol is prepared by reacting 1,4-butanediol with lactic acid, glycolic acid, p-dioxanone and/or caprolactone.

In another embodiment, copolymers of absorbable polymers of the present invention can be prepared by preparing a prepolymer under melt poly-condensation conditions, followed by adding at least one lactone monomer or lactone prepolymer. The mixture is then subjected to the desired conditions of temperature and time to copolymerize the prepolymer with the lactone monomers.

The polymers of the invention are prepared in accordance with methods commonly employed in the field of synthetic polymers to produce a variety of useful products with valuable physical and chemical properties. The polymers are readily processed into pastes or can be solvent cast to yield films, coatings, microspheres and fibers with different geometric shapes for the design of various medical implants, and may also be processed by compression molding and extrusion.

Polyamides, polyesters, polyureas, polyepoxides, polyesteramides, and polyurethanes prepared in accordance with the present invention have average molecular weights of about 1500 to about 100,000 calculated by Gel Permeation Chromatography (GPC) relative to narrow molecular weight polystyrene standards. Other examples of Polyamides, polyesters, polyureas, polyepoxides, polyesteramides, and polyurethanes have average molecular weights of about 1500 up to about 40,000.

Processes for preparing polyamides of the invention are provided as further embodiments of the invention and are illustrated by the following general method:

These diisocyanates can also be reacted with diamines ($H_2N$—$R^x$—$NH_2$) to prepare biodegradable polyureas The diamines of this invention can also be reacted with diepoxides to prepare biodegradable polyepoxides.

The mechanical properties, such as ultimate tensile strength, of the polyurethanes of the present invention can in some cases be influenced primarily by the polyol component as opposed to the hard segment as in typical segmented polyurethanes.

One type of polyurethane of the present invention is the type known as segmented polyurethane, which is character-

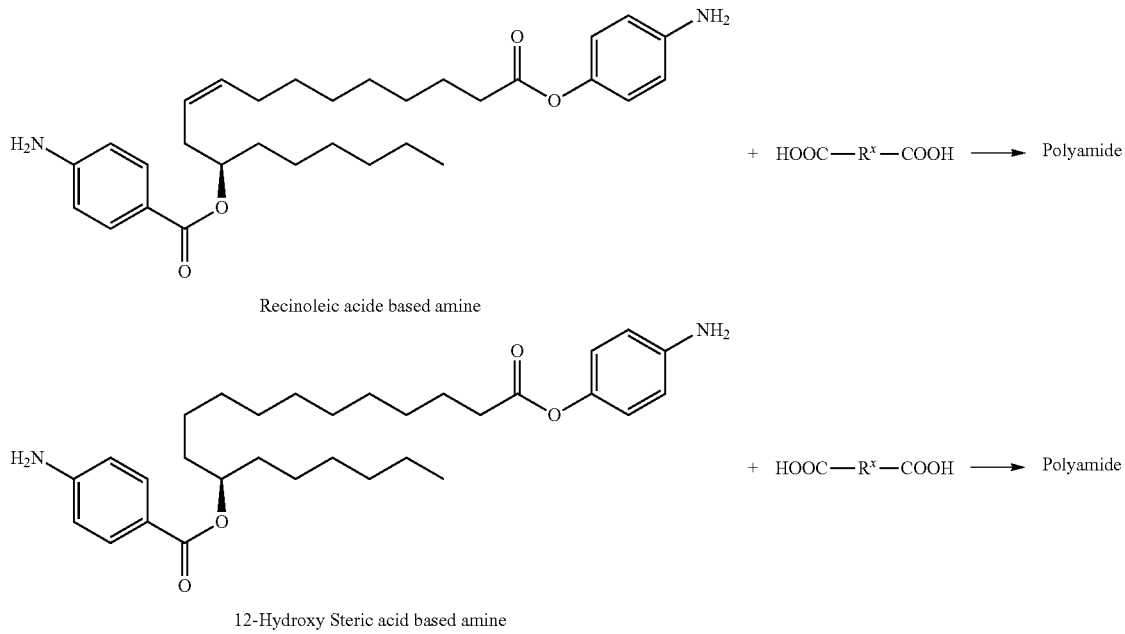

The diamines can also be reacted with diisocyanates (OCN—$R^x$—NCO) to prepare biodegradable polyureas.

Processes for preparing polyurethanes of the invention are provided as further embodiments of the invention and are illustrated by the following general procedure:

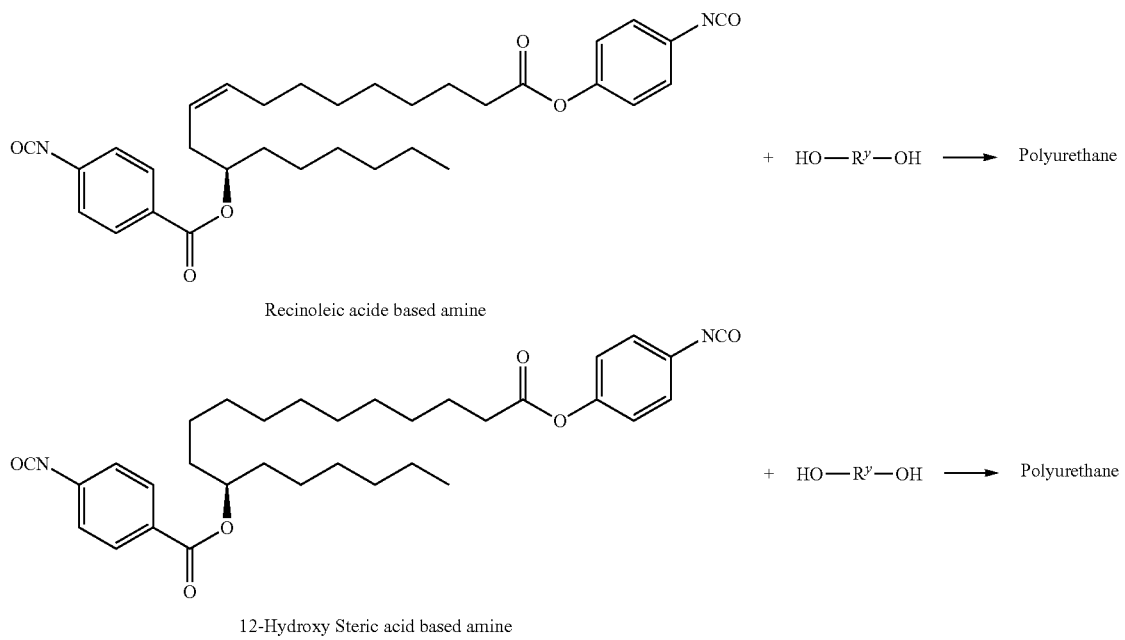

ized by a formation of repeating soft and hard blocks formed from a polyol component, a diisocyanate component, and an optional chain extender, and can occur in a linear, branched or networked form. The chain extender may be reacted with the previously synthesized pre-polymer to generate a high molecular weight polymer, polyurethane for example. However, the formation of polyurethanes may also be carried out using such processes as a single step process involving reaction of the chain extender together with the diisocyanate and the polyol, without the formation of a prepolymer.

The polyol component of a polymer of the present invention is often selected according to the component's toxicity, which is liberated when the polymer is broken down. Two examples of typical polyols are polyethylene oxide and polycaprolactone diol. Others may be suitable in some cases.

The constituents making up the polyurethanes of the present invention can be selected so as to be biodegradable to substantially nontoxic constituents. The term substantially non-toxic refers to materials which when present in the body are physically tolerated and, more specifically, do not cause appreciable cell death (cytotoxicity) or detrimental alteration of normal cell function (such as a mutagenic response). This would of course depend on where and how the material is applied. Detailed in vivo tests may be appropriate to determine the effect of the material on the neighboring cells.

Depending on the synthesis route selected for the segment polyurethane, the cleavable sites of the present invention may be regularly spaced along the length of the chain extender, thereby giving the segmented polyurethane a biodegradability which is, by some measure, predictable. Biodegradability is influenced by a number of factors, including the number of susceptible sites and crystallinity.

The hydrophilicity of a polymer, that is, the extent to which water is accessible to the polymer matrix and the susceptible sites, may also influence its degradability. In those cases where the chain extender has enzyme recognizable side groups, the access of water to the surface of the matrix should increase the rate at which the enzyme can catalyze the reaction between water and the hydrolyzable cleavage sites.

The number of cleavage sites also influences biodegradability. The higher the number of sites generally, the greater the rate of degradation. Typically, the cleavable site is an ester site. For example, the cleavable ester site can be adjacent one or more amino acids. This provides segmented polyurethanes with cleavable sites in its chain extender that may be engineered to be recognizable by an enzyme. In this embodiment of the invention, the rate of degradation is controlled to achieve a desired therapeutic indication.

In another embodiment, the diisocyanate is reacted with the polyol under suitable conditions to form a prepolymer; the prepolymer is then reacted with the chain extender, again under suitable conditions, to form the polyurethane.

Alternatively, multi-functional components can be employed to produce a cross-linked network, and hence non-linear, segmented polyurethane. This could be achieved by the use of a branched complex bearing more than two hydroxyl groups, such as for example a triol, for example. In another case, certain amino acids may also contribute to the formation of a networked polymer. Lysine for example, having an amine group on its side chain, may be reacted with such sites as a isocyanate group on the diisocyanate. Additionally, several lysines may be present in the amino acid segment thereby providing potential bonding sites between each corresponding amine and another site such as an isocyanate group. Thus, such multi-functional components readily allow for the formation of nonlinear segmented polyurethanes.

In another embodiment, substantially non-toxic degradable polyurethanes can be formed from amino acids and substantially non-toxic diols, in such a manner, to be useful as biomaterials for a variety of applications such as artificial skin, wound dressings, tissue engineering scaffolds and the like. The polyurethane materials may be formed by melt or solvent processing techniques such as dissolving the polymer into a solvent, pouring the mixture onto a flat sheet or into a mold and evaporating the solvent, with the polymer remaining therein. Other melt processing techniques may be available by melting a blank of polyurethane and manipulating it into a shape as desired, including tubes or fibers. Porous polyurethane may be formed in a number of ways, including the addition of a gas (typically carbon dioxide) into the polymerization reaction, and trapping the gas into the polymer structure. Alternatively, salt crystals can be added to the solvent polymer mixture during casting wherein the salt is not dissolved. The mixture may be deposited into a dish causing the solvent to evaporate, with the salt material being removed by subsequent washing with water.

In another embodiment, the present invention provides methods and processes for preparing the biodegradable and absorbable polymers of the present invention from the monomers disclosed, vide supra, with or without the inclusion of other monomers. The polymerization processes typically used for the formation of polyurethanes, polyamides, etc., are well-known to those skilled in the art. Representative processes are provided in U.S. Pat. No. 7,772,352, U.S. Pat. No. 8,048,980, U.S. Pat. No. 8,143,325, U.S. Pat. No. 8,367,747, US 2010/0260702 A1, US 2009/0292029 A1, US 2009/0082540, US 2006/0288547 A1, EP 1937182 B1, EP 2298235 A1, EP 1937182 A4, EP 1937182 A2, and WO 27030464 A2, all of which have been assigned to Bezwada Biomedical.

The polyurethane materials disclosed herein may be used in a number of different forms and in a range of applications, both in the biomedical field and others. The material can be fabricated by casting or other molding techniques to form a substrate, which can be used alone or combined with other substrates to form homogenous multi-layered materials. Such multilayered homogeneous polyurethane materials may be formed with layers having different degrees of degradability. Such substrates may range in thickness from about 1 micron to about 5 millimeters for applications suitable for skin repair and the like, and more particularly from about 10 microns to about 3.5 millimeters, and still more particularly from about 50 microns to about 2 millimeters. The thinner the substrate, the more care is needed in handling it.

For bone regeneration and the like, the polyurethane material may range in thickness from about 1 cm to about 5 cm or more, depending on the specific application, including the dimensions of the bone being regenerated.

In another embodiment, the present invention provides polymers that can be used as a pharmaceutical carrier in a drug delivery matrix. The matrix is formed by mixing the polymer with a therapeutic agent.

A variety of different therapeutic agents can be used in conjunction with the polymers of the invention. In general, therapeutic agents administered via the pharmaceutical compositions of the invention include, without limitation antiinfectives such as antibiotics and antiviral agents; analgesics and analgesic combinations; anorexics; antihelmintics; antiarthritics; anti-asthmatic agents; anticonvulsants; antidepressants; antidiuretic agents; antidiarrheals; antihist-amines; antiinflammatory agents; antimigraine preparations; antinauseants; antineo-plastics; antiparkinsonism drugs; antipruritics; antipsychotics; antipyretics, antispas-modics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; para-sympatholytics; psychostimulants; sedatives; tranquilizers; and naturally derived or genetically engineered proteins, polysaccharides, glycoproteins or lipoproteins.

The drug delivery matrix may be administered in any suitable dosage form such as oral, parenteral, subcutaneously as an implant, vaginally or as a suppository. Matrix formulations containing polymers of the invention is formulated by mixing one or more therapeutic agents with the polymer. The therapeutic agent may be present as a liquid, a finely divided solid, or any other appropriate physical form. Typically, the matrix will include one or more additives, e.g., nontoxic auxiliary substances such as diluents, carriers, excipients, stabilizers or the like. However, the presence of such additives is entirely optional. Other suitable additives may be formulated with the polymers of this invention and pharmaceutically active agents or compounds, however, if water is to be used it should be added immediately before administration.

The amount of therapeutic agent will be dependent upon the particular drug employed and medical condition being treated. Typically, the amount of drug represents about 0.001% to about 70%, more typically about 0.01% to about 50%, and most typically about 0.1% to about 20% by weight of the matrix.

The quantity and type of polymer incorporated into a parenteral dosage form will vary depending on the release profile desired and the amount of drug employed. The product may contain blends of polymers of this invention to provide the desired release profile or consistency to a given formulation.

The polymers of this invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (over one to 2,000 hours, including 2 to 800 hours) of effective amounts (0.0001 mg/kg/hour to 10 mg/kg/hour) of the drug. This dosage form can be administered as necessary depending on the subject being treated, the severity of the affliction, the judgment of the prescribing physician, and the like.

Individual formulations of drugs and polymers of this invention may be tested in appropriate in vitro and/or in vivo models to achieve the desired drug release profiles. For example, a drug could be formulated with a polymer of this invention and orally administered to an animal. The drug release profile is monitored by appropriate means, such as by taking blood samples at specific times and assaying the samples for drug concentration. Following this or similar procedures, those skilled in the art are able to formulate a variety of formulations having the desired release profile.

The polyurethanes, polyureas, polyamideurethanes, and/or polyureaurethanes of the invention may be formed into various articles for surgical and medical uses including, without limitation:

a. burn dressings,
b. hernia patches,
c. medicated dressings,
d. fascial substitutes,
e. gauze, fabric, sheet, felt or sponge for liver hemostasis,
f. gauze bandages,
g. arterial graft or substitutes,
h. bandages for skin surfaces,
i. suture knot clip,
j. orthopedic pins, clamps, screws, and plates,
k. clips (e.g., for vena cava),
l. staples,
m. hooks, buttons, and snaps,
n. bone substitutes (e.g., mandible prosthesis),
o. intrauterine devices (e.g., spermicidal devices),
p. draining or testing tubes or capillaries,
q. surgical instruments,
r. vascular implants or supports,
s. vertebral discs,
t. extracorporeal tubing for kidney and heart-lung machines,
u. artificial skin, and the like.

The polyurethanes, polyureas, polyesterurethanes, polyamides, polyesteramides of the invention may be formed into surgical articles using any known technique, such as, for example, extrusion, molding and/or solvent casting. The polyurethanes, polyureas, polyesterurethanes, may be used alone, blended with other bioabsorbable compositions, or in combination with non-bioabsorbable components. A wide variety of surgical articles may be manufactured from the polyurethanes, polyureas, polyamideurethanes, and/or polyureaurethanes described herein. These include but are not limited to clips and other fasteners, staples, sutures, pins, screws, prosthetic devices, wound dressings or coverings, burn dressings or coverings, drug delivery devices, anastomosis rings, stents, stent coatings, films, scaffolds, polyurethane foams, reticulated foams and other implantable medical devices. Examples of medical implantable devices include prosthetic devices, stents, sutures, staples, clips and other fasteners, screws, pins, films, meshes, drug delivery devices or systems, anastomosis rings, surgical dressings and the like. In some preferred embodiments, the surgical articles or components thereof include stents, stent coatings, wound coverings, burn coverings, foams, tissue engineering scaffolds, films, implantable medical devices, and/or controlled drug delivery systems, more preferably stents, stent coatings, wound and/or burn coverings, and/or controlled delivery systems. In certain other preferred embodiments, the surgical articles or components thereof include sutures, ligatures, needle and suture combinations, surgical clips, surgical staples, surgical prosthetic devices, textile structures, couplings, tubes, supports, screws, or pins. In certain preferred drug delivery systems, the systems comprise a polyurethane, polyurea, polyamideurethane, and/or polyureaurethane in admixture with a biologically or pharmaceutically active agent. Non-limiting examples of polymeric carriers in such drug delivery systems and/or pharmaceutical compositions include self-supporting films, hollow tubes, beads, and/or gels. Other preferred uses of the surgical articles include their use as scaffolds for tissue engineering comprising a porous structure for the attachment and proliferation of cells.

Additional examples of the surgical and medical uses of the filaments, films, and molded articles of the present invention include knitted products, woven or non-woven, and molded products including, burn dressings, hernia patches, medicated dressings, facial substitutes, gauze, fabric, sheet, felt or sponge for liver homeostasis, gauze bandages, arterial graft or substitutes, bandages for skin surfaces, suture knot clip, orthopedic pins, clamps, screws, and plates, clips (e.g., for vena cava), staples, hooks, buttons, and snaps, bone substitutes (e.g., mandible prosthesis), bone void fillers, bone cements, intrauterine devices (e.g., spermicidal devices), draining or testing tubes or capillaries, surgical instruments, vascular implants or supports, vertebral discs, extracorporeal tubing for kidney and heart-lung machines, artificial skin and others.

The polyurethanes, polyureas, polyamideurethanes, and/or polyureaurethanes disclosed herein may also be used to fabricate degradable containers and packaging materials which can degrade in landfills in contrast to existing non-degradable materials which present environmental concerns.

The polyurethane material is believed to be especially useful for use as a tissue engineering scaffold, i.e., as a structure for the growth or regeneration of tissue. Polyurethanes may lend themselves to such uses since enzyme-catalyzed degradation may in some cases occur concurrently with the migration or growth of cells into the material, while desirably degrading in the process into its substantially non-toxic constituents. It is also possible, in some cases, that cells migrating into or located adjacent the matrix may themselves exude proteolytic enzymes that will mediate hydrolytic cleavage.

Such tissue engineering scaffolds may have applications in the regeneration of skin and other organs, bone, cartilage, ligaments, tendons, bladder and other tissues. The polyurethane material may also be useful in the production of sutures, which require good mechanical strength, as well as in the production of drug release matrices, in view of their need for degradation to non-toxic materials. The polyurethane material may also be useful for non-biomedical applications, where degradability into substantially non-toxic constituents is an asset. The polyurethane material lends itself to sterilization by such techniques as gamma radiation and ethylene oxide treatments.

Fibers made from the present polyurethanes, polyureas, polyamideurethanes, and/or polyureaurethanes can be knitted or woven with other fibers, either bioabsorbable or non-bioabsorbable, to form meshes or fabrics. Compositions including these polyurethanes, polyureas, polyamideurethanes, and/or polyureaurethanes may also be used as bioabsorbable coatings for surgical devices.

Another embodiment of the invention is directed to compositions containing the polyurethanes, polyureas, polyamideurethanes, and/or polyureaurethanes described herein which may be used to make reinforced composites. Thus, for example, the polyurethane, polyurea, polyamideurethane, and/or polyureaurethane composition may form the matrix of the composite and may be reinforced with bioabsorbable or non-bioabsorbable fibers or particles. Alternatively, a matrix of any bioabsorbable or non-bioabsorbable polymer composition may be reinforced with fibers or particulate material made from compositions containing the polyurethanes, polyureas, polyamideurethanes, and/or polyureaurethanes described herein.

In another embodiment, the polyurethanes, polyureas, polyamideurethanes, and/or polyureaurethanes described herein may be admixed with filler. The filler may be in any particulate form, including granulate or staple fibers. While any known filler may be used, hydroxyapatite, tricalcium phosphate, bioglass or other bioceramics are the preferred fillers. Normally, from about 10 grams to about 400 grams of filler are mixed with about 100 grams of polymer. The filled, cross-linked polymers are useful, for example, as molding compositions.

It is further contemplated that one or more medico-surgically useful substances may be incorporated into compositions containing the polyurethanes, polyureas, polyamideurethanes, and/or polyureaurethanes described herein. Examples of such medico-surgically useful substances include, for example and without limitation, those which accelerate or beneficially modify the healing process when particles are applied to a surgical repair site. For example, articles made from compositions containing the presently disclosed polyurethanes, polyureas, polyamideurethanes, and/or polyureaurethanes may carry a therapeutic agent which will be deposited at the repair site. The therapeutic agent may be chosen for its antimicrobial properties, capability for promoting repair or reconstruction and/or new tissue growth. Antimicrobial agents such as broad spectrum antibiotics, for example and without limitation, gentamycin sulfate, erythromycin, or derivatized glycopeptides which are slowly released into the tissue, may be applied in this manner to aid in combating clinical and sub-clinical infections in a tissue repair site. To promote repair and/or tissue growth, one or several growth promoting factors may be introduced into the articles, e.g., fibroblast growth factor, bone growth factor, epidermal growth factor, platelet-derived growth factor, macrophage-derived growth factor, alveolar-derived growth factor, monocyte-derived growth factor, magainin, and the like. Examples of therapeutic indications include, without limitation, glycerol with tissue or kidney plasminogen activator to cause thrombosis, superoxide dismutase to scavenge tissue-damaging free radicals, tumor necrosis factor for cancer therapy or colony stimulating factor and interferon, interleukin-2 or other lymphokine to enhance the immune system.

In another embodiment, branched or linear bioabsorbable polyurethanes and the like of the present invention may also be derived from diisocyanates based on cycloaliphatic amino acids such as aminocyclohexanecarboxylic acid as well as cycloaliphatic amino alcohols such as aminocyclohexanol. Polyurethanes and the like from these diisocyanates can be prepared according to the procedures described in U.S. Patent Application Publication Nos. 20060188547, 20090292029, European Patent Publication No. EP 1937182 and WO 2007030464. Polyurethanes and the like resulting from cycloaliphatic amino acids as well as cycloaliphatic amino alcohols will find use in a variety of applications including biomedical applications wherein controlled hydrolytic degradation is desired.

In another embodiment, absorbable polyester amides can be prepared by reaction of amide diols, and/or bioabsorbable polyols, with diacids including but not limited to oxalic acid, succinic acid, malonic acid, butanedioic acid, adipic acid, azelaic acid, sebacic acid, diglycolic acid, 3,6-dioxaoctanedioic acid, 3,6,9-trioxaundecanoic acid, functionalized oxaacids, polyethyleneglycol diacids of average molecular weight from 300 to 2000 and blends thereof.

In another embodiment, bioabsorbable polyamides will be prepared by reaction of diamines with diacids including but not limited to oxalic acid, succinic acid, malonic acid, butanedioic acid, adipic acid, azelaic acid, sebacic acid, diglycolic acid, 3,6-dioxaoctanedioic acid, 3,6,9-trioxaundecanoic acid, functionalized oxaacids, polyethyleneglycol diacids of average molecular weight from 300 to 2000 and blends thereof.

The monomers of the present invention can be polymerized to form absorbable polymers (e.g., polyesters, polyamides, polyester amides, polyurethanes, and polyanhydrides). It can be advantageous for the monomers that are to be polymerized to have at least two active sites (e.g., 2 or 3) for polymerization. These active sites include amino, isocyanate and carboxylic acid groups. The monomers with at least two active sites can also be copolymerized with selected difunctional molecules (e.g., dicarboxylic acids, dialcohols, diisocyanates, amino-alcohols, hydroxy-carboxylic acids, and diamines) based on the starting functionalized amino acid to form bioabsorbable polymers. The polymers (and copolymers) of the present invention can also be further reacted/polymerized to form additional useful polymers of the present invention.

It would be readily apparent to one of ordinary skill in the art once armed with the teachings in the present application that the diisocyanates of the present invention may be reacted with a variety of reactants that are typically employed in the preparation of bioabsorbable and biocompatible polyurethanes and/or polyester urethanes, preferably with tunable physical, mechanical properties and/or hydrolytic degradation profiles. It would also be apparent to the ordinarily skilled artisan that the terminal groups for given polyurethane, or polyester may be derivatized by further reacting the polyurethane and/or polyesters with additional derivatizing agents. Polyurethanes terminated with —NCO or hydroxyl groups can be prepared by varying the ratio of isocyanates:hydroxyl groups in the reaction mixture i.e. (isocyanates, chain extender and polyol). Polyurethanes with high molecular weights are formed when the ratio of isocyanates:hydroxyl group is 1. Furthermore, by varying the ratio of isocyanates:hydroxyl groups in the reaction mixture, polyurethanes with tunable physical and mechanical properties can be obtained. It would also be apparent to the ordinarily skilled artisan that the terminal groups for given polyurethane, or polyester may be derivatized by further reacting the polyurethane and/or polyesters with additional derivatizing agents.

The polymers of the present invention may be used as pharmaceutical carriers in a drug delivery matrix, i.e., a matrix for a biologically active substance (i.e., agent). The matrix may be formed by mixing the polymer with a biologically active agent. The biologically active agent can be dispersed into the polymer solution for example during preparation of matrix or via melt blending. A vast variety of different biologically active agents may be used in conjunction with the polymers of the invention. In general, therapeutic agents administered via the pharmaceutical compositions of the invention include, without limitation: anti-infectives such as antibiotics and antiviral agents; analgesics and analgesic combinations; anorexics; anti-helmintics; anti-arthritics; anti-asthmatic agents; anticonvulsants; antidepressants; anti-diuretic agents; anti-diarrheals; anti-histamines; anti-inflammatory agents; anti-migraine preparations; anti-nauseants; anti-neoplastics; anti-parkinsonism drugs; anti-pruritics; anti-psychotics; anti-pyretics, anti-spasmodics; anti-cholinergics; sympathomimetics; xanthine derivatives; cardiovascular preparations including calcium channel blockers and beta-blockers such as pindolol and anti-arrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; para-sympatyholytics; psychostimulants; sedatives; and tranquilizers; and naturally derived or genetically engineered proteins, polysaccharides, glycoproteins or lipoproteins.

The drug delivery matrix may be administered in any suitable dosage form such as oral, parenteral, subcutaneously as an implant, vaginally or as a suppository. Matrix formulations containing polymers of the invention may be formulated by mixing one or more therapeutic agents with the polymer. The biologically active agent may be present as a liquid, a finely divided solid, or any other appropriate physical form. Typically, the matrix will include one or more additives, e.g., nontoxic auxiliary substances such as diluents, carriers, excipients, stabilizers or the like. However, the presence of such additives is optional. Other suitable additives may be formulated with the polymers of this invention and pharmaceutically active agent or compound. If water is to be used as an additive, it is preferably be added immediately before administration.

The amount of biologically active agent will be dependent upon the particular agent employed and medical condition being treated. Typically, the amount of drug represents about 0.001% to about 70%, more typically about 0.01% to about 50%, and most typically about 0.1% to about 20% by weight of the matrix.

The quantity and type of polymer incorporated into a parenteral dosage form will vary depending on release profile desired and the amount of drug employed. The product may contain blends of polymers of this invention to provide the desired release profile or consistency to a given formulation.

The polymers of this invention, upon contact with body fluids including blood or the like, undergo gradual degradation (mainly through hydrolysis) with concomitant release of the dispersed drug for a sustained or extended period (as compared to the release from an isotonic saline solution). This may result in prolonged delivery (over about one to about 2,000 hours, preferably about two to about 800 hours) of effective amounts (including, for example, about 0.0001 mg/kg/hour to about 10 mg/kg/hour) of the drug. This dosage form may be administered as necessary depending on the subject being treated, the severity of the affliction, the judgment of the prescribing physician, and the like.

Individual formulations of drugs and polymers of this invention may be tested in appropriate in vitro and in vivo models to achieve the desired drug release profiles. For example, a drug may be formulated with a polymer of this invention and administered to an animal (e.g., orally). The drug release profile may be monitored by appropriate means, such as by taking blood samples at specific times and assaying the samples for drug concentration. Following this or similar procedures, those skilled in the art may formulate a variety of formulations.

It is further contemplated that one or more medico-surgically useful substances (biologically active agents) may be incorporated into compositions containing the bioabsorbable polyurethanes and/or polyester amides described herein. Examples of such biologically active agents include, for example, those which accelerate or beneficially modify the healing process when particles are applied to a surgical repair site. For example, articles made from compositions containing the present polyurethanes and/or polyesters may carry a therapeutic agent which will be deposited at the repair site. The biologically active agent may be chosen for its antimicrobial properties, capability for promoting repair or reconstruction and/or new tissue growth. Antimicrobial agents such as broad spectrum antibiotic, for example, gentamycin sulfate, erythromycin, or derivatized glycopeptides which are slowly released into the tissue may be applied in this manner to aid in combating clinical and sub-clinical infections in a tissue repair site. To promote repair and/or tissue growth, one or several growth promoting factors may be introduced into the articles, e.g., fibroblast growth factor, bone growth factor, epidermal growth factor, platelet derived growth factor, macrophage derived growth factor, alveolar derived growth factor, monocyte derived growth factor, magainin, and the like. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

It is contemplated that it may be desirable to dye articles made from compositions containing the present branched bioabsorbable polyurethanes and/or polyesters in order to increase visibility of the article in the surgical field. Dyes, such as those known to be suitable for incorporation in sutures, may be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979), the disclosures of which are hereby incorporated herein by reference, in their entireties. Preferably, articles in accordance with this disclosure may be dyed by adding up to about a few percent and preferably about 0.2% dye to the resin composition prior to extrusion.

Biologically active hydroxy compounds that can be used as a pendant group or covalently bonded to the amino acid of present invention of the present invention include acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, bupheniode, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipriflavone, isoetarine, isoprenaline, isoxsuprine, itopride hydrochloride, ketobemidone, khellin, labetalol, lactylphenetidin, levodopa. levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, normolaxol, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, alpha-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, xamoterol.

Other biologically active phenolics that can be used include acacetin, 4-acetamido-2-methyl-1-naphthol, acetaminophen, albuterol, allenolic acid, aloe emodin, aloin, β-amino-4-hydroxy-3,5-di-iodohydrocinnamic acid, N-(5-amino-2-hydroxyphenyl)-benzeneacetamide, 4-amino-1-naphthol, 3-aminosalicylic acid, 4-aminosalicylic acid, anacardic acid, p-anol, anthragallol, anthralin, anthranol, anthrarobin, anthrarufin, apigenin, apiin, apocynin, aspidinol, aspirin, baptigenin, benzestrol, benzoresorcinol, bisphenol a, bisphenol b, butylated hydroxylanisole, butylated hydroxytoluene, capobenic acid, trans-1-(3'-carboxy-4'-hydroxyphenyl)-2-(2",5"-dihydroxyphenyl)ethane, catechin, chlorogenic acid, m-chlorophenol, 5-chloro-8-quinolinol, chloroxylenol, chlorquinaldol, chromo-nar, chrysin, cinametic acid, clorophene, coniferyl alcohol, p-coumaric acid, coumes-trol, coumetarol, daphnetin, datiscetin, deoxyepinephrine, 3,5-diiodothyronine, 3,5-di-iodotyrosine, dimethophrine, diosmetin, diresorcinol, disoprofol, dopa, dopamine, drosophilin a, efloxate, ellagic acid, embelin, Equol, eriodictyol, esculetin, esculin, ethylnorepinephrine, ethyl vanillin, eugenol, eupatorin, fenadiazole, ferulic acid, fisetin, 3-fluoro-4-hydroxyphenylacetic acid, fraxetin, fustin, galangin, gallacetophe-none, gallic acid, gardenins, genistein, gentisyl alcohol, gepefrine, geranylhydroqui-none, [6]-gingerol, gossypol, guaiacol, guaifenesin, harmalol, hematoxylin, hinderin, homoeriodictyol, homogentisic acid, homovanillic acid, hydroxyamphetamine, 2-hydroxy-5-(2,5-dihydroxybenzylamino)-2-hydroxybenzoic acid, 4-hydroxy-3-methoxy-mandelic acid, n-(p-hydroxyphenyl)glycine, hydroxyprocaine, 8-hydroxyquinoline, hypericin, irigenin, isoproterenol, isoquercitrin, isothebaine, kaempferol, liothyronine, luteolin, mangostin, 5,5'-methylenedisalicylic acid, n-methylepinephrine, metyrosine, morin, mycophenolic acid, myricetin, naringenin, nylidrin, orcinol, osalmid, osthole, oxantel, paroxypropione, pentachlorophenol, 3-pentadecylcatechol, p-pentyloxy-phenol, phloretin, phloroglucinol, pinosylvine, plumbagin, pyrocatechol, pyrogallol, quercetagetin, quercetin, resacetophenone, rhamnetin, rhein, sakuranetin, salicyl alcohol, salicylanilide, 4-salicyloylmorpholine, salsalate, scopoletin, scutellarein, serotonin, (3,4,5-trihydroxyphenyl)methylenepropanedinitrile, thymol, thyropropic acid, thyroxine, tiratricol, tyrosine, vanillic acid, and vanillin.

Further biologically active carboxylic acid and/or amine compounds that can be used as a pendant group or covalently bonded to the amino acid of the present invention include Acemetacin, Aceclofenac, Acediasulfone, Adipiodone, Alminoprofen, Amisulpride, Amlexanox, Amodiaquine, Amosulalol, Amoxicillin, Amsacrine, Anileridine, Azacyclonol, Baccofen, Balsalazide sodium, Bentiromide, Benzocaine, Bromopride, Bumetanide, Carprofen, Carvedilol, Carzenide, Cefprozil, Cinitapride, Cinmetacin, Clebopride, Clenbuterol, Clometacin, Cromoglicic acid, Diclofenac, Diflunisal, Eprosartan, Ethoxzolamide, Fendosal, Flufenamic acid, Furosemide, Ibuprofen, Indometacin, Iobenzamic acid, Iocarmic acid, Iocetamic acid, Iodoxamic acid, Ioglycamic acid, Iophenoic acid, Iotroxic acid, Mefenamic acid, Nadoxolol, Naproxen, Nedocromil, D-Norpseudoephedrine, paracetamol Repaglinide, Salazosulfapyridine, Salicylic Acid, Salsalate and Sarpogrelate.

Examples of biologically active dihydroxy compounds that can be used to as a pendant group or covalently bonded to the amino acid of present invention of present invention include Adrenalone, Alfuzosin, Alibendol, Amrubicin, Apomorphine, Bamethan, Benzquinamide, Bevantolol, Bifluranol, Bisacodyl, Brodimoprim, Bunazosin, Bupheniode, Carbidopa, Carbuterol, Cyclofenil, Cyclovalone, Daunorubicin, Dichlorophen, Dienestrol, Diethylstilbestrol, Dimestrol, Dithranol, Donepezil, Doxefazepam, Doxorubicin, Entacapone, Epinepheine, Epirubicin, Esomeprazole, Etamivan, Etamsylate, Etilefrine, Ezetimibe, Fenticlor, Fluorescein, Folescutol, Formoterol, Gefitinib, Hexestrol, Hexylresorcinol, Hydroxyethyl salicylate, Ifenprodil, Isoetarine, Isoxsuprine, Itopride. HCl, Khellin, Labetalol, Mitoxantrone, Morclofone, Moxaverine, Normolaxol, Omeprazole, Oxilofrine, Oxepertine, Phenacaine, Phenolphthalein, Prazosin, Tolcapone, Vesnarinone, and Vetradutine.

Examples of biologically active diamino compounds that can be used as a pendant group or covalently bonded to the amino acid of present invention of present invention include Amisulpride, Amodiaquine, Amosul-alol, Amoxicillin, Amsacrine, Azacyclonol, Bromopride, Carvedilol, Cefprozil, Cinitapride, Clebopride, Clenbuterol, Ethoxzolamide, Nadoxolol, and D-Norpseudoephedrine.

Examples of biologically active hydroxy/amino compounds that can be used as a pendant group include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudo-ephedrine, and paracetamol.

Examples of biologically active dicarboxylic acid compounds that can be used as a pendant group or covalently bonded to the amino acid of present invention of present invention include Adipiodone, Cromoglicic acid, Eprosartan, Iocarmic acid, Iodoxamic acid, Ioglycamic acid, Iotroxic acid, Nedocromil.

Examples of biologically active hydroxy/carboxylic acid compounds that can be used as a pendant group or covalently bonded to the amino acid of present invention include Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active hydroxyl-acids for use as the pendant group or covalently bonded to the amino acid of present invention include 4-hydroxycinnamic acid, caffeic acid, chlorogenic acid, ferulic acid, sinapic acid, vanillic acid, Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of useful biologically active amino/carboxylic acid compounds that can be used as a pendant group of present invention include Aceclofenac, Acediasulfone, Alminoprofen, Amlexanox, Anileridine, Baccofen, Balsalazide sodium, Benzocaine, Bumetanide, Carprofen, Carzenide, Diclofenac, Flufenamic acid, Furosemide, Iobenzamic acid, Iocetamic acid, and Mefenamic acid.

Examples of biologically active diamino compounds useful in the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, amino acids (L-lysine), and natural products.

Examples of naturally occurring biologically active phenolics include bergaptol, caffeic acid, capsaicin, coumarin, daidzein, 2,5-dihydroxy-benzoic acid, ferulic acid, flavonoids, glycitein (isoflavone), 4-hydroxycinnamic acid, 4-hydroxy-coumarin, isopimpinellin, resveratrol, synapic acid, vanillic acid, vanillin, chalcones, soybean flavonoids and derivatives thereof.

Capsaicin is a biologically active phenolic that is the active component of cayenne pepper. The capsaicin is an amide of vanillylamine and $C_8$ to $C_{13}$ branched fatty acids. Topical application of capsaicin stimulates and blocks small pain fibers by depleting them of the neurotransmitter substance P that mediates pain impulses. A cream made from 0.025%-0.075% capsaicin applied 4× daily may help peripheral neuropathic pain, post-herpetic neuralgia, trigeminal neuralgia, psoriasis and fibromyalgia. It is also useful for diabetic neuropathy, cluster headaches, earache, osteo- and rheumatoid arthritis. Capsaicin is a powerful pain reliever.

Naproxen, paracetamol, acetaminophen and acetylsalicylic acid are biologically active phenolics that belong to the class of drugs called non-steroidal anti-inflammatory drugs or NSAIDs. The NSAIDs provide relief by blocking the action of prostaglandins, which are hormone-like substances that contribute to pain, inflammation, fever and muscle cramps. Phenolic moieties, synthetic and naturally occurring, are part of many drugs.

The compounds employed in the methods of the present invention may be prepared in a number of ways well known to those skilled in the art. The compounds may be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

The surgical articles, component thereof, polymeric carrier, or the like can comprise a polymer formed by reacting an amine of one of the invention with an isocyanate, carboxylic acid, activated carboxylic acid, or epoxide, or an isocyanate of the invention with an amine, alcohol, aminoalcohol, thiol or combination thereof, or a carboxylic acid of the invention with an alcohol, amine or combination thereof.

The following examples are included to further illustrate the invention and are not to be considered as limiting the invention anyway. Melting points were measured for all products by using a Polmon (MP 96) melting point apparatus. For all the products, NMR was run using a Varian 200 MHz and tetramethylsilane as an internal standard.

EXAMPLES

Example 1

Diisocyanate from Ricinoleic acid, 4-nitro-benzoic acid, and 4-nitro phenol

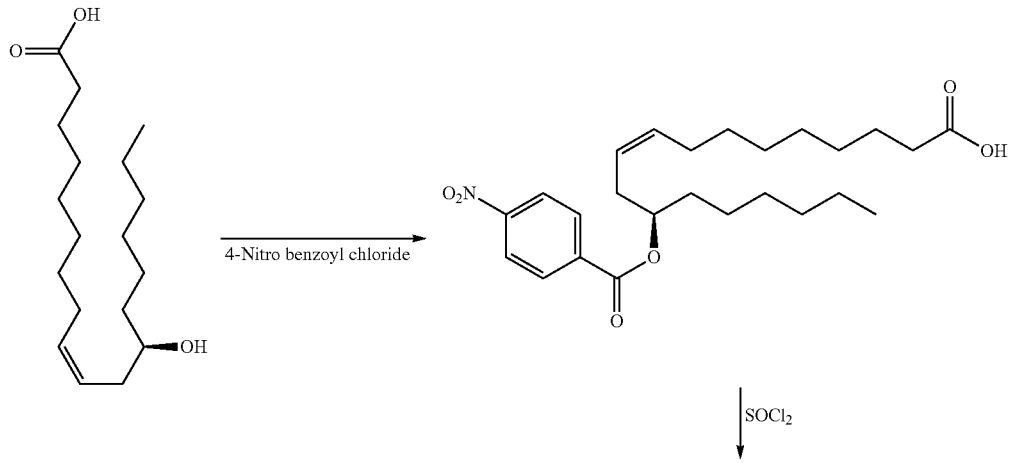

-continued
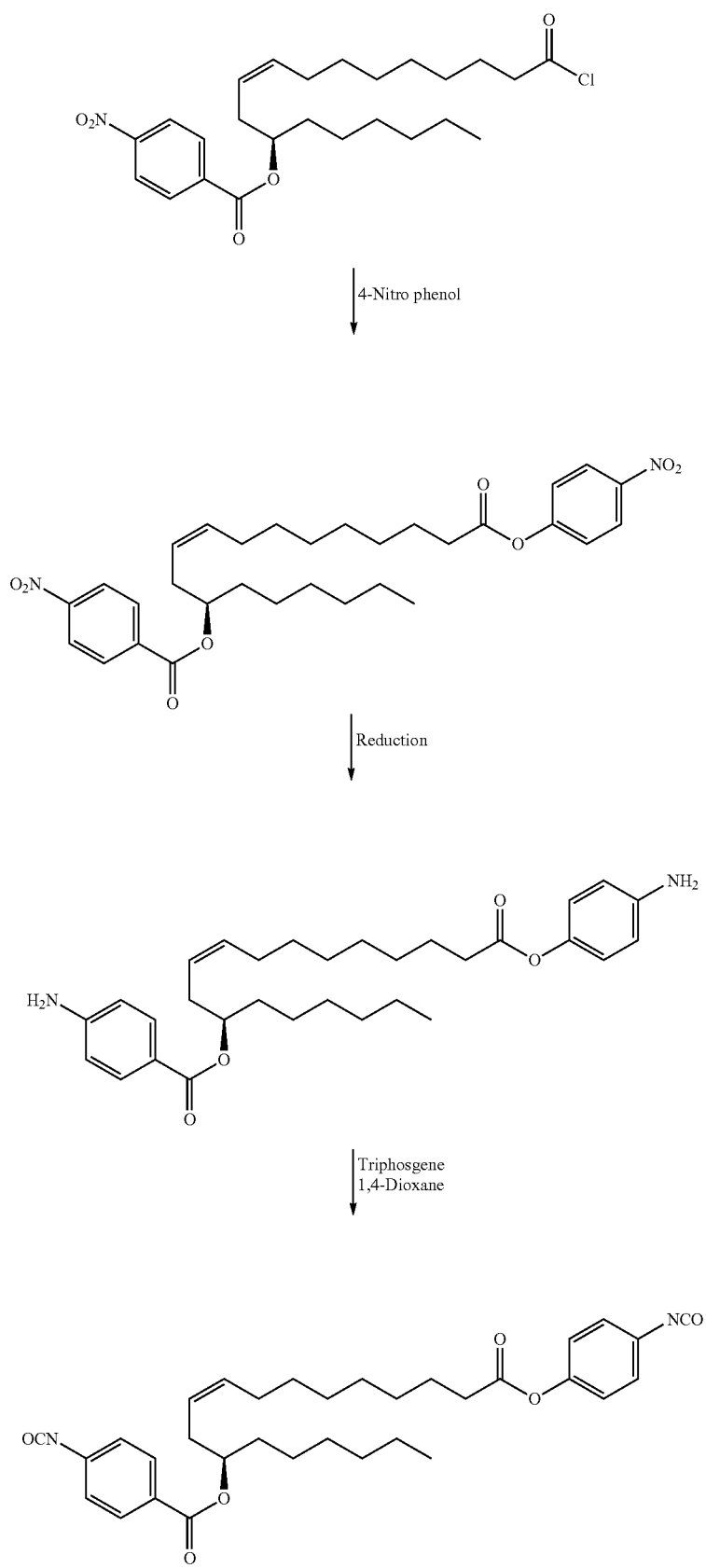

Example 1A

Synthesis of 4-Nitro Benzoyl Chloride

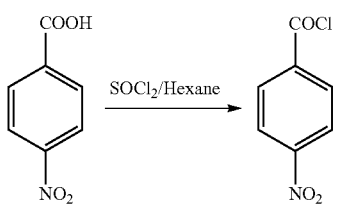 [SMILES: O=C(O)c1ccc([N+](=O)[O-])cc1 ; O=C(Cl)c1ccc([N+](=O)[O-])cc1]

Thionyl chloride (3.0 L) was added drop wise to 4-Ntro benzoic acid (1.5 kg) at ambient temperature under nitrogen atmosphere and heat the mass to reflux and maintained for 6 hours at which time TLC shown completion of the reaction. Then distilled out completely excess Thionyl chloride under reduced pressure, remove the traces with dichloromethane as co solvent under reduced pressure at 55-60° C. The resulted residue was precipitated with petroleum ether (3 L) at 5-10° C. and stirred for 30 minutes at 5-10° C. The resulting solid was filtered and kept under nitrogen and dried well to yield (1400 g) of pure 4-nitro benzoyl chloride as pale yellow powder with a melting point of 69-71° C.

Example 1B

Synthesis of Ricinoleic Acid Mono Nitro Acid

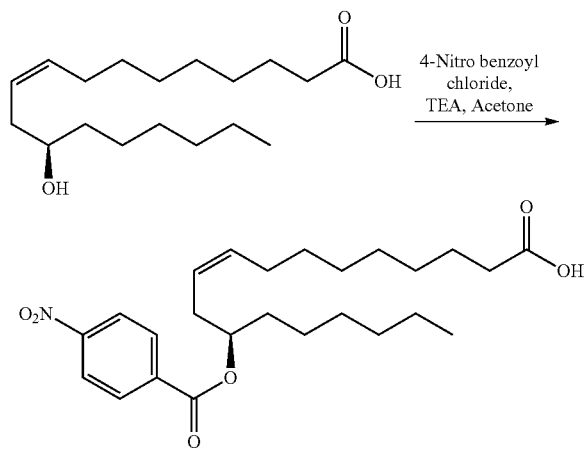

To a mixture of ricinoleic acid (1600 g), triethylamine (1100 mL) in acetone (6 L) at 0-5° C., was added 4-nitro benzoyl chloride (1200 g). It was stirred at room temperature for 16 hours. After the reaction was completed then the total reaction mass was poured onto cold water (12 L) and extracted with ethyl acetate (6 liter) and combined total organic layers and washed with 15% $NaHCO_3$ solution (IL) and 15% NaCl solution (1.0 L) followed by water washing (1.0 L), then dry the organic layer with sodium sulphate and distilled up the solvent under reduced pressure completely till thick oily mass is obtained. Resulting crude was purified by column chromatography by using hexane: ethyl acetate (9:1) to yield pure 4-nitro-benzoic acid 11-carboxy-1-hexyl-undec-3-enyl ester product as light yellow thick syrup (750 g). The resulting compound was characterized by $^1$H NMR (DMSO-$d_6$) δ 0.85 (t, 3H, $CH_3$), 1.12-1.6 (m, 22H, 11×$CH_2$), 1.91 (m, 2H, $CH_2$), 2.2-2.32 (m, 4H, 2×$CH_2$), 3.5 (m, 1H, CH) 5.52 (m, 1H, CH), 5.65 (m, 1H, CH), 8.25-8.35 (m, 4H, Ar).

Example 1C

Synthesis of Ricinoleic Acid Di-Nitro Compound

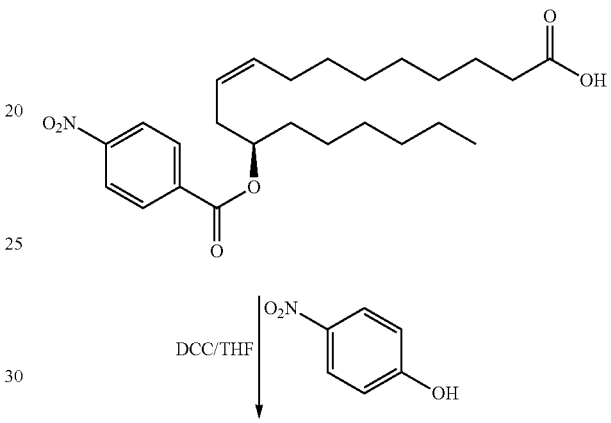

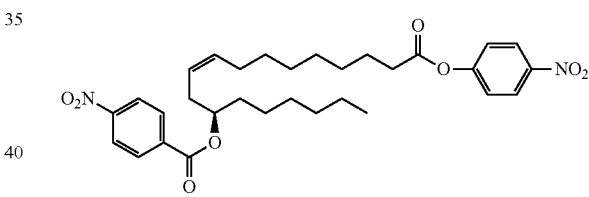

To a solution of 4-Nitro-benzoic acid 11-carboxy-1-hexyl-undec-3-enyl ester (700 g) in dry THF (2 L), Di-azabicyclo-undecane (DBU) (24 g) at 5-10° C., was added a solution of N,N'dicyclohexylcarbodiimide DCC (390 g) in 600 ml THF under nitrogen atmosphere, and later stirred at room temperature for 24 hours. Check TLC and filtered off the DCU salts wash with hot THF 400 ml, combined total filtrate mass and THF solvent was distilled off around 75% under reduced pressure at 60-65° C., the resulted mass was poured into ice water (3 L) and extracted with ethyl acetate (3 L) and combined total organic layers and wash with 15% $NaHCO_3$ solution (1 L) and 15% NaCl solution (1.0 L) followed by water washing (1.0 L), then dry the organic layer with sodium sulphate and distill up the solvent under reduced pressure completely till get thick oily mass. The resulted crude was purified by column chromatography by using hexane: ethyl acetate (9.5:0.5) as eluant to get the pure 4-nitro-benzoic acid 1-hexyl-11-(4-nitro-phenoxycarbonyl)-undec-3-enyl ester product as deep yellow thick syrup (300 g). The resulting compound was characterized by $^1$H NMR (CDCl$_3$) δ 0.86 (t, 3H, $CH_3$), 1.35-1.65 (m, 20H, 10×$CH_2$), 1.78 (m, 2H, $CH_2$), 2.31-2.42 (m 4H 2×CH$_2$), 3.5 (m, 1H, CH) 5.52 (m, 1H, CH), 5.65 (m, 1H, CH), 7.25-7.35 (m, 4H, Ar), 8.28-7.32 (m, 4H, Ar).

Example 1D

Synthesis of Ricinoleic Acid Diamine Compound

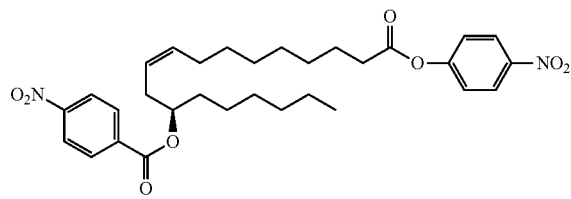

↓ Reduction

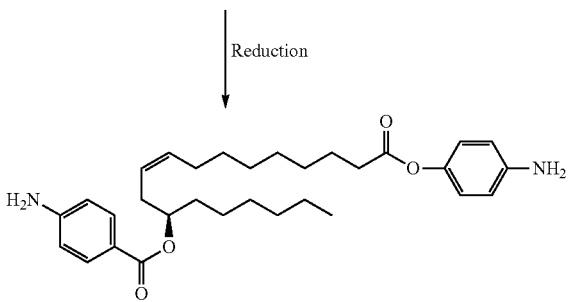

To a solution of 4-nitro-benzoic acid 1-hexyl-11-(4-nitrophenoxy carbonyl)-undec-3-enyl ester (300 g) in ethyl acetate (1.5 L) in a pressure vessel was added Raney Nickel (120 g) added, and the mixture stirred under an atmosphere of Hydrogen (8-10 Kg) for 8 hours at a temperature of 60-65° C. The catalyst was removed by filtration. The solvent was distilled off completely under reduced pressure at 65-70° C. and removed traces for 1 hour at 85-90° C. to get pure 4-aminobenzoic acid 11-(4-amino-phenoxycarbonyl)-1-hexyl-undec-3-enyl ester product as deep yellow thick syrup (190 g). The resulting compound was characterized by $^1$H NMR (CDCl$_3$) δ 0.88 (t, 3H, CH$_3$), 1.2-1.65 (m, 24H, 12×CH$_2$), 2.12 (t, 2H, COCH$_2$), 3.5 (m, 1H, CH) 5.12 (m, 1H, CH), 5.45 (m, 1H, CH), 6.55 (m, 4H, Ar), 6.85 (m, 2H, Ar), 7.75 (m, 2H, Ar).

Example 1E

Synthesis of Ricinoleic Acid Diisocyanate Compound

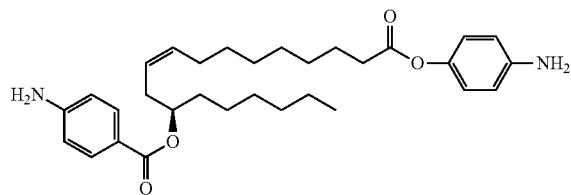

↓ Tri phosgene

-continued

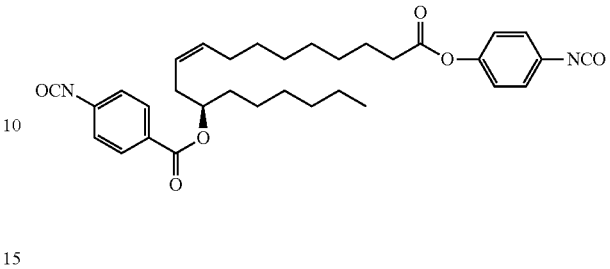

To a solution of 44-Amino-benzoic acid 11-(4-amino-phenoxycarbonyl)-1-hexyl-undec-3-enyl ester (160 g) in dry 1,4-dioxane (1.8 L) Tri phosgene (158 g) was added 320 ml of 1,4 dioxane. The solution was heated up to 60-65° C. followed by cooling to room temperature at which temperature the mass became clear solution. The solution was then again heated up to 100-105° C. and stirred for 3 to 4 hours. The solvent was distilled off completely under reduced pressure at 85-90° C. The traces of solvent were completely removed by using 1,4 dioxane (600 mL) followed by Toluene (300 mL) under reduced pressure at 85-90° C. The resulting residue was dissolved in toluene (360 mL) and given charcoal and sodium sulphate treatment then distilled up total solvent under reduced pressure at 95-100° C. and kept for traces removal for 2 hours at 95-100° C. to get 125 grams of the crude diisocyanate product as deep yellow thick syrup which was taken for further purification in 650 ml of 9:1 toluene: heptane mixture under nitrogen and heated up to 85-90° C. (mass temp) with thorough shaking and allow for settle the brown impurity layer at bottom and decant the top clear layer and given charcoal & sodium sulphate treatment for the clear decanted layer at 90-95° C. and filtered through hyflow and washed with toluene 100 ml, distilled up total solvent under reduced pressure and kept for traces removal under vacuum for 1 hour at 90-95° C. to get Diisocyanate as syrup and the resulted syrup was taken for next purification as follows. This purification procedure is repeated for one more time to get the pure diisocyanate (100 g) as deep yellow syrup (98.8% NCO). The resulting compound was characterized by $^1$H NMR (CDCl$_3$) δ0.84 (t, 3H, CH$_3$), 1.21-1.43 (m, 24H, 12×CH$_2$), 2.12 (t, 2H, COCH$_2$), 3.5 (m, 1H, CH) 5.12 (m, 1H, CH), 5.45 (m, 1H, CH), 7.12-7.32 (m, 4H, Ar) 7.85-8.15 (m, 4H, Ar). The hydrolytic degradation of the urethane prepared from this isocyanate was carried out in pH 9.0 buffer solution. The study showed that 1% solution is 100% hydrolyzed in 14 hours at 50° C.

Example 2
Diisocyanate from Ricinoleic Acid, Mono Glycolate Extended 4-Nitro-Phenol, and 4-Nitro-Benzoic Acid
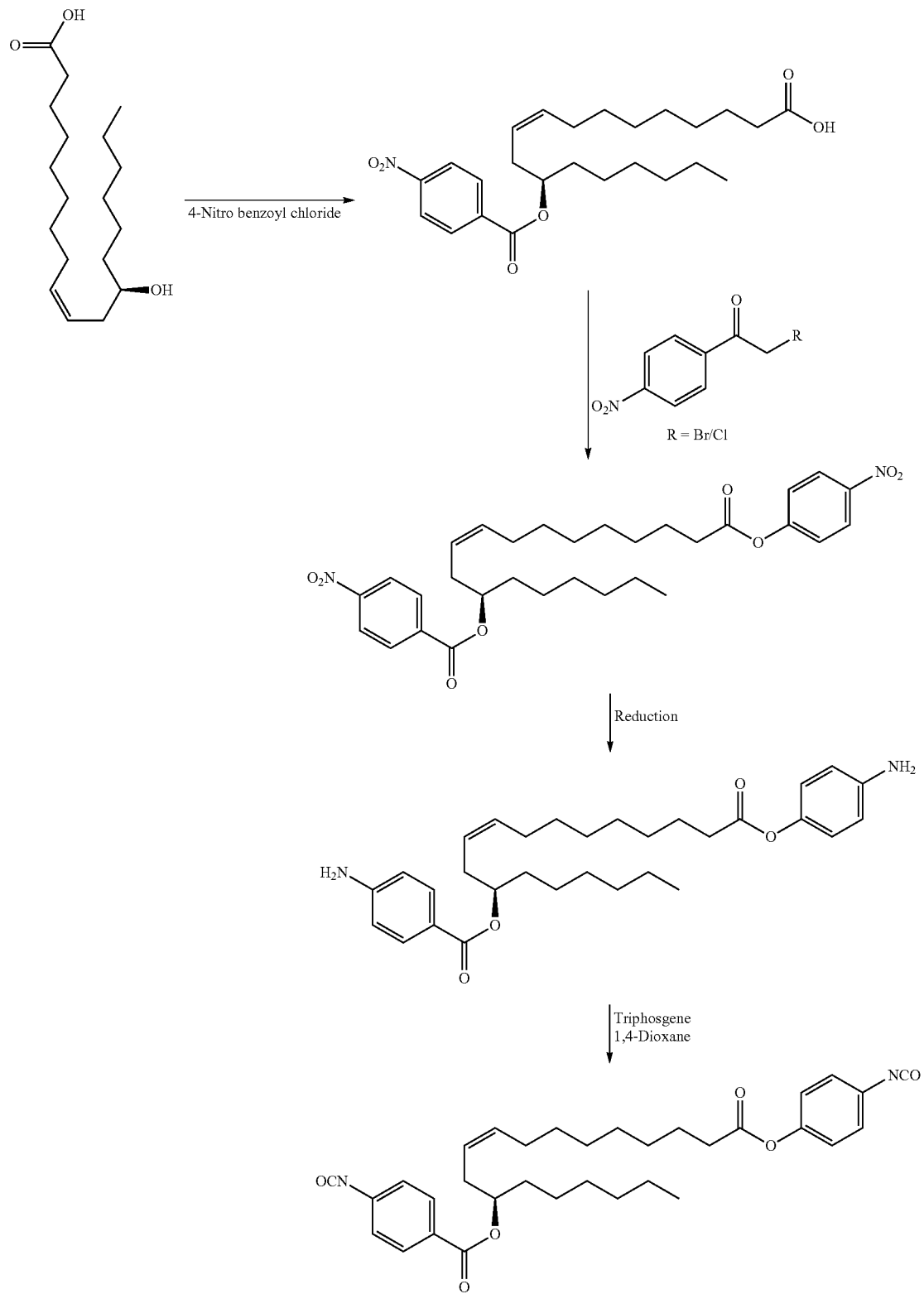

Example 3
Diisocyanate from Di-Glycolic Acid Extended Ricinoleic Acid, 4-Nitro Benzoic Acid, and 4-Nitro-Phenol
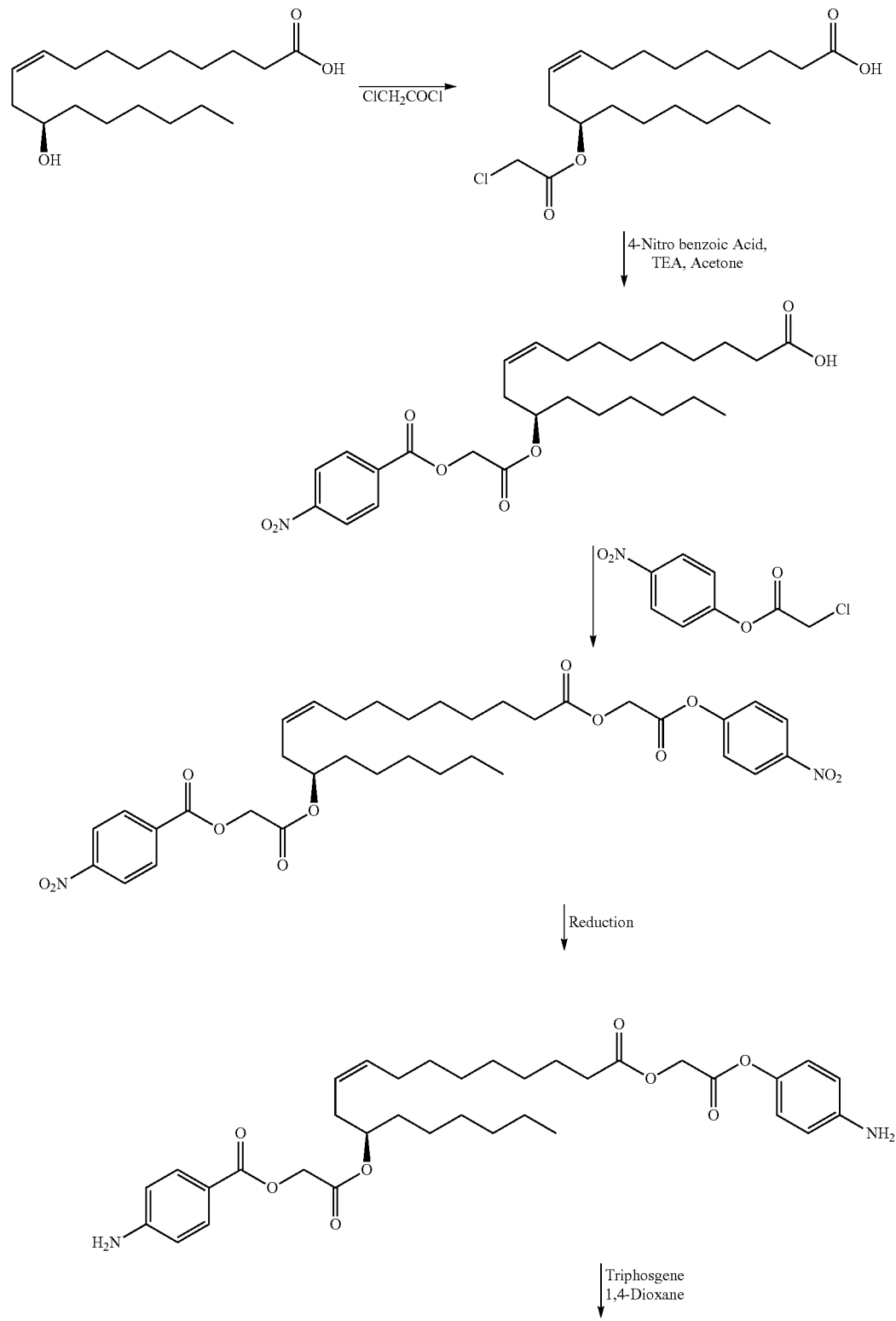

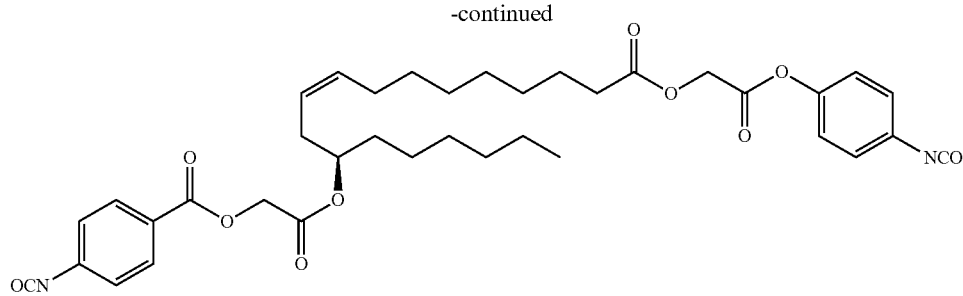

Example 4

Diisocyanate from 12-Hydroxy Stearic Acid, 4-Nitro-Benzoic Acid, and 4-Nitro-Phenol

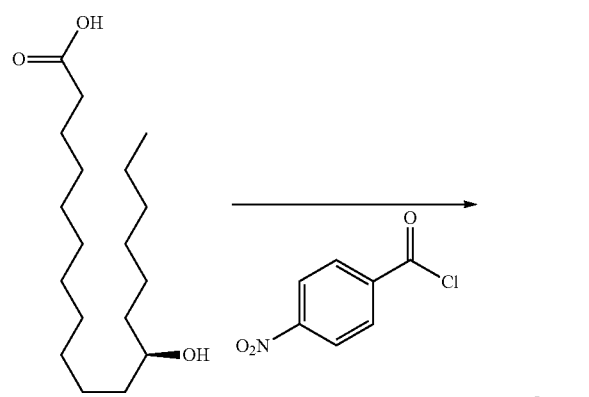

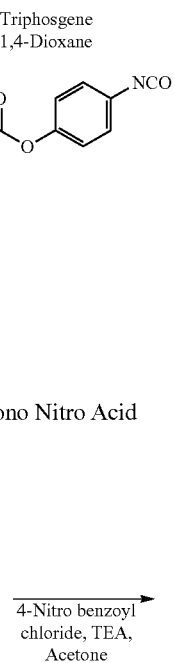

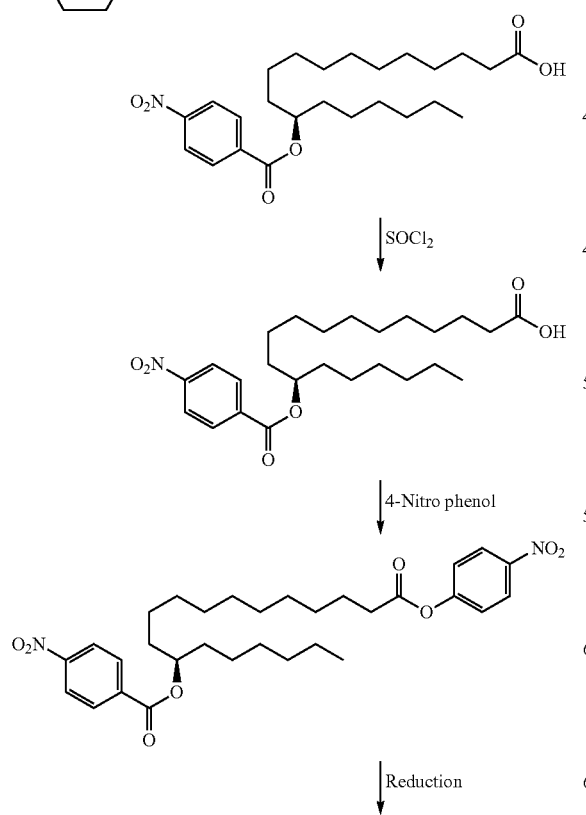

Example 4A

Synthesis of 12-Hydroxy Stearic Mono Nitro Acid

To a mixture of 12-Hydroxy stearic acid (450 grams, 1.5 moles), Triethylamine (313 ml, 2.35 moles) in Acetone (1 L) at 10-15° C., was added 4-Nitro Benzoyl Chloride (332 grams, 1.78 moles) and later stirred at room temperature for 10 hours. 75% of the solvent was distilled off. The resulting solution was cooled to room temperature and poured onto cold water. The pH of the solution was adjusted to 4-5 with dilute HCl, and resulting solid was filtered off and washed with chilled water. The solid was converted into slurry with 500 ml diisopropyl ether. The DIPE was filtered off and the resulting solid was dried in vacuum oven at 70-75° C. to yield pure 4-nitrobenzoic acid 11-carboxy-1-hexyl-undecyl ester product as white powder with a melting point of 98-101° C. The resulting compound was characterized by $^1$H NMR (DMSO-$d_6$) δ 0.85 (t, 3H, CH$_3$), 1.2-1.6 (m, 28H, 14×CH$_2$), 1.8 (m, 2H, CH$_2$), 2.32 (t, 2H, COCH$_2$), 3.2 (m, 1H, CH) 8.1-8.25 (m, 4H, Ar).

Example 4B

Synthesis of 12-Hydroxy Stearic Di-Nitro Compound

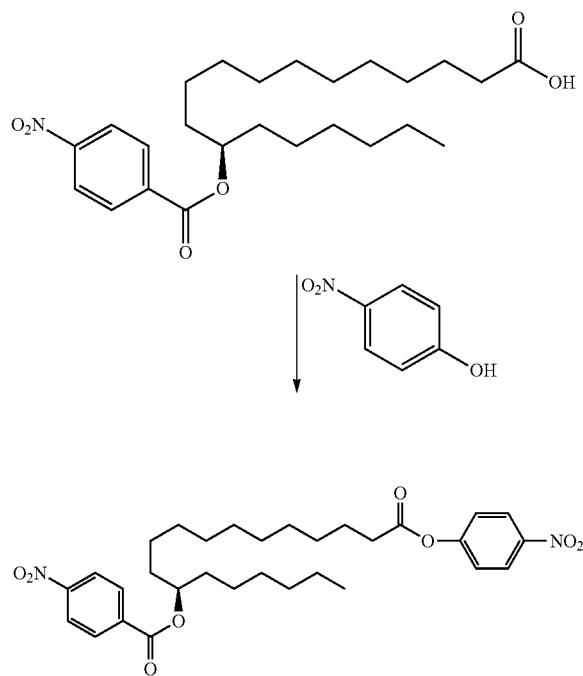

To a solution of 4-Nitro-benzoic acid 11-carboxy-1-hexyl-undecyl ester (350 g) in dry THF (2 L), Di-azabicycloundecane (DBU) (23 gr) at 5-10° C., was added a solution of N,N'Dicyclohexyl carbodiimide DCC (192 g) in 600 ml THF under nitrogen atmosphere, and later stirred at room temperature for 16-18 hours. DCU salts were filtered off and washed with tetrahydofuran. THF solvent was distilled off completely under reduced pressure at 60-65° C. and the resulting mass was poured into ice water (2 L). The resulting solid was filtered and washed with chilled water. The resulting crude was turned into slurry with 500 ml diisopropyl ether. DIPE was filtered off and then the material was dried in vacuum oven at 80-90° C. to yield pure 4-Nitro-benzoic acid 1-hexyl-11-(4-nitro-phenoxy carbonyl)-undecyl ester product as white powder with a melting point of 142-145° C. The resulting compound was characterized by $^1$H NMR (CDCl$_3$) δ 0.88 (t, 3H, CH$_3$), 1.3-1.6 (m, 26H, 13×CH$_2$), 1.78 (m, 2H, CH$_2$), 2.12 (t, 2H, COCH$_2$), 3.45 (m, 1H, CH), 7.52 (m, 2H, Ar) 7.75 (m, 1H, Ar) 8.3-8.52 (m, 5H, Ar).

Example 4C

Synthesis of 12-Hydroxy Stearic Diamino Compound

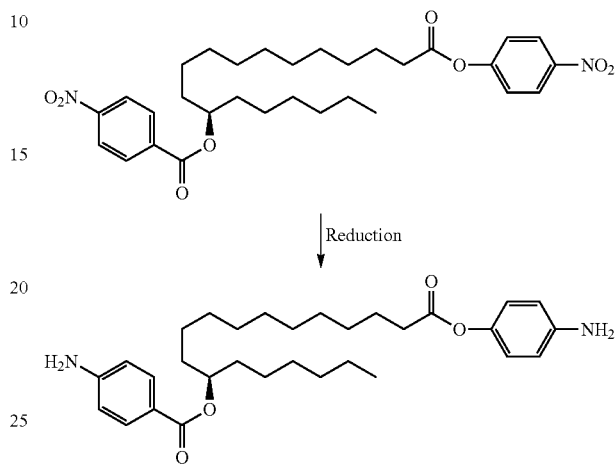

To a solution of 4-Nitro-benzoic acid 1-hexyl-11-(4-nitro-phenoxy carbonyl)-undecyl ester (290 g) in a mixture of Ethyl acetate (1.5 L) and DMF (300 mL) taken in a pressure vessel was added Raney Nickel (80 g). The reaction mixture was stirred under an atmosphere of Hydrogen (8-10 Kg) for 4 hours at a temperature of 60-65° C. The catalyst was removed by filtration. 75% of the solvent was distilled off and poured into cold water (2 L). The resulting solid was filtered off and washed with chilled water (100 mL) and do the slurry with 1 lit diisopropylether and filtered off, then dried the material properly in vacuum oven at 60-80° C. to yield pure 4-amino-benzoic acid 11-(4-amino-phenoxycarbonyl)-1-hexyl-undecyl ester product as off white powder (190 g) with a melting point of 156-159° C. The resulting compound was characterized by $^1$H NMR (CDCl$_3$) δ 0.83 (t, 3H, CH$_3$), 1.2-1.65 (m, 26H, 13×CH$_2$), 1.81 (m, 2H, CH$_2$), 2.12 (t, 2H, COCH$_2$), 3.50 (m, 1H, CH), 5.5-6.1 (m, 4H, 2×NH$_2$) 6.8-7.2 (m, 4H, Ar), 7.2-7.8 (m, 4H, Ar). The hydrolytic degradation of the compound was carried out in pH 9.0 buffer solution. The study showed that 1% solution is 100% hydrolyzed in 15 hours at 50° C.

Example 4D

Synthesis of 12-Hydroxy Stearic Diisocyanate

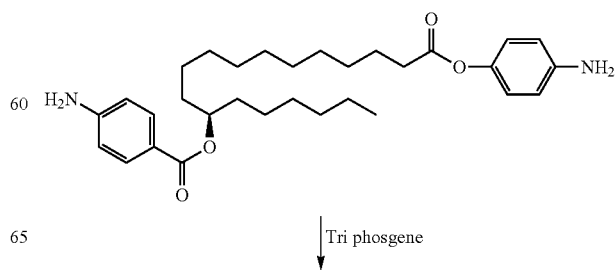

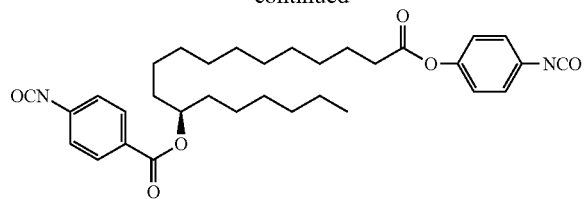

To a solution of 4-Amino-benzoic acid 11-(4-amino-phenoxycarbonyl)-1-hexyl-undecyl ester (180 g) in dry 1,4-dioxane (1.4 L) was added tri-phosgene (201 g) by dissolving in 360 ml of 1,4 dioxane. The solution was heated up to 60-65° C. followed by cooling to room temperature. The solution was again heated up to 100-105° C. and stirred for 3-4 hours. The solvent was distilled off completely under reduced pressure at 85-90° C. The traces were completely removed by using 1,4 dioxane followed by toluene (300 mL) under reduced pressure at 85-90° C. The resulting residue was dissolved in toluene and given charcoal and sodium sulphate treatment followed by distillation of the total solvent under reduced pressure at 95-100° C. and kept for removal of trace solvent for 2 hours at 95-100° C. to get 130 grams of the crude product as deep yellow thick syrup which was taken for further purification in 650 ml of 6:4 toluene: hexane mixture under nitrogen and heated up to 85-90° C. with thorough shaking. The resulting solution was allowed to sit to enable brown impurity layer to settle down at bottom. The top clear layer was decanted off and given charcoal & sodium sulphate treatment for the clear decanted layer at 90-95° C. and filtered and washed with toluene. The solvent was distilled off under reduced pressure and kept for removal of trace solvent under vacuum for 1 hour at 90-95° C. It was then allowed to cool to 40-45° C. and added 200 ml of dry n-Hexane and cooled to 0-5° C. under nitrogen with proper stirring for 30 minutes with glass rod in a beaker. The resulting solid was filtered off to yield the pure diisocyanate as off white powder 85 grams (99.25% NCO) with a melting point of 98-101° C. The product was characterized by $^1$H NMR (CDCl$_3$) δ 0.82 (t, 3H, CH$_3$), 1.21-1.43 (m, 26H, 13×CH$_2$), 1.83 (m, 2H, CH$_2$), 2.12 (t, 2H, COCH$_2$), 3.82 (m, 1H, CH), 7.12-7.32 (m, 4H, Ar) 7.75-8.15 (m, 4H, Ar). The hydrolytic degradation of the urethane prepared from this isocyanate was carried out in pH 9.0 buffer solution. The study showed that 1% solution is 100% hydrolyzed in 16 hours at 50° C.

Example 5

Diisocyanate from 12-Hydroxy Stearic Acid, Mono-Glycolate Extended-4-Nitro Phenol, and 4-Nitro-Benzoic Acid

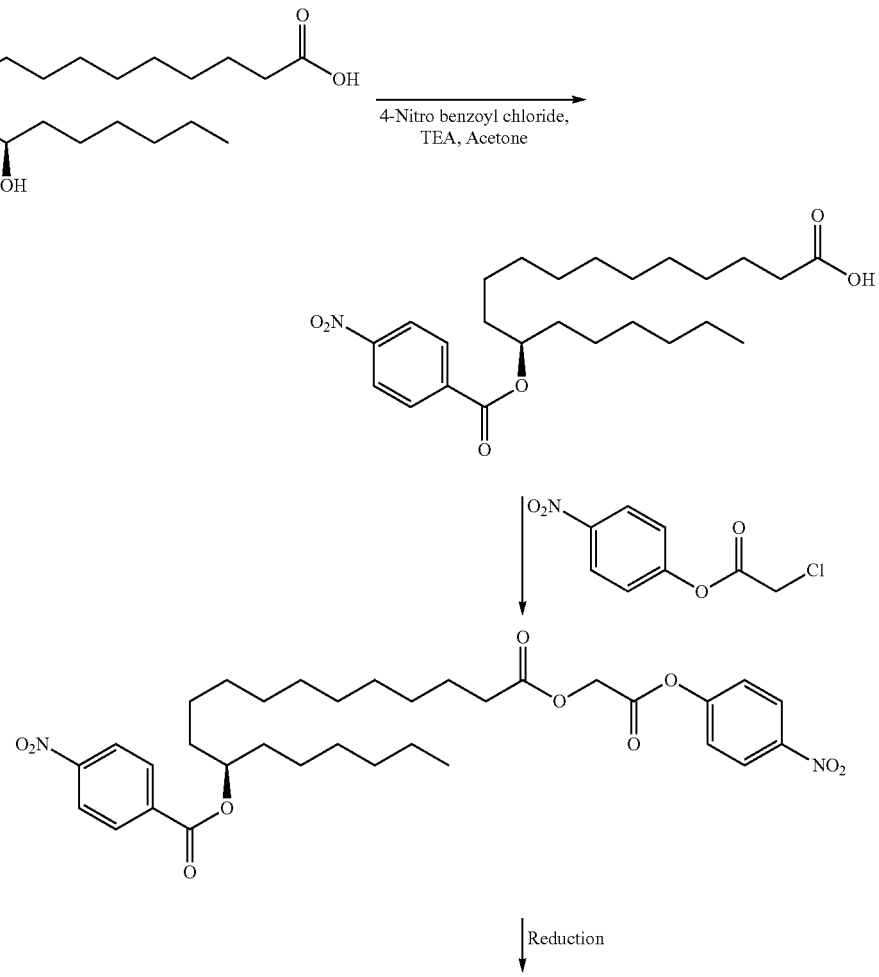

-continued

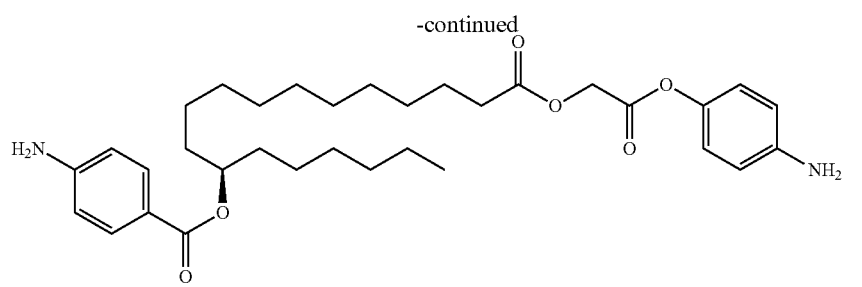

↓ Triphosgene
1,4-Dioxane

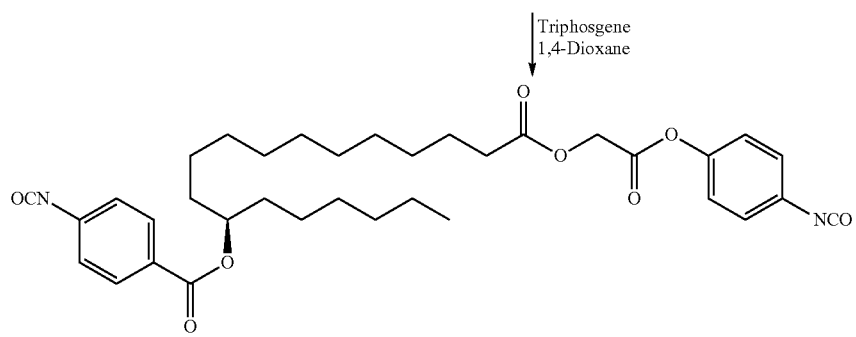

Example 5A

Synthesis of Dinitro 12-Hydroxy Stearic Monoglycolate

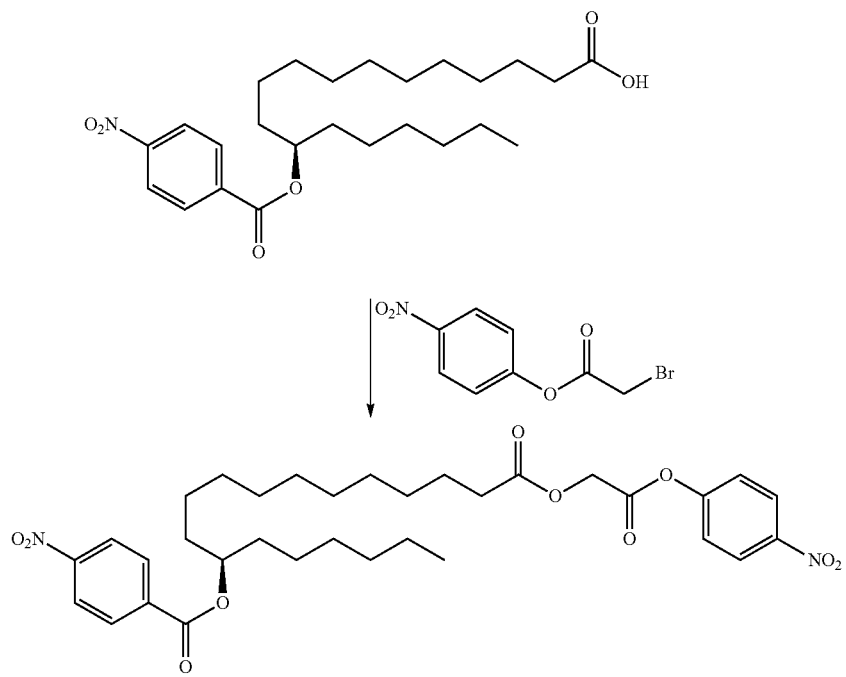

To a solution of 4-Nitro-benzoic acid 11-carboxy-1-hexyl-undecyl ester (500 g) in dry Acetone, triethylamine (232 mL) at 10-15° C. was added Bromoacetic acid 4-nitro-phenyl ester (347 g). The solution was stirred at room temperature for 8 hours. 75% of the solvent was distilled off and cooled to room temperature. The resulting solid was poured onto cold water and pH was adjusted to 4-5 with dilute HCl. The resulting solid was filtered off and washed with chilled water (100 mL). The slurry was prepared with 1 lit Di Isopropyl Ether and filtered off. The resulting solid was then dried in vacuum oven at 60-80° C. to yield pure (R)-18-(2-(4-nitrophenoxy)-2-oxo-ethoxy)-18-oxooctadecan-7-yl 4-nitrobenzoate product as off white powder with a melting point of 130-133° C. The resulting compound was characterized by $^1$H NMR (CDCl$_3$) δ 0.86 (t, 3H, CH$_3$), 1.2-1.5 (m, 28H, 14×CH$_2$), 1.68 (m, 2H, CH$_2$), 2.42 (t, 2H, COCH$_2$), 3.52 (m, 1H, CH), 5.2 (s, 2H, CH$_2$) 7.42 (m, 2H, Ar) 8.4-8.52 (m, 6H, Ar).

Example 5B

Synthesis of 12-Hydroxy Stearic Monoglycolate Diamine

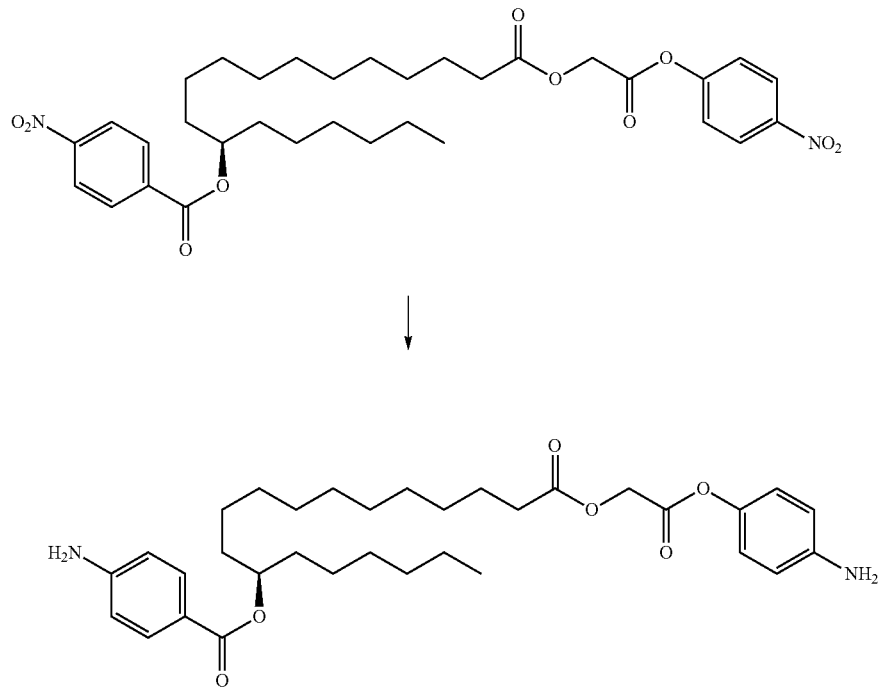

To a solution of (R)-18-(2-(4-nitrophenoxy)-2-oxoethoxy)-18-oxo octadecan-7-yl 4-nitrobenzoate (380 g) in a mixture of Ethyl acetate (1.5 L) and DMF (300 mL) taken in a pressure vessel was added Raney Nickel (100 g). The resulting mixture was stirred under an atmosphere of hydrogen (8-10 Kg) for 4 hours at a temperature of 60-65° C. The catalyst was removed by filtration. The solvent was distilled off by 75%, poured onto cold water (2 L) and filtered off the resulted solid and wash with chilled water (100 mL) and do the slurry with 1 lit Di Isopropyl Ether and filtered off, then dry the material properly in vacuum oven at 60-80° C. to yield pure (R)-18-(2-(4-amino phenoxy)-2-oxoethoxy)-18-oxooctadecan-7-yl 4-amino benzoate product as off white powder (190 g) with a melting point of 124-127° C. The resulting compound was characterized by $^1$H NMR (CDCl$_3$) δ 0.83 (t, 3H, CH$_3$), 1.2-1.65 (m, 28H, 14×CH$_2$), 1.71 (m, 2H, CH$_2$), 2.42 (t, 2H, COCH$_2$), 3.50 (m, 1H, CH), 5.12 (s, 2H, CH$_2$) 6.12 (m, 2H, Ar), 6.52 (m, 4H, 2×NH$_2$) 6.9-7.52 (m, 6H, Ar). The hydrolytic degradation of the compound was carried out in pH 9.0 buffer solution. The study showed that 1% solution is 100% hydrolyzed in 9 hours at 50° C.

Example 14

Synthesis of 12-Hydroxy Stearic Monoglycolate Diisocyanate

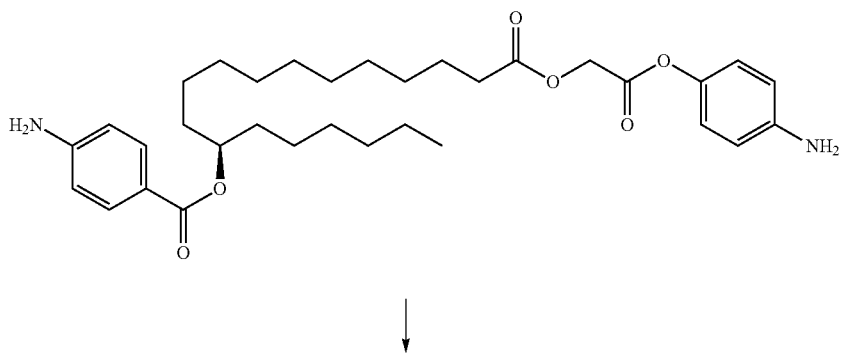

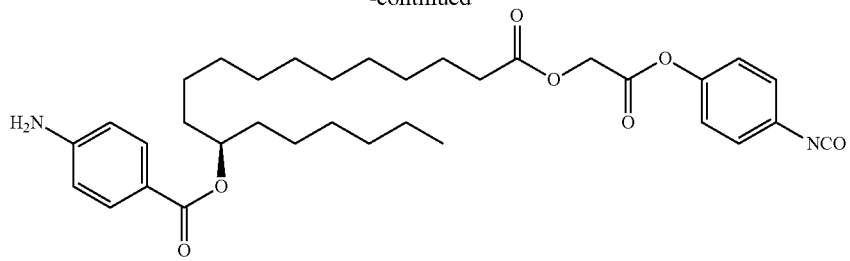

To a solution of (R)-18-(2-(4-amino phenoxy)-2-oxoethoxy)-18-oxo octadecan-7-yl 4-amino benzoate (180 g) in dry 1,4-dioxane (1.4 lit) Tri phosgene (160 g) was added by dissolving in 320 ml 1,4 dioxane after heated up to 60-65° C. followed by cooling to room temperature at which temperature the mass became clear solution, then again heated up to 100-105° C. and stirred for 3-4 hours, solvent was distilled off completely under reduced pressure at 80-85° C., then remove the traces completely by using 1,4 dioxane followed by Toluene (300 mL) under reduced pressure at 85-90° C., then resulted residue was dissolved in Toluene 350 ml and given charcoal and sodium sulphate treatment then distilled up total solvent under reduced pressure at 95-100° C. and kept for traces removal for 2 hours at 95-100° C. to get 150 grams of the crude product as deep yellow syrup that was taken for further purification in 750 ml of 6:4 toluene: hexane mixture under nitrogen and heated up to 85-90° C. and allow for settle the brown impurity layer at bottom and decant the top clear layer and given charcoal & sodium sulphate treatment for the clear layer at 90-95° C. and filtered and washed with toluene 100 ml. The solvent was distilled off under reduced pressure and kept for removal of trace solvent under vacuum for 1-2 hours at 90-95° C. This purification procedure is repeated for one more time to get the pure diisocyanate as deep yellow syrup 95 grams (99.1% NCO). The resulting compound was characterized by $^1$H NMR (CDCl$_3$) δ 0.81 (t, 3H, CH$_3$), 1.21-1.63 (m, 28H, 14×CH$_2$), 1.73 (m, 2H, CH$_2$), 2.22 (t, 2H, COCH$_2$), 3.62 (m, 1H, CH), 5.22 (s, 2H, CH$_2$) 7.15-7.52 (m, 8H, Ar). The hydrolytic degradation of the urethane prepared from this isocyanate was carried out in pH 9.0 buffer solution. The study showed that 1% solution is 100% hydrolyzed in 12 hours at 50° C.

Example 6

Diisocyanate from 12-Hydroxy Stearic Acid, Di-Glycolic Acid Extented, 4-Nitro Benzoic Acid, and 4-Nitro Phenol

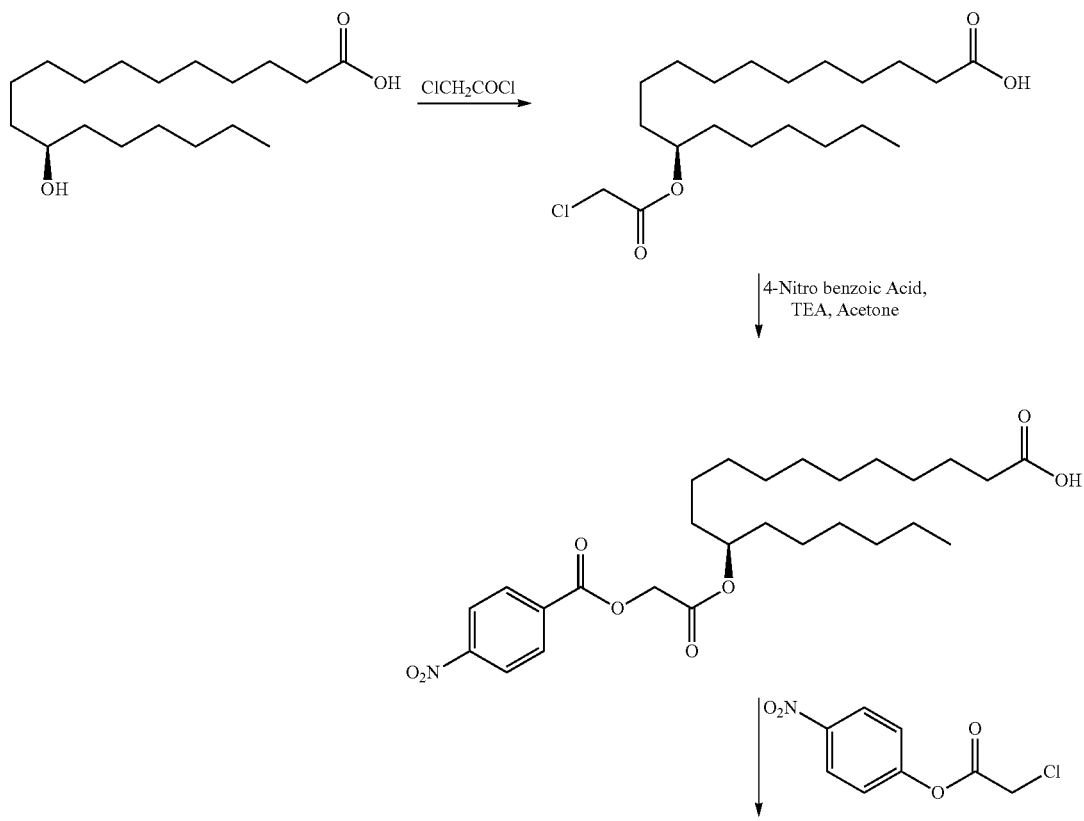

-continued
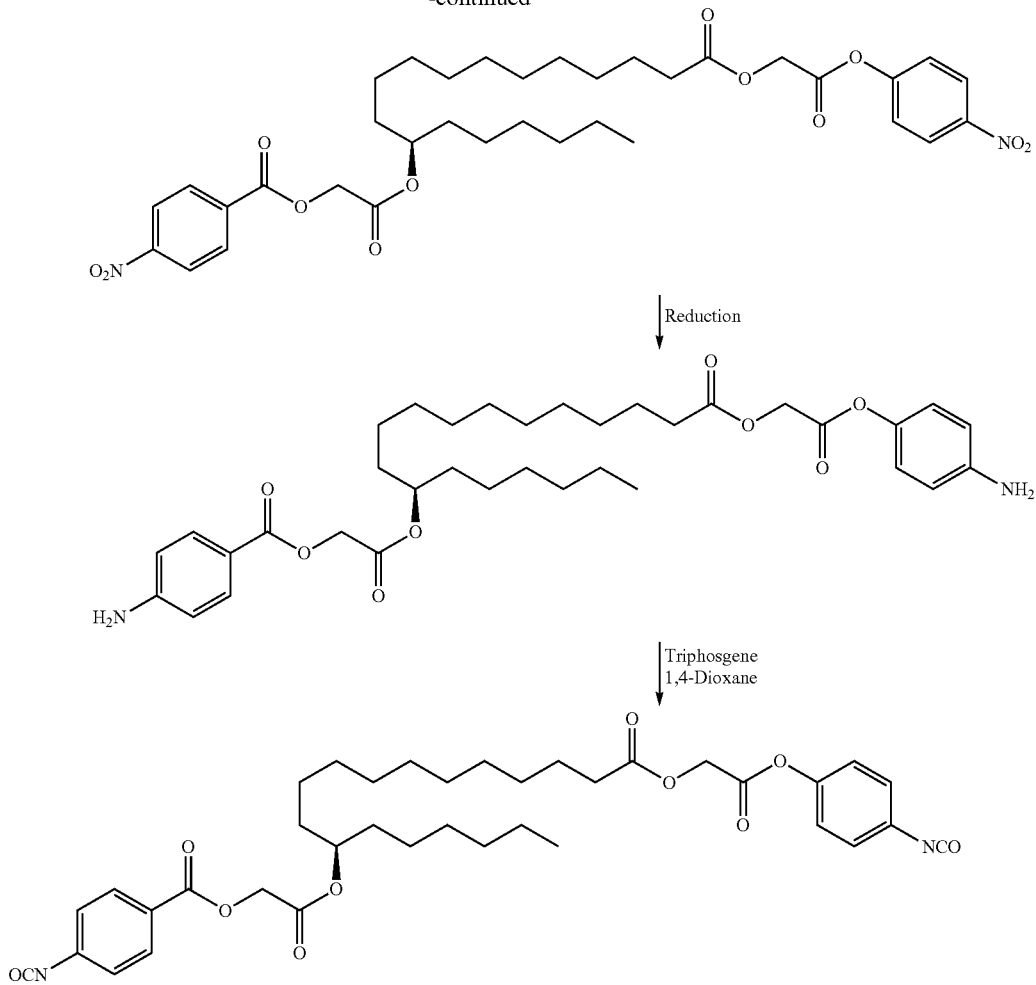
Example 7
Diisocyanate from 12-Hydroxy Stearic-Succinate is Prepared Using the Following Scheme
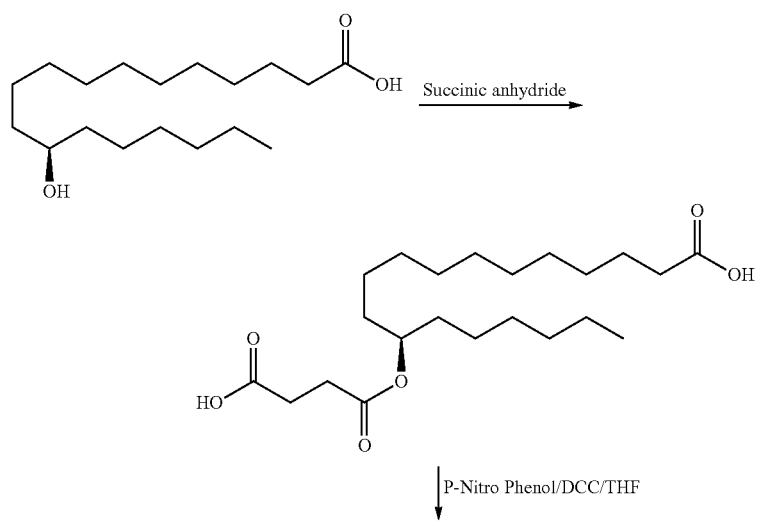

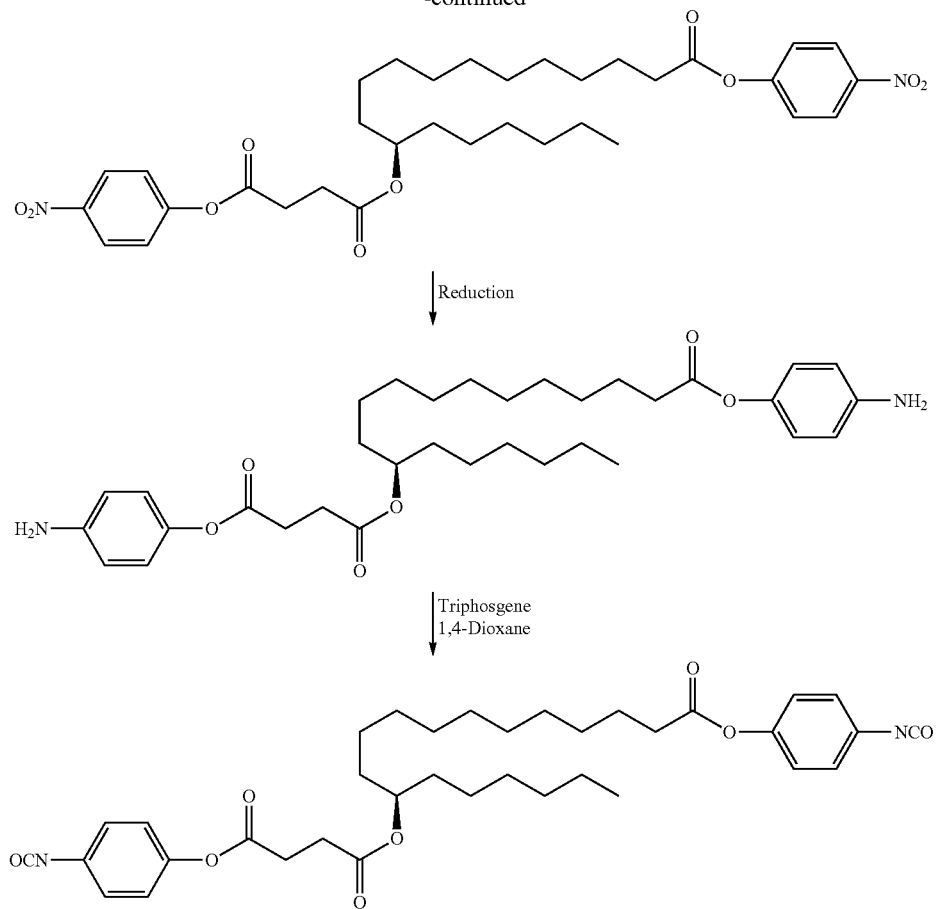
Example 8
Diisocyanate from Ricinoleic Acid-Succinate Prepared According to the Following Scheme
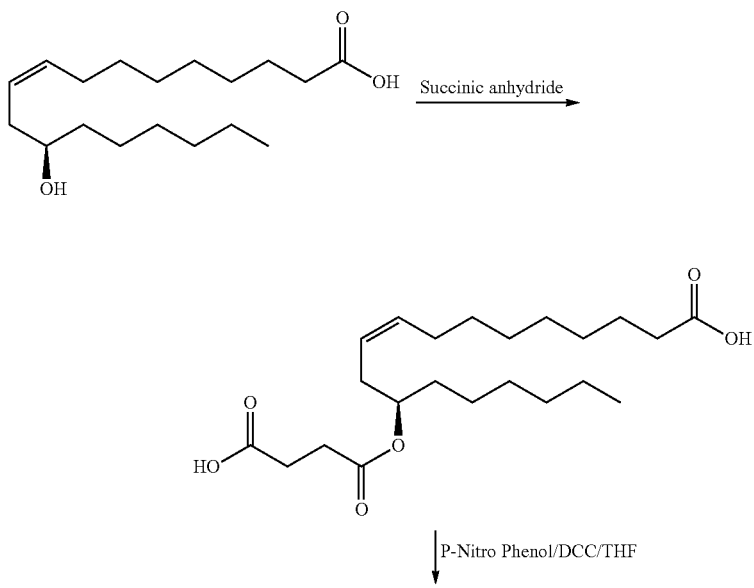

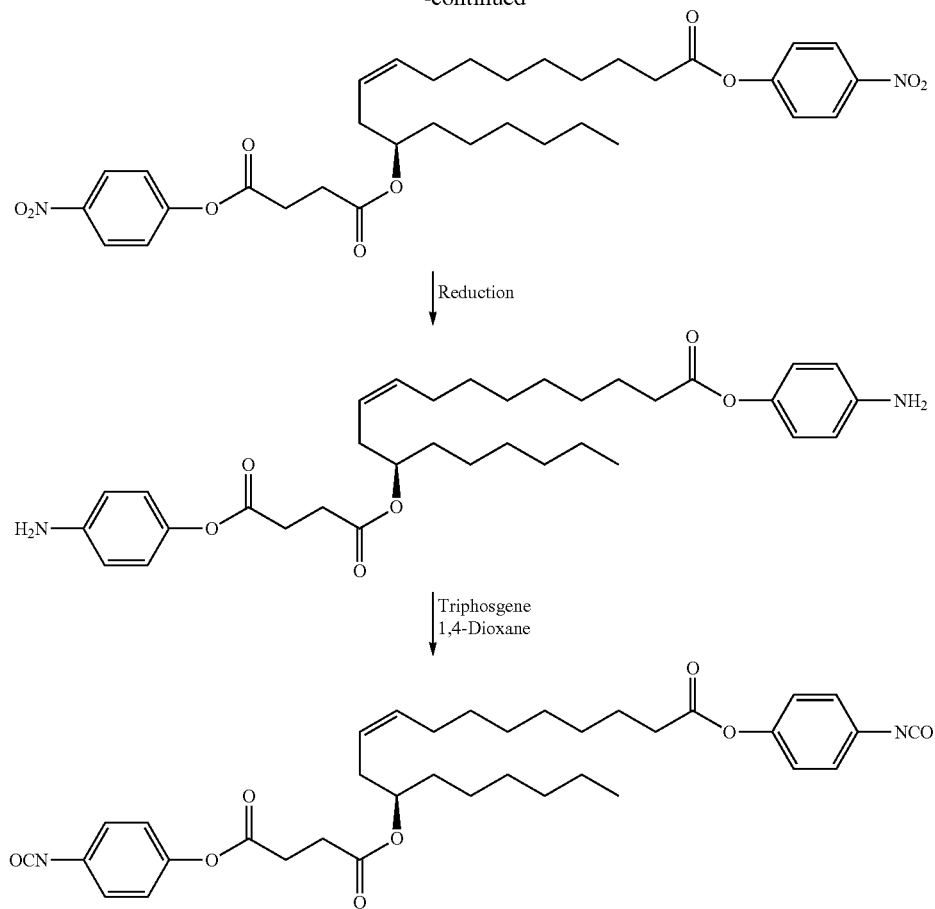
Example 9
Diisocyanate from Ricinoleic Acid-Diglycolic Anhydride Prepared According to the Following Scheme
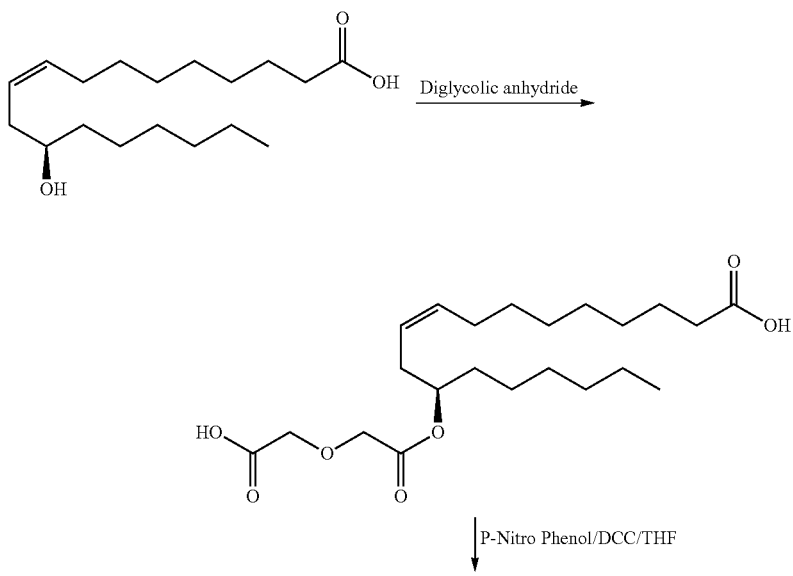

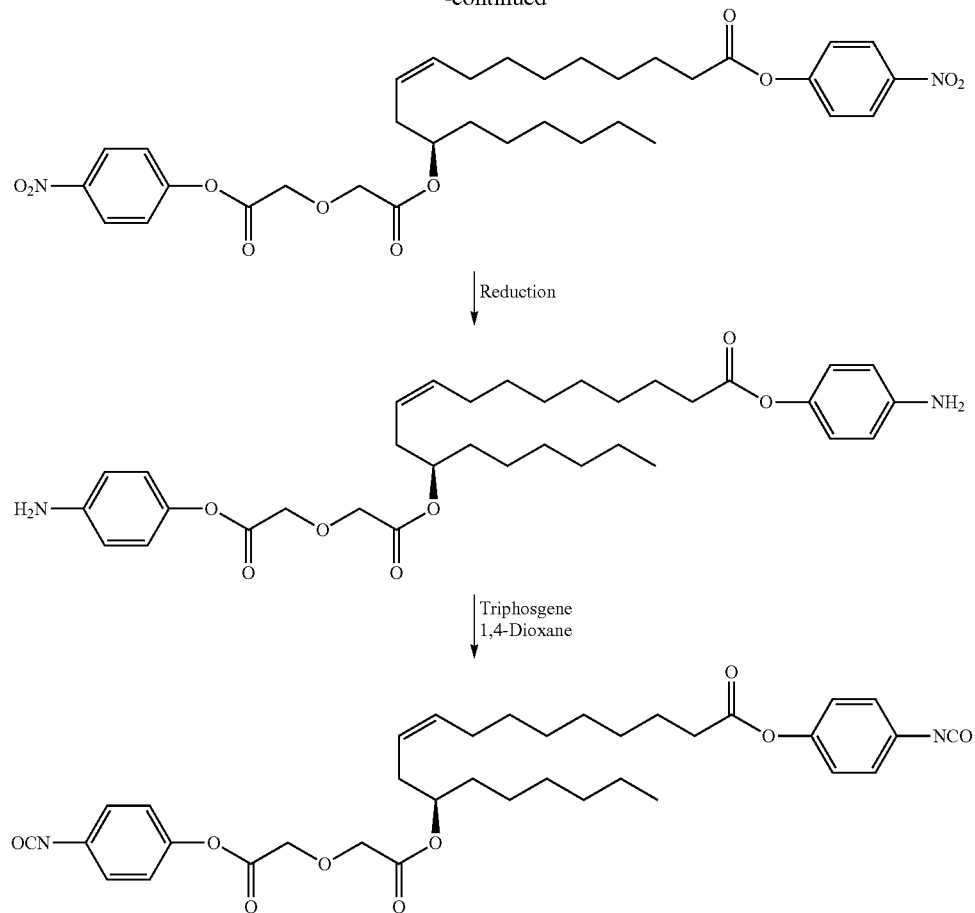
Example 10
Diisocyanate from 12 Hydroxystearic Acid-Diglycolic Anhydride Prepared According to the Following Scheme
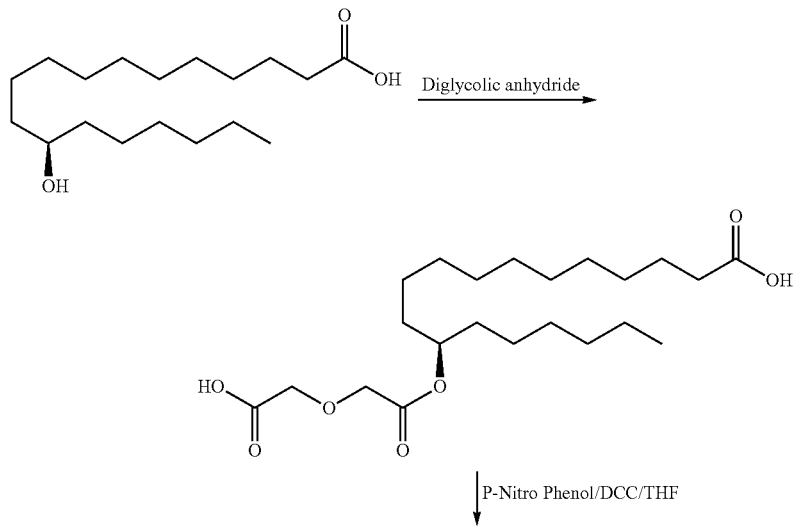

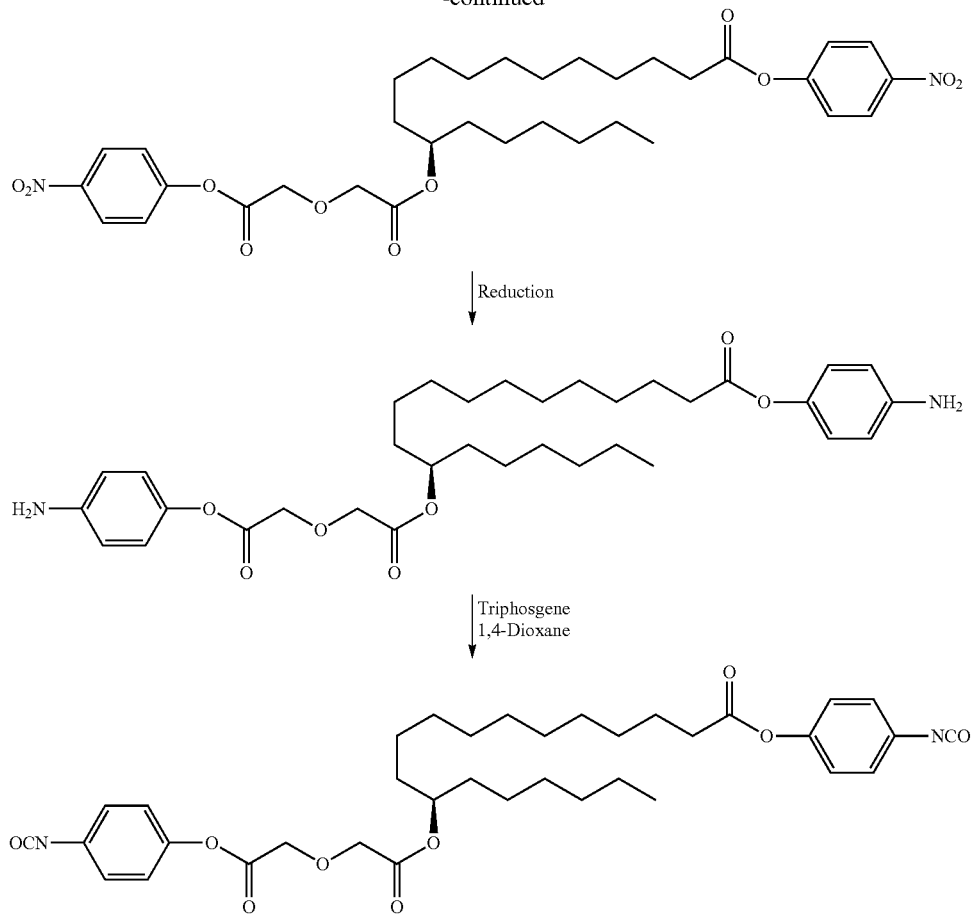
Numerous modifications and variations of the present invention are possible in light of the above teachings. It is therefore to be understood that within the scope of the appended claims, the invention may be practiced otherwise that as specifically described herein.
What is claimed is:
1. A diisocyanate selected from formula (I), (II), or (III):
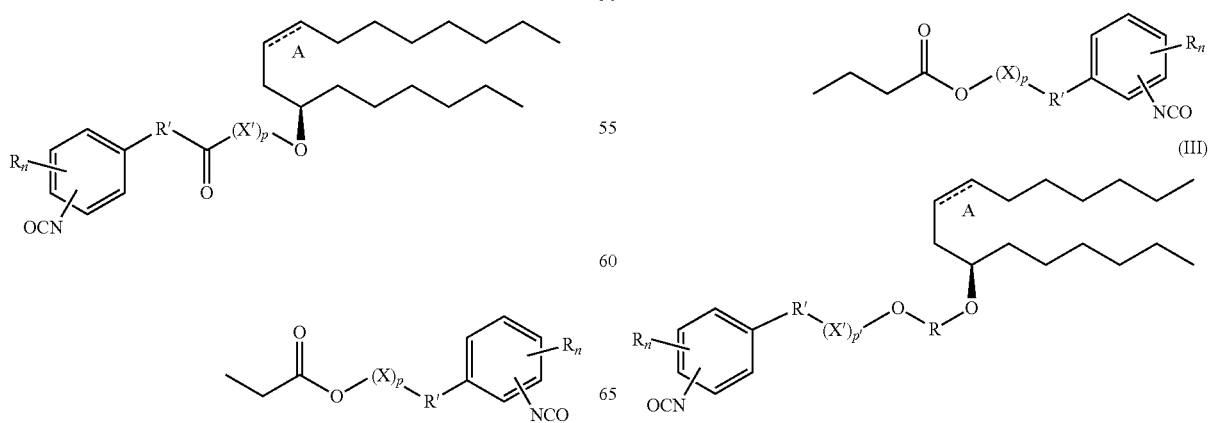

-continued

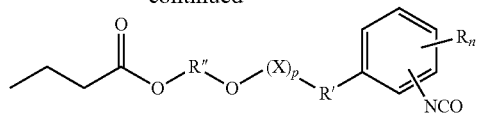

wherein:
variable A, the dashed bond, is absent or is a double bond;
each R is independently the diacyl residue of a diacid;
R' is absent or each R' is independently a $C_{1-6}$ alkylene group;
R" is the residue of a diol or polyol;
from 1-4 $R_n$ are present;
each $R_n$ is independently selected from: H, $C_{1-6}$ alkyl, $C_{1-6}$ alkoxy, benzyloxy, halogen, —CHO, —$CO_2H$, and —$NO_2$, and each $R_n$ is independently attached directly to aromatic ring or attached through a —$(CH_2)_{1-4}$— linker;

each X independently is selected from:
- —$CH_2COO$— (glycolic acid moiety);
- —$CH(CH_3)COO$— (lactic acid moiety);
- —$CH_2CH_2OCH_2COO$— (dioxanone moiety); and,
- —$CH_2CH_2CH_2CH_2CH_2COO$— (caprolactone moiety);

each X' independently is selected from:
- —$OCH_2CO$— (glycolic acid moiety);
- —$OCH(CH_3)CO$— (lactic acid moiety);
- —$OCH_2CH_2OCH_2CO$— (dioxanone moiety); and,
- —$OCH_2CH_2CH_2CH_2CH_2CO$— (caprolactone moiety);

each p is independently selected from 0, 1, 2, 3, 4, 5, and 6; and,
each p' is independently selected from 0, 1, 2, 3, 4, 5, and 6;
provided that p+p' total from 2-6.

2. The diisocyanate of claim 1, wherein the diisocyanate is selected from formulae (Ia)-(IIIa):

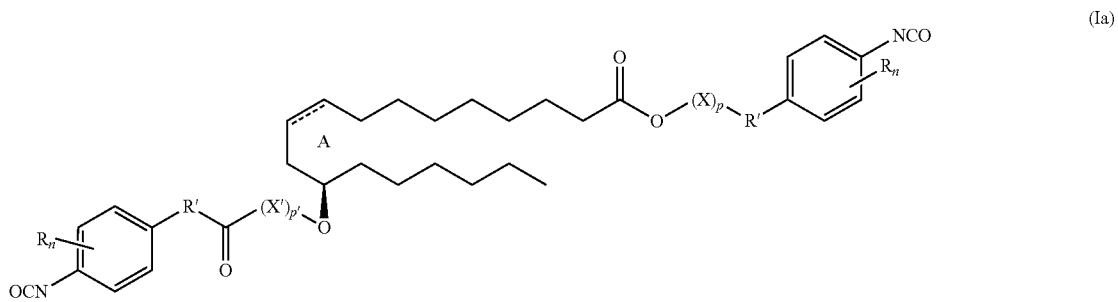

(Ia)

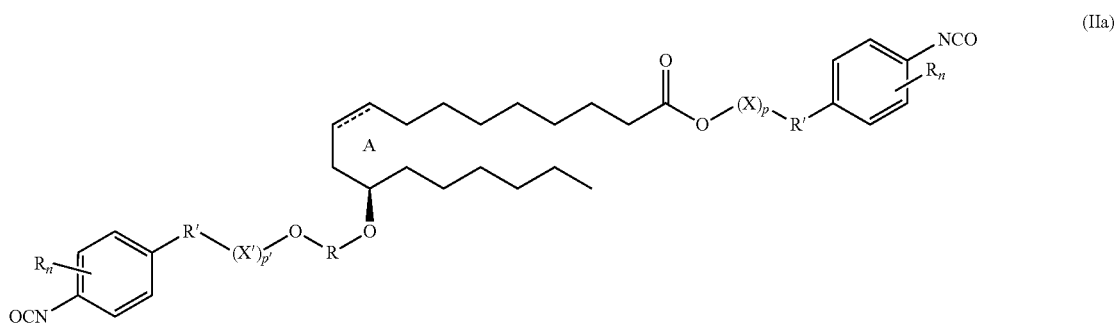

(IIa)

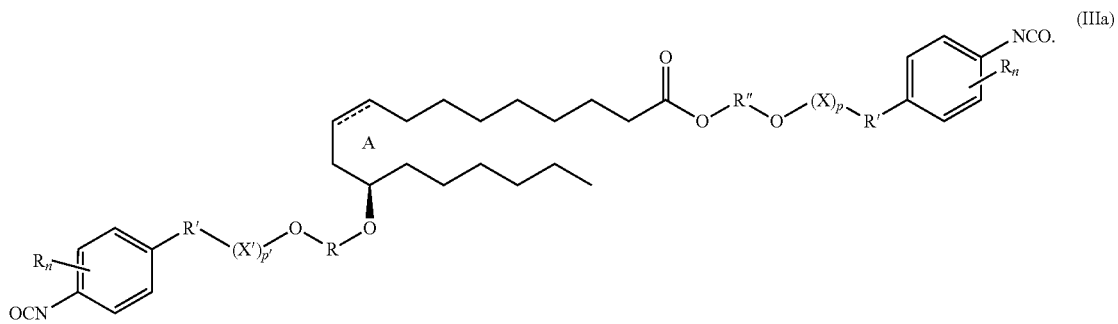

(IIIa)

3. The diisocyanate of claim 1, wherein the diisocyanate is selected from formulae (Ia₁)-(IIIa₂):
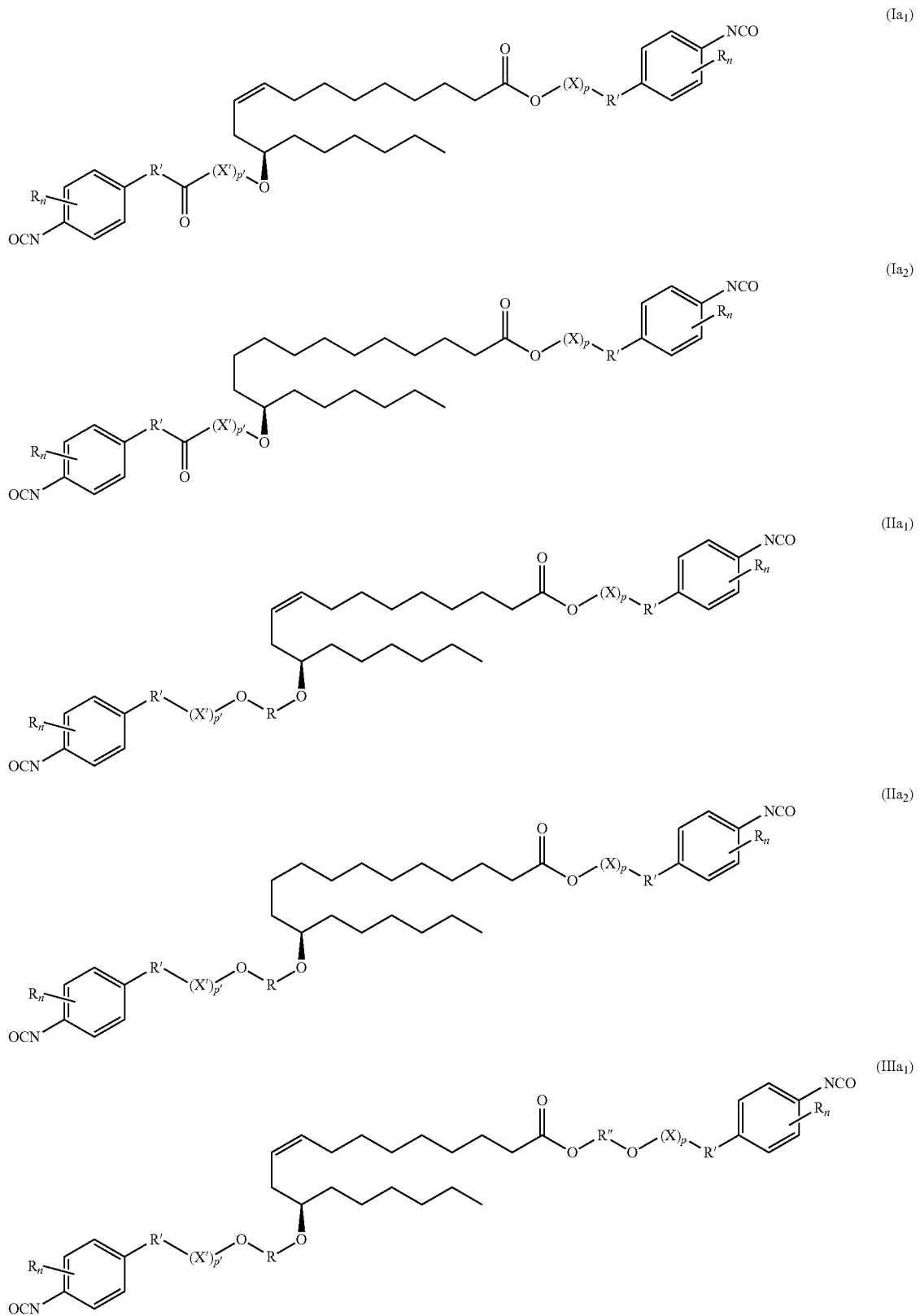

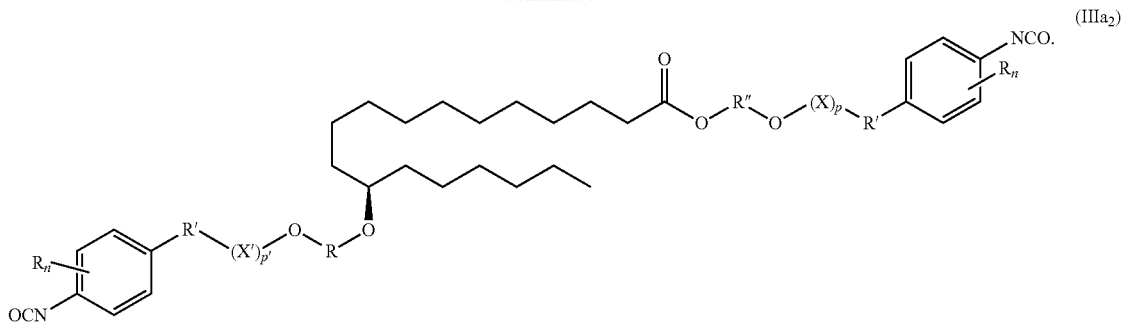
(IIIa₂)
4. The diisocyanate of claim 1, wherein the diisocyanate is selected from formulae (Ia₁ₐ)-(IIIa₂ₐ):
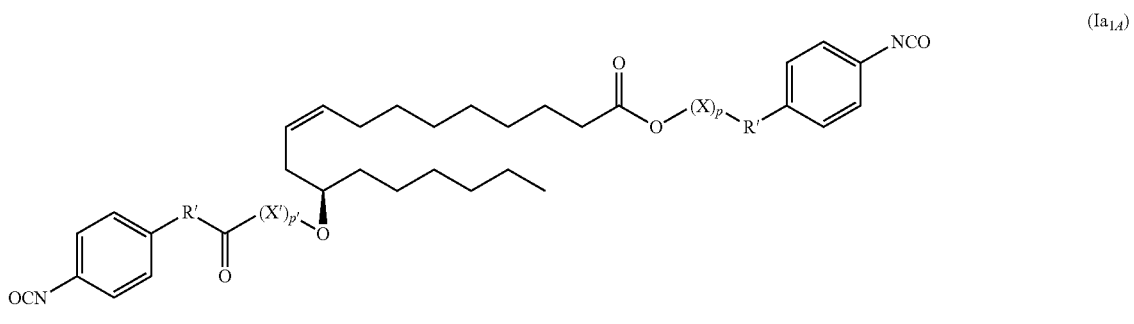
(Ia₁ₐ)
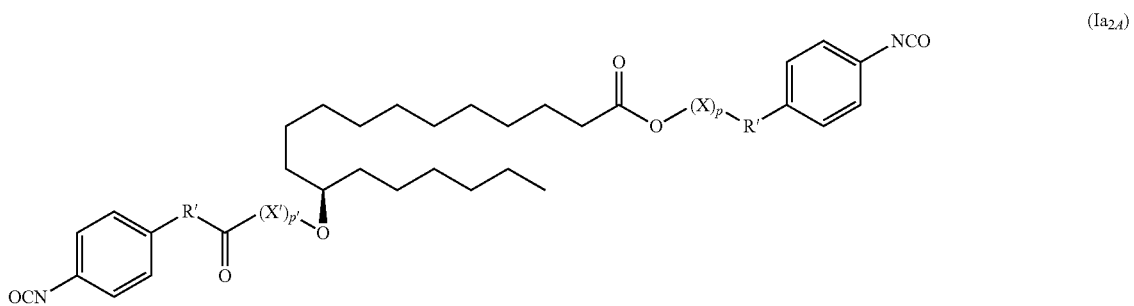
(Ia₂ₐ)
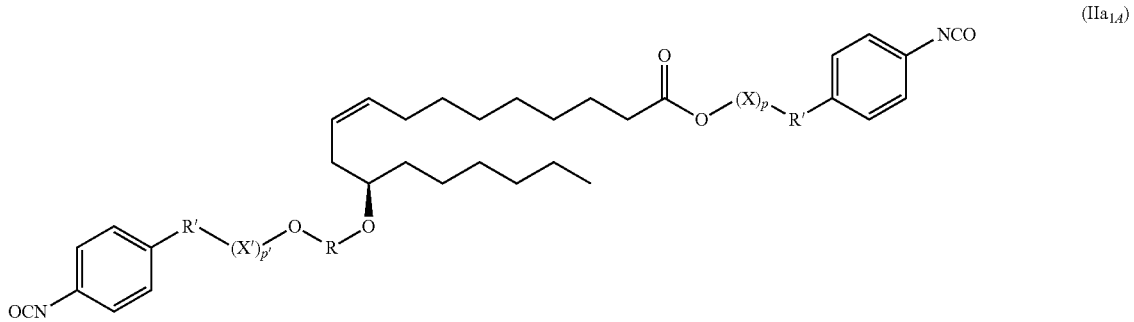
(IIa₁ₐ)

-continued
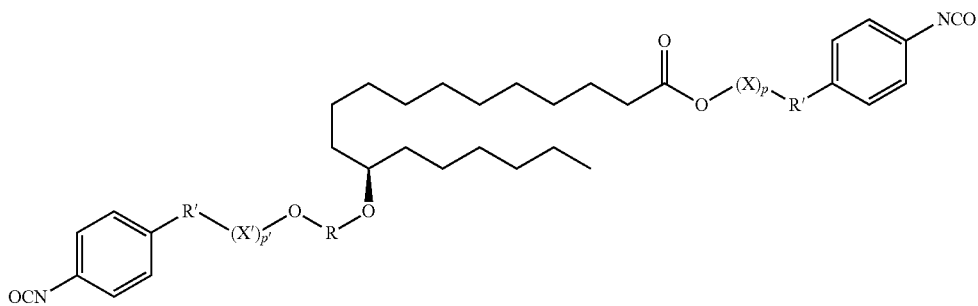
(IIa<sub>2A</sub>)
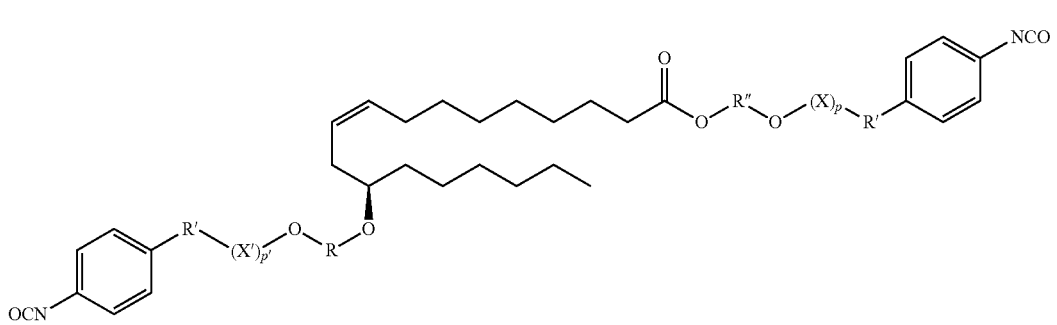
(IIIa<sub>1A</sub>)
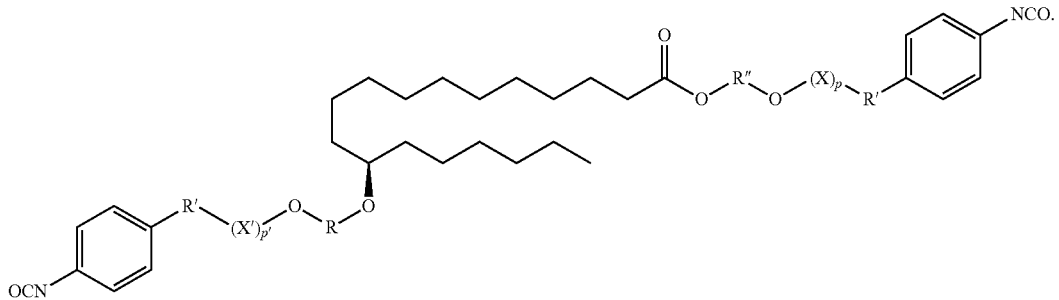
(IIIa<sub>2A</sub>).
5. The diisocyanate of claim 1, wherein the diisocyanate is selected from formulae (1)-(20):
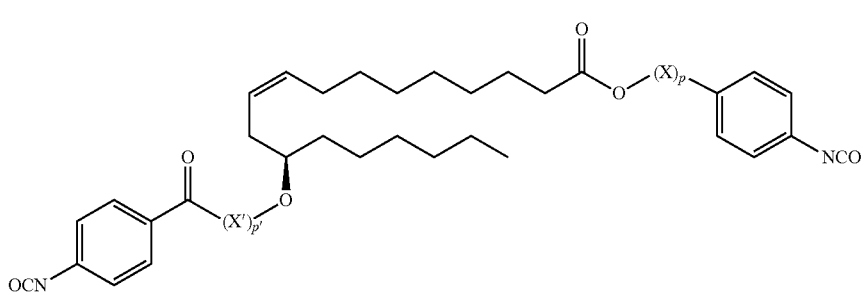
(1)
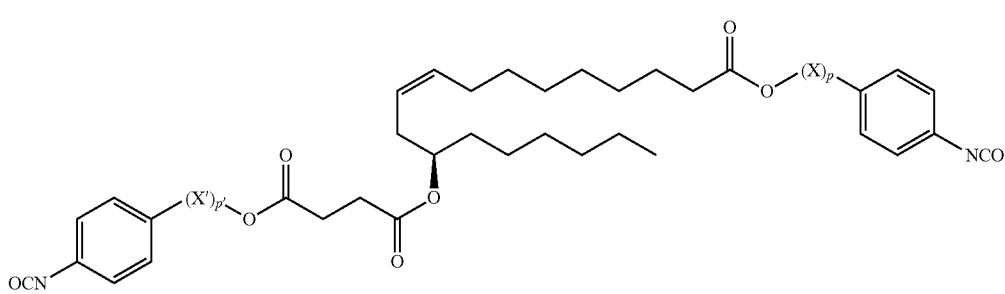
(2)

-continued
(3)
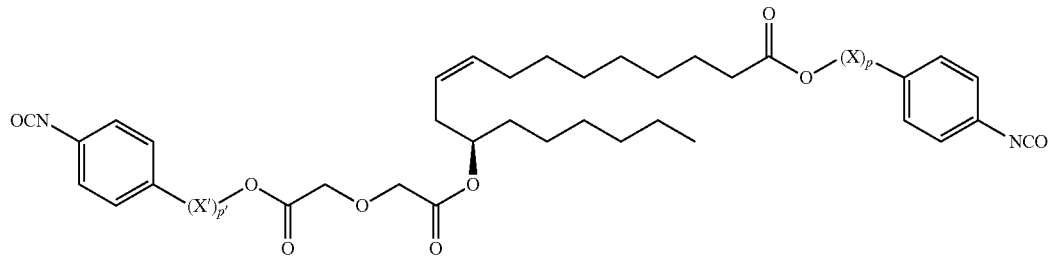
(4)
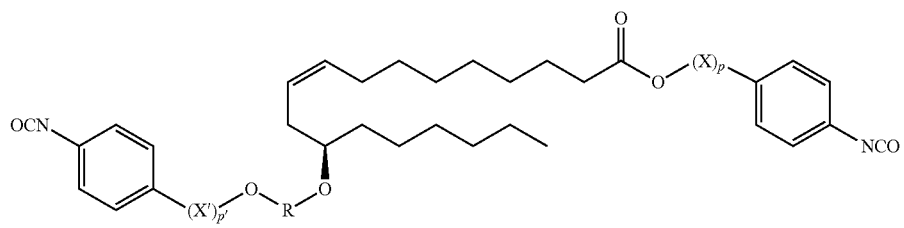
(5)
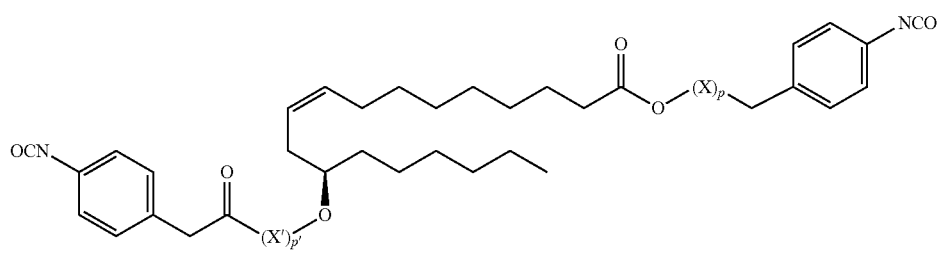
(6)
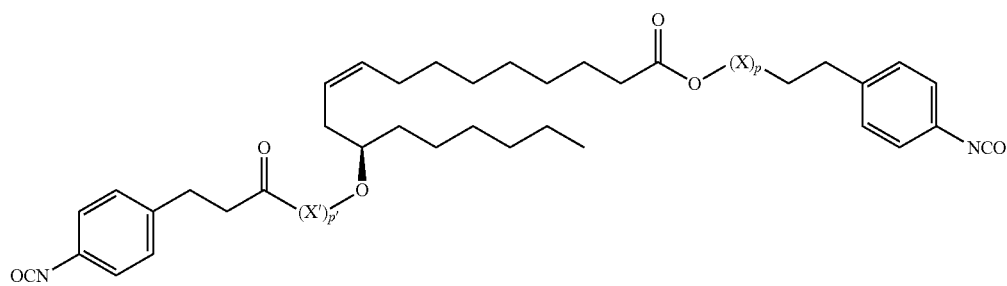
(7)
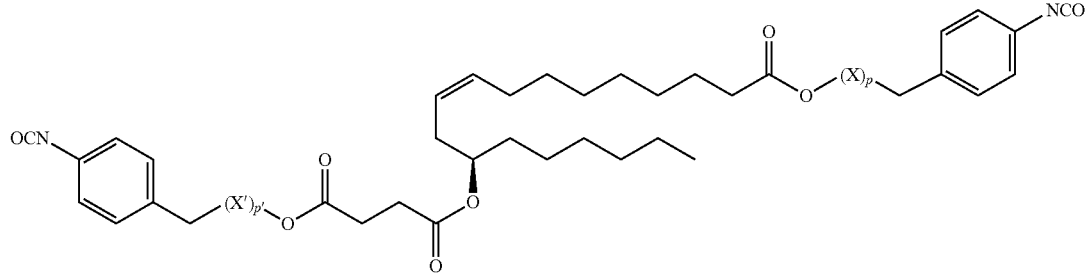
(8)
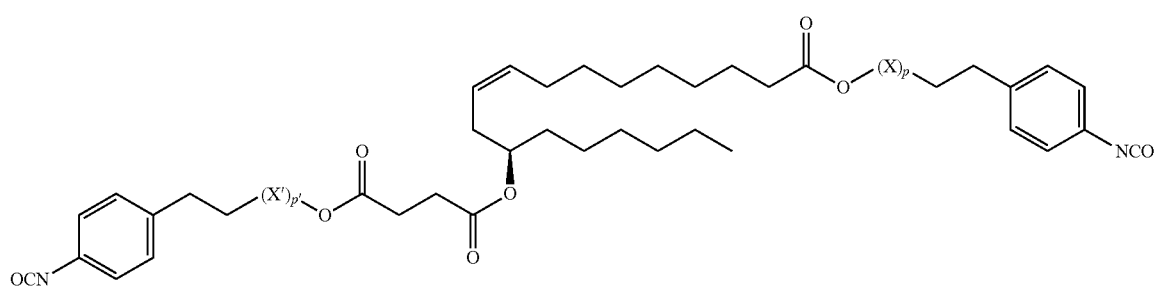

-continued
(9)
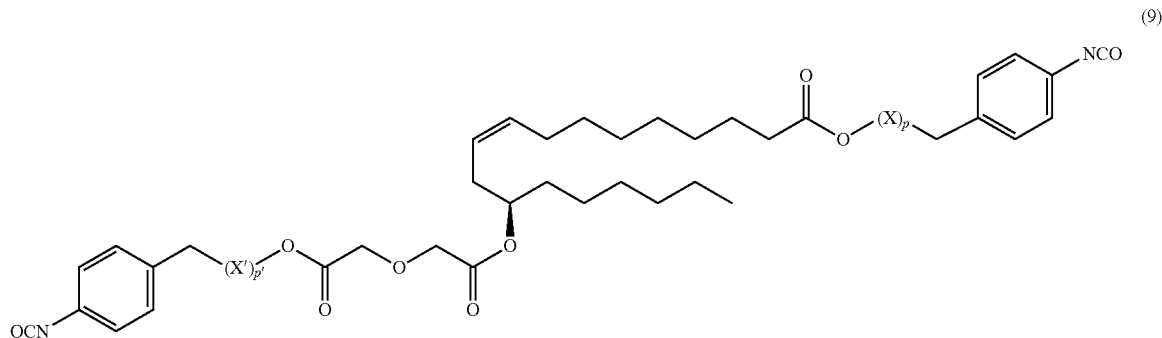
(10)
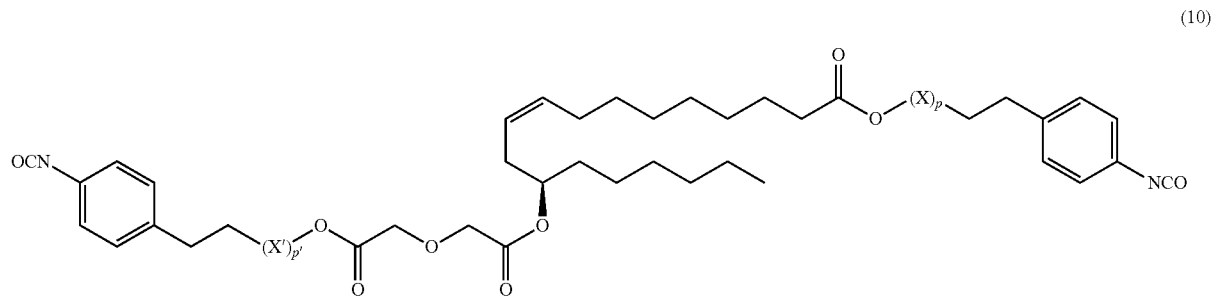
(11)
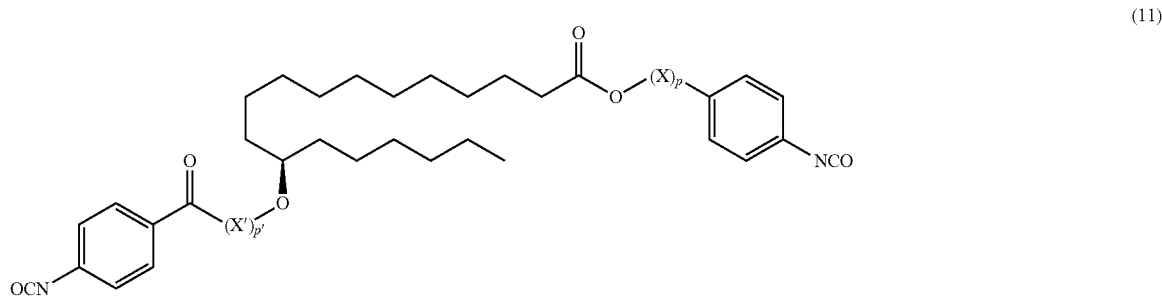
(12)
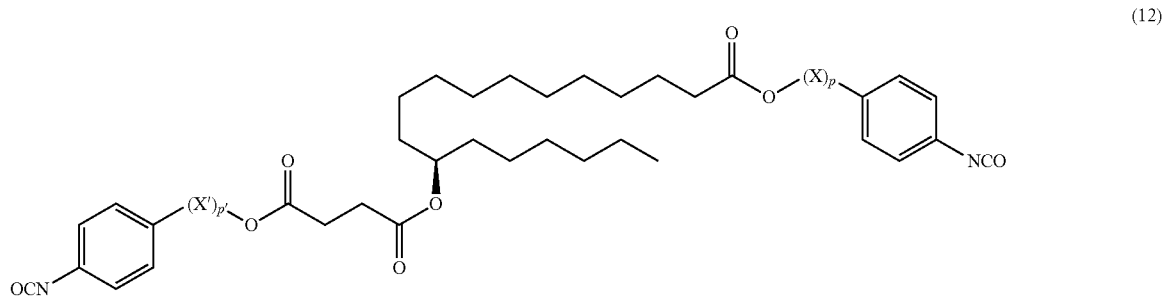
(13)
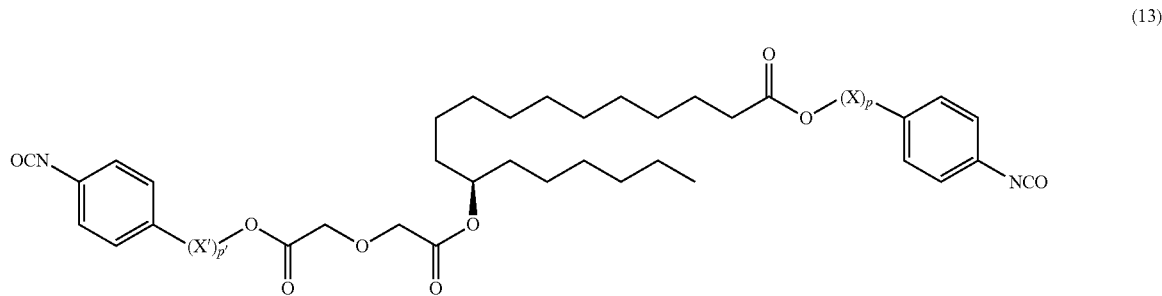

-continued
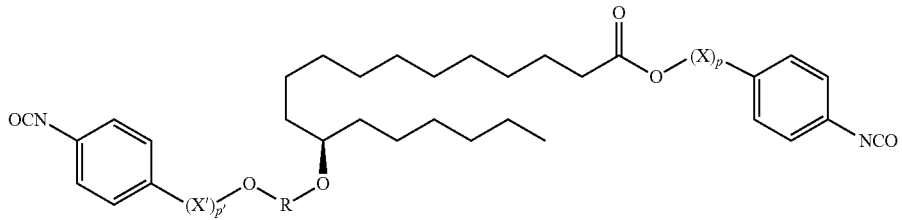
(14)
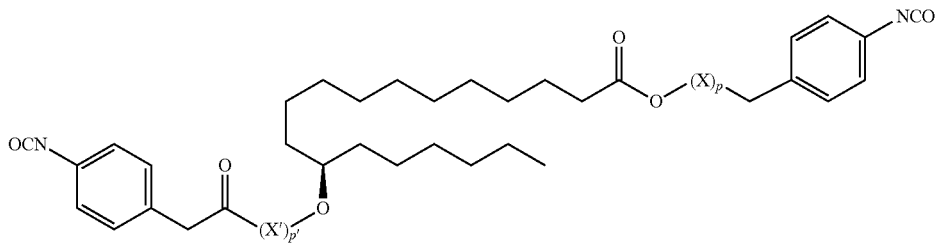
(15)
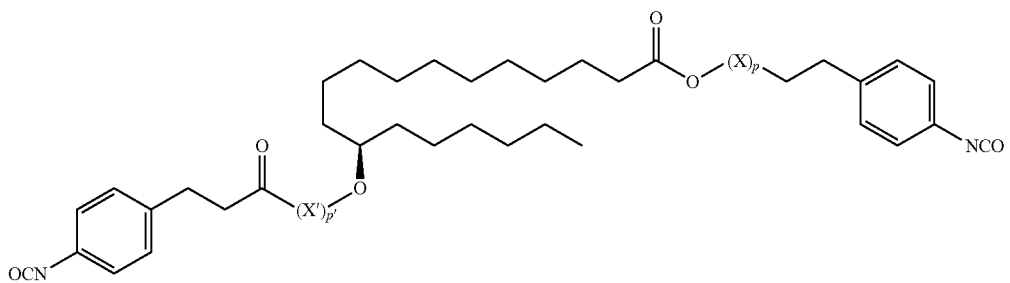
(16)
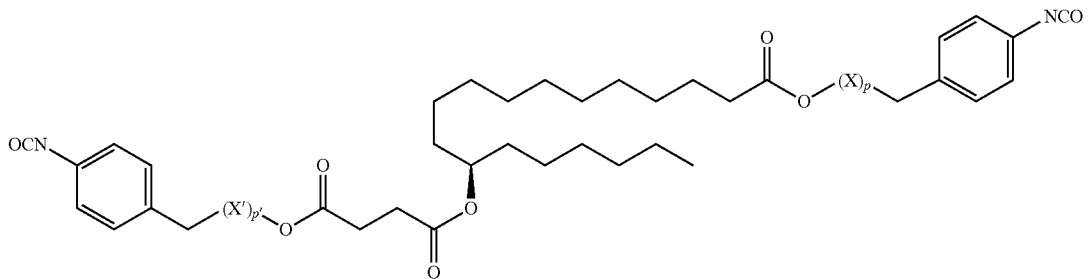
(17)
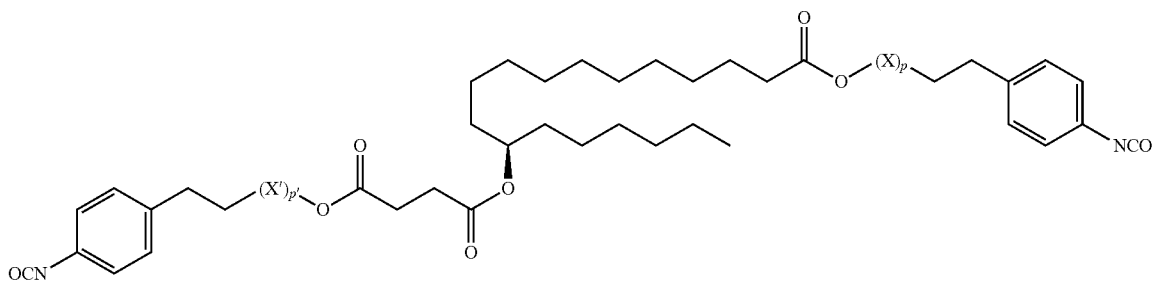
(18)

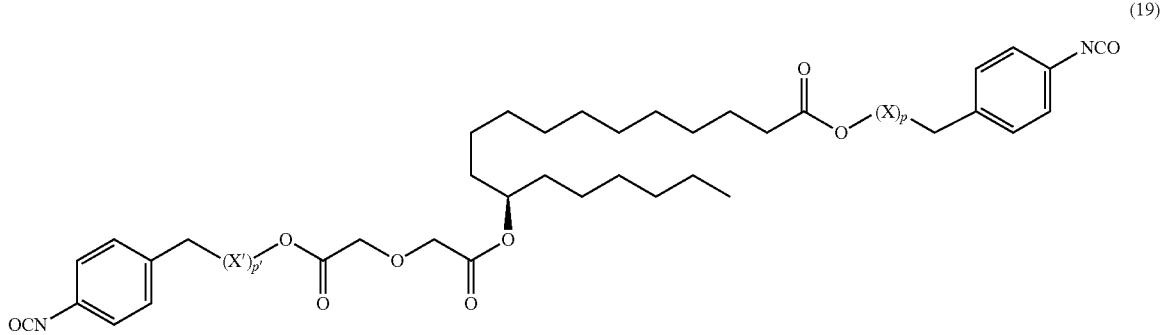

(19)

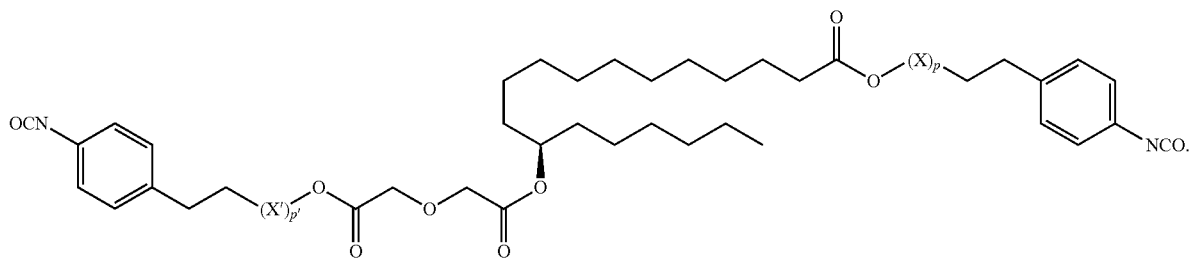

(20)

6. The diisocyanate of claim 1, wherein:
each p is independently selected from 0, 1, 2, 3, and 4; and,
each p' is independently selected from 0, 1, 2, 3, and 4;
provided that p+p' total from 2-4.

7. The diisocyanate of claim 2, wherein:
each p is independently selected from 0, 1, 2, 3, and 4; and,
each p' is independently selected from 0, 1, 2, 3, and 4;
provided that p+p' total from 2-4.

8. The diisocyanate of claim 3, wherein:
each p is independently selected from 0, 1, 2, 3, and 4; and,
each p' is independently selected from 0, 1, 2, 3, and 4;
provided that p+p' total from 2-4.

9. The diisocyanate of claim 4, wherein:
each p is independently selected from 0, 1, 2, 3, and 4; and,
each p' is independently selected from 0, 1, 2, 3, and 4;
provided that p+p' total from 2-4.

10. The diisocyanate of claim 5, wherein:
each p is independently selected from 0, 1, 2, 3, and 4; and,
each p' is independently selected from 0, 1, 2, 3, and 4;
provided that p+p' total from 2-4.

11. The diisocyanate of claim 5, wherein the diisocyanate is of formulae (1).

12. The diisocyanate of claim 5, wherein the diisocyanate is of formulae (2).

13. The diisocyanate of claim 5, wherein the diisocyanate is of formulae (3).

14. The diisocyanate of claim 5, wherein the diisocyanate is of formulae (4).

15. The diisocyanate of claim 5, wherein the diisocyanate is of formulae (5).

16. The diisocyanate of claim 5, wherein the diisocyanate is of formulae (6).

17. The diisocyanate of claim 5, wherein the diisocyanate is of formulae (7).

18. The diisocyanate of claim 5, wherein the diisocyanate is of formulae (8).

19. The diisocyanate of claim 5, wherein the diisocyanate is of formulae (9).

20. The diisocyanate of claim 5, wherein the diisocyanate is of formulae (10).

21. The diisocyanate of claim 5, wherein the diisocyanate is of formulae (11).

22. The diisocyanate of claim 5, wherein the diisocyanate is of formulae (12).

23. The diisocyanate of claim 5, wherein the diisocyanate is of formulae (13).

24. The diisocyanate of claim 5, wherein the diisocyanate is of formulae (14).

25. The diisocyanate of claim 5, wherein the diisocyanate is of formulae (15).

26. The diisocyanate of claim 5, wherein the diisocyanate is of formulae (16).

27. The diisocyanate of claim 5, wherein the diisocyanate is of formulae (17).

28. The diisocyanate of claim 5, wherein the diisocyanate is of formulae (18).

29. The diisocyanate of claim 5, wherein the diisocyanate is of formulae (19).

30. The diisocyanate of claim 5, wherein the diisocyanate is of formulae (20).

* * * * *